US008901075B2

(12) United States Patent
Shailubhai et al.

(10) Patent No.: US 8,901,075 B2
(45) Date of Patent: *Dec. 2, 2014

(54) AGONISTS OF GUANYLATE CYCLASE USEFUL FOR THE TREATMENT OF GASTROINTESTINAL DISORDERS, INFLAMMATION, CANCER AND OTHER DISORDERS

(71) Applicant: Synergy Pharmaceuticals Inc., New York, NY (US)

(72) Inventors: Kunwar Shailubhai, Audubon, PA (US); Gary S. Jacob, New York, NY (US)

(73) Assignee: Synergy Pharmaceuticals, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/857,283

(22) Filed: Apr. 5, 2013

(65) Prior Publication Data

US 2014/0024605 A1 Jan. 23, 2014

Related U.S. Application Data

(63) Continuation of application No. 13/010,267, filed on Jan. 20, 2011, now Pat. No. 8,716,224, which is a continuation of application No. 12/133,344, filed on Jun. 4, 2008, now Pat. No. 7,879,802.

(60) Provisional application No. 60/933,194, filed on Jun. 4, 2007.

(51) Int. Cl.
*A61K 38/00* (2006.01)
*C07K 7/08* (2006.01)
*C07K 7/64* (2006.01)
*A61K 47/48* (2006.01)

(52) U.S. Cl.
CPC ... *C07K 7/64* (2013.01); *C07K 7/08* (2013.01); *A61K 47/48215* (2013.01)
USPC .......................................... 514/13.2; 514/13.3

(58) Field of Classification Search
None
See application file for complete search history.

(56) References Cited

U.S. PATENT DOCUMENTS

| | | | |
|---|---|---|---|
| 5,489,670 A | 2/1996 | Currie et al. | |
| 5,518,888 A | 5/1996 | Waldman | |
| 5,578,709 A | 11/1996 | Woiszwillo | |
| 5,601,990 A | 2/1997 | Waldman | |
| 5,731,159 A | 3/1998 | Waldman | |
| 5,879,656 A | 3/1999 | Waldman | |
| 5,928,873 A | 7/1999 | Waldman | |
| 5,969,097 A | 10/1999 | Wiegand et al. | |
| 6,060,037 A | 5/2000 | Waldman | |
| 6,235,782 B1 | 5/2001 | Pamukcu et al. | |
| 7,041,786 B2 | 5/2006 | Shailubhai et al. | |
| 7,879,802 B2 * | 2/2011 | Shailubhai et al. | 514/20.6 |
| 2002/0078683 A1 | 6/2002 | Katayama et al. | |
| 2002/0128176 A1 | 9/2002 | Forssmann et al. | |
| 2002/0133168 A1 | 9/2002 | Smedley et al. | |
| 2003/0073628 A1 | 4/2003 | Shailubhai et al. | |
| 2004/0015140 A1 | 1/2004 | Shields | |
| 2005/0016244 A1 | 1/2005 | Hergemoller | |
| 2005/0032684 A1 | 2/2005 | Cetin et al. | |
| 2005/0107734 A1 | 5/2005 | Coroneo | |
| 2005/0266047 A1 | 12/2005 | Tu et al. | |
| 2006/0086653 A1 | 4/2006 | St. Germain | |
| 2007/0101158 A1 | 5/2007 | Elliott | |
| 2008/0137318 A1 | 6/2008 | Rangaraj et al. | |
| 2008/0151257 A1 | 6/2008 | Yasuda et al. | |
| 2012/0196797 A1 | 8/2012 | Currie et al. | |

FOREIGN PATENT DOCUMENTS

| | | |
|---|---|---|
| DE | 19744027 | 4/1999 |
| WO | WO-8805306 | 7/1988 |
| WO | WO-9926567 A1 | 6/1999 |
| WO | WO-0125266 A1 | 4/2001 |
| WO | WO-02062369 A2 | 8/2002 |
| WO | WO-02078683 A1 | 10/2002 |
| WO | WO-02098912 A2 | 12/2002 |
| WO | WO-2004069165 A2 | 8/2004 |
| WO | WO-2005016244 A2 | 2/2005 |
| WO | WO-2005087797 A1 | 9/2005 |
| WO | WO-2006086653 A2 | 8/2006 |
| WO | WO-2007022531 A2 | 2/2007 |
| WO | WO-2007101158 A2 | 9/2007 |
| WO | WO-2008106429 A2 | 9/2008 |
| WO | WO-2008137318 A1 | 11/2008 |
| WO | WO-2008151257 A2 | 12/2008 |
| WO | WO-2009149278 A1 | 12/2009 |

(Continued)

OTHER PUBLICATIONS

Askling et al. "Colorectal Cancer Rates Among First Degree Relatives of Patients with Inflammatory Bowel Disease: A Population-Based Cohort Study." *Lancet.* 357(2001):262-266.

(Continued)

*Primary Examiner* — Sheela J Huff
(74) *Attorney, Agent, or Firm* — Cooley LLP

(57) ABSTRACT

The invention provides novel guanylate cyclase-C agonist peptides and their use in the treatment of human diseases including gastrointestinal disorders, inflammation or cancer (e.g., a gastrointestinal cancer). The peptides can be administered either alone or in combination with an inhibitor of cGMP-dependent phosphodiesterase. The gastrointestinal disorder may be classified as irritable bowel syndrome, constipation, or excessive acidity etc. The gastrointestinal disease may be classified as either inflammatory bowel disease or other GI condition, including Crohn's disease and ulcerative colitis, and cancer.

6 Claims, 17 Drawing Sheets

(56) References Cited

FOREIGN PATENT DOCUMENTS

| | | |
|---|---|---|
| WO | WO-2009149279 A2 | 12/2009 |
| WO | WO-2010009319 A2 | 1/2010 |
| WO | WO-2010065751 A2 | 6/2010 |

OTHER PUBLICATIONS

Barbara et al. "A Role for Inflammation in Irritable Bowel Syndrome." *Gut.* 51.S1(2002):141-144.
Basoglu et al. Proceedings of the Second FEPS Congress, Jun. 29-Jul. 4, 1999, Prague, Czech Republic, If2.cuni.cz/physiolres/feps/basoglu.htm.
Baxter et al. "Natriuretic Peptides and Myocardial Ischaemia." *Basic Res. Cardiol.* 99.2(2004):71-75.
Bergers et al. "Extrinsic Regulators of Epithelial Tumor Progression: Metalloproteinases." *Curr. Opin. Gen. Dev.* 10(2000):120-127.
Beltowski. "Guanylin and Related Peptides." *J. Physiol. Pharmacol.* 52.3(2001):351-375.
Bhakdi et al. "Release of Interleukin-1β Associated with Potent Cytocidal Action of Staphylococcal Alpha-Toxin on Human Monocytes." *Infect. Immun.* 57.11(1989):3512-3519.
Brown et al. "A Receptor-Medicated Pathway for Cholesterol Homeostasis." *Science.* 232(1986):34-47.
Burnham. "Polymers for Delivering Peptides and Proteins." *Am. J. Hosp. Pharm.* 51(1994):210-218.
Caliceti et al. "Synthesis and Biopharmaceutical Characterisation of New Poly(Hydroxyethylaspartamide) Copolymers as Drug Carriers." *Biochim. Biophys. Acta.* 1528(2001):177-186.
Camilleri et al. "Management of the Irritable Bowel Syndrome." *Gastroenterol.* 120(2001):652-668.
Carrithers et al. "Guanylyl Cyclase C is a Selective Marker for Metastatic Colorectal Tumors in Human Extraintestinal Tissues." *PNAS.* 93(1996):14827-14832.
Cermak et al. "Natriuretic Peptides Increase a K+ Conductance in Rat Mesangial Cells." *Pflügers Arch.-Eur. J. Physiol.* 431(1996):571-577.
Cheng et al. "Defective Intracellular Transport and Processing of CFTR is the Molecular Basis of Most Cystic Fibrosis." *Cell.* 63(1990):827-834.
Chino et al. "Topological Isomers of Human Uroguanylin: Interconversion Between Biologically Active and Inactive Isomers." *FEBS Lett.* 421(1998):27-31.
Cohen et al., "Guanylin mRNA expression in human intestine and colorectal adenocarcinoma", *Lab. Invest.,* 78:101-108 (1998).
Collins, SM., "The Relationship of Enteric Microbial Infection and Functional Bowel Disorders", *J. Clin. Gastroenterol,* 41 Suppl. 1:S30-32 (2007).
Cui et al., "The Permissive Effect of Zinc Deficiency on Uroguanylin and Inducible Nitric Oxide Synthase Gene Upregulation in Rat Intestine Induced by Interleukin 1a is Rapidly Reversed by Zinc Repletion", *J. Nutri.,* 133(1): 51-56 (2003).
Currie et al., "Guanylin: an endogenous activator of intestinal guanylate cyclase", *Proc. Natl. Acad. Sci. USA,* 89:947-951 (1992).
Database BIOSIS (Online), Biosciences Information Service, Philadelphia, PA, U.S., Apr. 2006, Refaat et al., "Sp304, an analog of uroguanylin, ameliorates inflammation in a model of experimental colitis", XP002540570, Database Accession No. PREV200600503788.
De Luca et al., "Inflammation and Insulin Resistance", FEBS Letter, 582:97-105 (2008).
De Sauvage et al., "Precursor structure, expression, and tissue distribution of human guanylin", *Proc. Natl. Acad. Sci. USA,* 89:9089-9093 (1992).
Delvaux et al., "Effect of alosetron on responses to colonic distension in patients with irritable bowel syndrome", *Aliment Pharmacol. Ther.,* 12:849-855 (1998).
Dennis et al. "Off by a whisker", *Nature,* 442:739-741 (2006).
Deschner et al., "Proliferative defects in ulcerative colitis patients", *Can. Invest.,* 1:41-47 (1983).

Dunfield et al., "Energy parameters in polypeptides. 8. Empirical potential energy algorithm for the conformational analysis of large molecules", *J. Phys. Chem.,* 82:2609-2616 (1978).
Eastwood, G. "Epithelial Renewal in Premalignant Conditions of the Gastrointestinal Tract: A Review ", *J. Clin. Gastroenterol,* 14(1):S29-S33 (1992).
Ettorre et al., "Mucosal changes in ileal pouches after restorative proctocolectomy for ulcerative and Crohn's colitis", Dis. Colon Rectum, 43:1743-1748 (2000).
Evan et al., "Proliferation, cell cycle and apoptosis in cancer", *Nature (London),* 411:342-348 (2001).
Forte, L.R., "Guanylin regulatory peptides: Structures, biological activities mediated by cyclic GMP and pathobiology", *Reg. Pep.,* 81(1-3):25-39 (1999).
Gali et al., "In Vivo Evaluation of an 111In-labeled ST-peptide Analog for Specific-Targeting of Human Colon Cancers", *Nucl. Med. Bio.,* 28(8):903-909 (2001).
Garcia et al., "Processing and characterization of human proguanylin expressed in *Escherichia coli*", *J. Biol. Chem.,* 268(30):22397-22401 (1993).
Greenberg et al., "Comparison of effects of uroguanylin, guanylin, and *Escherichia coli* heat-stable enterotoxin STa in mouse intestine and kidney: evidence that uroguanylin is an intestinal natriuretic hormone", *J. Invest. Med.,* 45(5):276-282 (1997).
Guba et al., "Guanylin strongly stimulates rat duodenal HCO3-secretion: proposed mechanism and comparison with other secretagogues", *Gastroenterol.,* 111(6):1558-1568 (1996).
Gülcan et al., "Increased Frequency of Pre-diabetes in Patients With Irritable Bowel Syndrome", *Am. J. Med. Sci.,* 338:116-119 (2009).
Gülcan et al., "The Predictive Value of CRP Levels on Future Severe Renal Disease in Overweight and Obese Subjects Without Diabetes Mellitus and Hypertension", *Am. J. Med. Sci.,* 334:444-451 (2007).
Gura, T., "Systems for identifying new drugs are often faulty", *Sci.,* 278:1041-1042 (1997).
Hamman et al., "Oral delivery of peptide drugs", BioDrugs, 19(3):165-177 (2005).
Hamra et al., "Uroguanylin: structure and activity of a second endogenous peptide that stimulates intestinal guanylate cyclase", *Proc. Natl. Acad. Sci. USA,* 90:10464-10468 (1993).
Harris et al., "Drug evaluation: linaclotide, a new direction in the treatment of irritable bowel syndrome and chronic constipation", *Curr. Opin. Mol. Ther.,* 9(4):403-410 (2007).
Hidaka et al., "Dual Function of the Propeptide of Prouroguanylin in the Folding of the Mature Peptide: Disulfide-Coupled Folding and Dimerization", *J. Biol. Chem.,* 33:25155-25162 (2000).
Hidaka et al., "In Vitro Disulfide-Coupled Folding of Guanylyl Cyclase-Activating Peptide and its Precursor Protein", Biochem., 37:8498-8507 (1998).
Hill et al., "A new human guanylate cyclase-activating peptide (GCAP-II, uroguanylin): precursor cDNA and colonic expression", *Biochemica Biophysica Acta,* 12(53):146-149 (1995).
Hill et al., "Analysis of the human guanylin gene and the processing and cellular localization of the peptide", Proc. Natl. Acad. Sci. USA, 92:2046-2050 (1995).
Hinds et al., "Synthesis and Characterization of Poly(ethylene glycol)-Insulin Conjugates http://pubs.acs.org/doi/abs/10.1021/bc9901189", *Bioconjug. Chem.,* 11:195-201 (2000).
Hudson et al., "Rethinking cystic fibrosis pathology: the critical role of abnormal reduced glutathione (GSH) transport caused by CFTR mutation", *Free Rad. Biol. Med.,* 30:1440-1461 (2001).
Hughes et al., "Intracellular K+ Suppresses the Activation of Apoptosis in Lymphocytes", *J. Biol. Chem.,* 272(48):30567-30576 (1997).
Joo et al., "Regulation of intestinal Cl- and HCO3-secretion by uroguanylin", *Am. J. Physiol,* 274:G633-G644 (1998).
Kelland L.R., "Of mice and men: values and liabilities of the athymic nude mouse model in anticancer drug development", *Eur. J. Can.,* 40:827-836 (2004).
Klodt et al., "Synthesis, biological activity and isomerism of guanylate cyclase C-activating peptides guanylin and uroguanylin", *J. Pep. Res.,* 50(2):77-152(1997).
Lam et al., "Serotonin and energy balance: molecular mechanisms and implications for type 2 diabetes", *Expert Rev. Mol. Med.,* 9:1-24 (2007).

(56) References Cited

OTHER PUBLICATIONS

Leister et al., "Human Colorectal Cancer: High Frequency of Deletions at Chromosome 1p35", Can. Res., 50:7232-7235 (1990).
Lipkin, M., "Gastric cell regeneration", Arch. Fr. Mal. Appl. Dig. (Paris), 61(10-11):691-693 (1972).
Lorenz et al., "Uroguanylin knockout mice have increased blood pressure and impaired natriuretic response to enteral NaCl load", J. Clin. Invest., 112(8):1244-1254 (2003).
Mahato et al., "Emerging trends in oral delivery of peptide and protein drugs", Crit. Rev. Ther. Drug Carrier Systems, 20(2-3):153-214 (2003).
Miyazato et al., "Cloning and Characterization of a cDNA Encoding a Precursor for Human Uroguanylin", Biochem. Biophys. Res. Comm., 219:644-648 (1996).
Moon et al., "Effects of age, ambient temperature, and heat-stable Escherichia coli enterotoxin on intestinal transit in infant mice", Infect. Immun., 25(1):127-132 (1979).
Mü-Lissner et al., "Safety, Tolerability, and Efficacy of Tegaserod over 13 Months in Patients with Chronic Constipation", Am. J. Gastroenterol., 101:2558-2569 (2006).
Nathan et al., "Copolymers of lysine and polyethylene glycol: a new family of functionalized drug carriers <http://pubs.acs.org/doi/abs/10.1021/bc00019a008>", Bioconjug. Chem., 4(1):54-62 (1993).
Nemethy et al., "Energy parameters in polypeptides. 9. Updating of geometrical parameters, non-bonded interactions, and hydrogen bond interactions for the naturally occurring amino acids", J. Phys. Chem., 87:1883-1887 (1983).
Nikiforovich et al., "Topographical requirements for -selective opioid peptides", Biopolymers, 31:941-955 (1991).
Nikiforovich, G., "Computational molecular modeling in peptide design", Int. J. Pep. Prot. Res., 44:513-531 (1994).
Nyburg et al., "Some uses of best molecular fit routine Acta", Crystallographica B30 (Part I):251-253 (1974).
Ohbayashi et al., "Effects of Uroguanylin and Guanylin Against Antigen-Induced Bronchoconstriction and Airway Microvascular Leakage in Sensitized Guinea-Pigs", Life Sci., 62(20): 1833-1844 (1998).
Peterson et al., "Integrating pharmacology and in vivo cancer models in preclinical drug development", Eur. J. Can., 40:837-844 (2004).
Pitari et al., "Guanylyl cyclase C agonists regulate progression through the cell cycle of human colon carcinoma cells", Proc. Natl. Acad. Sci. USA, 98(14):7846-7851 (2001).
Potten et al., "Regulation and Significance of Apoptosis in the Stem Cells of the Gastrointestinal Epithelium", Stem Cells, 15:82-93 (1997).
Provenzale et al., "Surveillance Issues in Inflammatory Bowel Disease: Ulcerative Colitis", J. Clin. Gastroenterol, 32:99-105 (2001).
Ramamoorthy et al., "Phosphorylation of Threonine Residue 276 Is Required for Acute Regulation of Serotonin Transporter by Cyclic GMP", J. Biol. Chem., 282(16):11639-11647 (2007).
Samuel et al., "Absorption of bile acids from the large bowel in man", J. Clin. Invest., 47:2070-2078 (1968).
Schulz, et al., "Side Chain Contributions to the Interconversion of the Topological Isomers of Guanylin-like Peptides", J. Pep. Sci., 11(6):319-330 (2005).
Schulz et al., "Guanylyl cyclase is a heat-stable enterotoxin receptor", Cell, 63(5):941-948 (1990).
Sciaky et al., "Mapping of guanylin to murine chromosome 4 and human chromosome Genomics", 26:427-429 (1995).
Sellers et al., "Heat-stable enterotoxin of Escherichia coli stimulates a non-CFTR-mediated duodenal bicarbonate secretory pathway", Am. J. Physiol. Gastrointest. Liver Physiol., 288:G654-G663 (2005).
Shailubhai et al., "Guanilib, an agonist of Guanylate C, is a new class of oral drug candidate for GI disorders and colon cancer", [Abstract]: In GTCbio, 2008.
Shailubhai et al., "Guanilib, an antagonist of Guanylate C, is a new class of oral drug candidate that amerliorates inflammation in models of experimental colitis", [Abstract]: In Crohn's and Colitis Foundation of America, 2007.
Shailubhai et al., "SP-304 to Treat GI Disorders—Effects of a Single, Oral Dose of SP-304 in Safety, Tolerability, Pharmaokinetics and Pharmacodynamics in Healthy Volunteers", [Abstract]; In Digestive Disease Week, 2009.
Shailubhai et al., "Uroguanylin Treatment Suppresses Polyp Formation in the Apc Min/+ Mouse and Induces Apoptosis in Human Colon Adenocarcinoma Cells in via Cyclic GMP", Can. Res., 60:5151-5157 (2000).
Shailubhai et al., "Guanylin Peptides: New Class of Oral Drug Candidates", [Abstract]: In World Congress, 2008.
Shailubhai et al., Clin. Cancer Res., (Proc. 1999 AACR NCI EORTC Int. Conf.), [Abstract], 5(Suppl.) (1999).
Shailubhai et al., "Guanylate Cyclase-C Agonists as a New Class of Drug Candidates for GI Motility and Inflammatory Bowel Disease", [Abstract] (2009).
Shailubhai et al., "Therapeutic Applications of Guanylate Cyclase-C Receptor Agonists" Curr. Opin. Drug Disc. Develop., 5(2):261-268 (2002).
Shinozaki et al., "High proliferative activity is associated with dysplasia in ulcerative colitis", Dis. Colon Rectum, 43:S34-S39 (2000).
Spranger et al., "Inflammatory Cytokines and the Risk to Develop Type 2 Diabetes: Results of the Prospective Population-Based European Prospective Investigation into Cancer and Nutrition (EPIC)-Potsdam Study", Diabetes, 52:812-817 (2003).
Takada et al., "Alteration of a Single Amino Acid in Peroxisome Proliferator-Activated Receptor-(PPAR ) Generates a PPAR Phenotype", Mol. Endocrinol., 14(5):733-740 (2000).
Talley et al., "Medical costs in community subjects with irritable bowel syndrome", Gastroenterol., 109:1736-1741 (1995).
Tian et al., "STa Peptide Analogs for Probing Guanylyl Cyclase C", Biopolymers (Pept. Sci), 90(5):713-723 (2008).
Tilg et al., "Inflammatory Mechanisms in the Regulation of Insulin Resistance", Mol. Med., 14:222-231 (2008).
Vaandrager, A.B., "Structure and Function of the Heat Stable Enterotoxin Receptor/Guanylyl Cyclase C", Mol. Cell. Biochem., 230:73-83 (2002).
Venkatakrishnan et al., "Exaggerated Activation of Nuclear Factor-B and Altered I B-Processing in Cystic Fibrosis Bronchial Epithelial Cells", Am. J. Resp. Cell Mol. Biol., 23(3):396-403 (2000).
Veronese F.M., "Peptide and protein PEGylation: a review of problems and solutions", Biomaterials, 22:405-417 (2001).
Weber et al., Activation of NF-B in airway epithelial cells is dependent on CFTR trafficking and CI channel function, Am. J. Physiol. Lung Cell Mol. Biol., 281(1):L71-78 (2001).
Welsh et al., "Molecular mechanisms of CFTR chloride channel dysfunction in cystic fibrosis", Cell, 73:1251-1254 (1993).
Whitaker et al., "The Uroguanylin Gene (Guca1b) Is Linked to Guanylin (Guca2) on Mouse Chromosome 4", Genomics, 45:348-354 (1997).
Wong et al., "Cell proliferation in gastrointestinal mucosa", J. Clin. Pathol., 52:321-33 (1999).
Wong et al., "Histogenesis of human colorectal adenomas and hyperplastic polyps: the role of cell proliferation and crypt fission", Gut, 50:212-217 (2002).
Wu et al. "Atrial Natriuretic Peptide Induces Apoptosis in Neonatal Rat Cardiac Myocytes." J. Biol. Chem. 272.23(1997):14860-14866.
Zhang et al. "Gene Expression Profiles in Normal and Cancer Cells." Science. 276(1997):1268-1272.
Zimmerman et al. "Influence of Local Interactions on Protein Structure." Biopolymers. 16(1977):811-843.
Sindic et al., "Guanylin, Uroguanylin, and Heat-stable Euterotoxin Activate Guanylate Cyclase C and/or a Pertussis Toxin-sensitive G Protein in Human Proximal Tubule Cells", J. Biol. Chem., 277:17758-17764 (2002).
Bakre et al. "Expression and Regulation of the cGMP-Binding, cGMP-Specific Phosphodiesterase (PDE5) in Human Colonic Epithelial Cells: Role in the Induction of Cellular Refractoriness to the Heat-stable Enterotoxin Peptide." J. Cell. Biol. 77(2000):159-167.
Duncan, Ruth, "Drug-polymer COnjugates: Potential for Imporved Chemotherapy", Anti-Can. Drugs, 3:175-210 (1992).

(56) References Cited

OTHER PUBLICATIONS

Fan et al., "Structure and Activity of Uroguanylin and Guanylin from the Intestine and Urine of Rats", *Am. J. Physiol. Endocrinol. Metab.*, 273:957-964 (1997).
Fonteles, et al., "Natriuretic and Kaliuretic Activities of Guanylin and Uroguanylin in Isolated Perfused Rat Kidney", *Am. J. Physiol. Renal Physiol.*, 275:191-197 (1998).
Genbank IUYAA—Chain A, Solution Structure A—Form Uroguanylin, Mar. 15, 2010.
Genbank 1UYBA—Chain A, Solution Structure B—Form Uroguanylin, Mar. 15, 2010.
GenBank: AAB18760.1 (rat, 1995), Mar. 11, 2010.
GenBank: AAB30324.1; GUCA2B (human, 1994), Mar. 11, 2010.
GenBank: AAD09215.1 (mouse, 1996), Mar. 11, 2010.
GenBank: CAA98994.1 (guinea pig, 1996), Mar. 11, 2010.
GenBank: CAB06042.1 (pig, 1996), Mar. 11, 2010.
Kita et al., "Characterization of Human Uroguanylin: A Member of the Guanylin Peptide Family", *Am. J. Physiol.*, 266:F342-8 (1994).
Krause et al., "The Guanylin and Uroguanylin Peptide Hormones and Their Receptors", *Acta Anat.*, 160:213-231 (1997).
Li et al., "Purification, cDNA Sequence and Tissue Distribution of Rat Uroguanylin", *Reg. Pep.*, 68:45-56 (1997).
Magert et al., "Porcine Guanylin and Uroguanylin: cDNA Sequences, Deduced Amino Acid Sequences, and Biological Activity of the Chemically Synthesized Peptides", *Biochem. Biophys. Res. Comm.*, 259:141-148 (1999).
Marx et al., "One Peptide, Two Topologies: Structure and Interconversion Dynamics of Human Uroguanylin Isomers", *J.Pep. Res.*, 52:229-240 (1998).
Genbank AAC50416.1; GUCA2B (human, 1994), Mar. 11, 2010.
Genbank: PRF: 738946 (opossum, 1993), Mar. 15, 2011.
Miyazato et al., "Uroguanylin Gene Expression in the Alimentary Tract and Extra-Gastrointestinal Tissues", *FEBS Letters*, 398:170-174 (1996).
Nakazato et al., "Tissue Distribution, Cellular Source, and Structural Analysis of Rat Immunoreactive Uroguanylin", *Endocrinol.*, 139:5247-5254 (1998).
Perkins et al., "Uroguanylin is Expressed by Enterochromaffin Cells in the Rat Gastrointestinal Tract", *Gastroenterol.*, 113:1007-1014 (1997).
Remington, JP., *Remington's Pharmaceutical Sciences*, Mack Pub. Co., 16th edition (1980).
Waldman et al., "Heterogeneity of Guanylyl Cyclase C Expressed by Human Colorectal Cancer Cell Lines in Vitro", *Can. Epidemiol., Biomarkers & Prevention*, 7:505-514 (1998).
Whitaker et al., "Uroguanylin and Guanylin: Distint but Overlapping Patterns of Messenger RNA Expression Mouse Intestine", *Gastroenterol.*, 113(3):1000-6 (1997).
Veronese et al., "BioConjugation in Pharmaceutical Chemistry", *Farmaco*, 54:497-516 (1999).
Response to European Patent Office Communication dated Mar. 16, 2007 for European Application No. 02721604.3.
European Patent Office Communication dated Aug. 12, 2008.
Opposition to European Patent No. 1,379,224 B1 by Christopher Michael Hill dated Apr. 22, 2010.
CombiMab, Inc. Annex to Notice of Opposition against European Patent 1,379,224 B1 dated Apr. 22, 2010.
Summons to Attend Oral Hearing and Preliminary Opinion of the Opposition Division dated Jun. 24, 2011 for European Patent Application No. 02721604.
Response to Communication from Opposition Division relating to European Patent No. 1379224.3 dated Oct. 8, 2010.
Written submission dated Oct. 7, 2011 in response to the Jun. 24, 2011 preliminary opinion of the Opposition Division regarding European Patent Application No. 02721604.3.
Written submission dated Oct. 14, 2011 by Ironwood regarding European Patent Application No. 02721604.3.
Written submission dated Oct. 14, 2011 regarding European Patent Application No. 02721604.3.
Written submission dated Oct. 25, 2011 regarding European Patent Application No. 02721604.3.
Written submission dated Nov. 18, 2011 regarding European Patent Application No. 02721604.3.
Written submission dated Nov. 22, 2011 regarding European Patent Application No. 02721604.3.
Written submission dated Dec. 7, 2011 regarding European Patent Application No. 02721604.3.
Roberts et al, "Chemistry of Peptide and Protein PEGylation." *Adv. Drug. Deliv. Rev.* 54(2002):459-476.
Reddy et al. "Lipid Metabolism and Liver Inflammation II Fatty Liver Disease and Fatty Acid Oxidation." *Am. J. Physiol. Gastrointest. Liver Physiol.* 290(2006):G852-G858.
http://www.merckmanuals.com/home/childrens_health_issues/hereditary_metabolic_disorders/disorders_of_lipid_metabolism.html; last updated 2009; last visited Sep. 25, 2012.
http://www.nlm.nih.gov/medlineplus/obesity.html; 1999-2011; last visited Sep. 25, 2012.
St. John's Providence Health Center; Preventing Obesity, http://www.stjohnprovidence.org/HealthInfoLib/swArticle.aspx?85,P07863; last visited Sep. 25, 2012.
Advisory Committee Briefing Document for Merida [sibutramine hydrochloride monohydrate], Abbott, Aug. 13, 2010.
Veronese et al., "PEGylation, successful approach to drug delivery", *Drug Disc. Today*, 10(21):451-1458 (2005).
Shailubhai et al. "Inflammatory Bowel Disease", Feb. 2008: S5 2007 IBD Abstracts: Oral Presentation.
Howard et al., "Obesity and Dyslipidemia", Endocrinol. Metab. Clin. N. Am., 32:855-867 (2003).

* cited by examiner

SEQUENCE LISTING

```
<160> NUMBER OF SEQ ID NOS: 123

<210> SEQ ID NO 1
<211> LENGTH: 16
<212> TYPE: PRT
<213> ORGANISM: Artificial Sequence
<220> FEATURE:
```

<223> OTHER INFORMATION: Chemically Synthesized

<400> SEQUENCE: 1

Asn Asp Glu Cys Glu Leu Cys Val Asn Val Ala Cys Thr Gly Cys Leu
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 2

Asp Glu Cys Glu Leu Cys Val Asn Val Ala Cys Thr Gly Cys Leu
1               5                   10                  15

<210> SEQ ID NO 3
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 3

Asp Glu Cys Glu Leu Cys Val Asn Val Ala Cys Thr Gly Cys
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 4

Glu Cys Glu Leu Cys Val Asn Val Ala Cys Thr Gly Cys Leu
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 5

Glu Cys Glu Leu Cys Val Asn Val Ala Cys Thr Gly Cys
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 6

Cys Glu Leu Cys Val Asn Val Ala Cys Thr Gly Cys Leu
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 7

Cys Glu Leu Cys Val Asn Val Ala Cys Thr Gly Cys
1               5                   10

<210> SEQ ID NO 8
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein x is a D-LEU

<400> SEQUENCE: 8

Asn Asp Glu Cys Glu Leu Cys Val Asn Val Ala Cys Thr Gly Cys Xaa
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (16)..(16)
<223> OTHER INFORMATION: wherein x is a D-LEU

<400> SEQUENCE: 9

Xaa Asp Glu Cys Glu Leu Cys Val Asn Val Ala Cys Thr Gly Cys Xaa
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (2)..(2)
<223> OTHER INFORMATION: wherein x is a D-ASP
<220> FEATURE:
<221> NAME/KEY: MISC_FEATURE
<222> LOCATION: (16)..(16)
<223> OTHER INFORMATION: wherein x is a D-LEU

<400> SEQUENCE: 10

Xaa Xaa Glu Cys Glu Leu Cys Val Asn Val Ala Cys Thr Gly Cys Xaa
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)

```
<223> OTHER INFORMATION: wherein x is a D-ASN
<220> FEATURE:
<221> NAME/KEY: MISC_FEATURE
<222> LOCATION: (2)..(2)
<223> OTHER INFORMATION: wherein x is a D-ASP
<220> FEATURE:
<221> NAME/KEY: MISC_FEATURE
<222> LOCATION: (3)..(3)
<223> OTHER INFORMATION: wherein x is a D-GLU
<220> FEATURE:
<221> NAME/KEY: MISC_FEATURE
<222> LOCATION: (16)..(16)
<223> OTHER INFORMATION: wherein x is a D-LEU

<400> SEQUENCE: 11

Xaa Xaa Xaa Cys Glu Leu Cys Val Asn Val Ala Cys Thr Gly Cys Xaa
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is a D-ASN

<400> SEQUENCE: 12

Xaa Asp Glu Cys Glu Leu Cys Val Asn Val Ala Cys Thr Gly Cys Leu
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (6)..(6)
<223> OTHER INFORMATION: wherein x is a D-LEU
<220> FEATURE:
<221> NAME/KEY: MISC_FEATURE
<222> LOCATION: (16)..(16)
<223> OTHER INFORMATION: wherein x is a D-LEU

<400> SEQUENCE: 13

Xaa Asp Glu Cys Glu Xaa Cys Val Asn Val Ala Cys Thr Gly Cys Xaa
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 14

Asn Asp Glu Cys Glu Leu Cys Val Asn Val Ala Cys Thr Gly Cys
1               5                   10                  15

<210> SEQ ID NO 15
<211> LENGTH: 16
<212> TYPE: PRT
<213> ORGANISM: Artificial Sequence
```

-continued

```
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (16)..(16)
<223> OTHER INFORMATION: wherein x is a D-LEU
<220> FEATURE:
<221> NAME/KEY: MISC_FEATURE
<222> LOCATION: (16)..(16)
<223> OTHER INFORMATION: wherein x at position 16 is attached to
      polyethylene glycol

<400> SEQUENCE: 15

Asn Asp Glu Cys Glu Leu Cys Val Asn Val Ala Cys Thr Gly Cys Xaa
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x at position 1 is attached to
      polyethylene glycol
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (16)..(16)
<223> OTHER INFORMATION: wherein x is a D-LEU
<220> FEATURE:
<221> NAME/KEY: MISC_FEATURE
<222> LOCATION: (16)..(16)
<223> OTHER INFORMATION: wherein x at position 16 is attached to
      polyethylene glycol

<400> SEQUENCE: 16

Xaa Asp Glu Cys Glu Leu Cys Val Asn Val Ala Cys Thr Gly Cys Xaa
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x at position 1 is attached to
      polyethylene glycol
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (2)..(2)
<223> OTHER INFORMATION: wherein x is a D-ASP
<220> FEATURE:
<221> NAME/KEY: MISC_FEATURE
<222> LOCATION: (16)..(16)
<223> OTHER INFORMATION: wherein x is a D-LEU
<220> FEATURE:
<221> NAME/KEY: MISC_FEATURE
```

-continued

```
<222> LOCATION: (16)..(16)
<223> OTHER INFORMATION: wherein x at position 16 is attached to
      polyethylene glycol

<400> SEQUENCE: 17

Xaa Xaa Glu Cys Glu Leu Cys Val Asn Val Ala Cys Thr Gly Cys Xaa
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (16)..(16)
<223> OTHER INFORMATION: wherein x at position 16 is attached to
      polyethylene glycol
<220> FEATURE:
<221> NAME/KEY: MISC_FEATURE
<222> LOCATION: (16)..(16)
<223> OTHER INFORMATION: wherein x is a D-LEU

<400> SEQUENCE: 18

Xaa Asp Glu Cys Glu Leu Cys Val Asn Val Ala Cys Thr Gly Cys Xaa
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (16)..(16)
<223> OTHER INFORMATION: wherein x is a D-LEU

<400> SEQUENCE: 19

Asn Asp Glu Cys Glu Leu Cys Val Asn Val Ala Cys Thr Gly Cys Xaa
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x at position 1 is attached to
      polyethylene glycol
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (16)..(16)
<223> OTHER INFORMATION: wherein x is a D-LEU

<400> SEQUENCE: 20
```

```
Xaa Asp Glu Cys Glu Leu Cys Val Asn Val Ala Cys Thr Gly Cys Xaa
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein x at position 16 is attached to
      polyethylene glycol
<220> FEATURE:
<221> NAME/KEY: MISC_FEATURE
<222> LOCATION: (16)..(16)
<223> OTHER INFORMATION: wherein x is a D-LEU

<400> SEQUENCE: 21

Asn Asp Glu Cys Glu Leu Cys Val Asn Val Ala Cys Thr Gly Cys Xaa
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x at position 1 is attached to
      polyethylene glycol
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (2)..(2)
<223> OTHER INFORMATION: wherein x is a D-ASP
<220> FEATURE:
<221> NAME/KEY: MISC_FEATURE
<222> LOCATION: (3)..(3)
<223> OTHER INFORMATION: wherein x is a D-GLU
<220> FEATURE:
<221> NAME/KEY: MISC_FEATURE
<222> LOCATION: (16)..(16)
<223> OTHER INFORMATION: wherein x is a D-LEU
<220> FEATURE:
<221> NAME/KEY: MISC_FEATURE
<222> LOCATION: (16)..(16)
<223> OTHER INFORMATION: wherein x at position 16 is attached to
      polyethylene glycol

<400> SEQUENCE: 22

Xaa Xaa Xaa Cys Glu Leu Cys Val Asn Val Ala Cys Thr Gly Cys Xaa
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x at position 1 is attached to
      polyethylene glycol
<220> FEATURE:
<221> NAME/KEY: MISC_FEATURE
```

```
<222> LOCATION: (1)..(1)
<223> OTHER INFORMATION: wherein x is a D-ASN
<220> FEATURE:
<221> NAME/KEY: MISC_FEATURE
<222> LOCATION: (2)..(2)
<223> OTHER INFORMATION: wherein x is a D-ASP
<220> FEATURE:
<221> NAME/KEY: MISC_FEATURE
<222> LOCATION: (3)..(3)
<223> OTHER INFORMATION: wherein x is a D-GLU
<220> FEATURE:
<221> NAME/KEY: MISC_FEATURE
<222> LOCATION: (16)..(16)
<223> OTHER INFORMATION: wherein x is a D-LEU

<400> SEQUENCE: 23

Xaa Xaa Xaa Cys Glu Leu Cys Val Asn Val Ala Cys Thr Gly Cys Xaa
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (2)..(2)
<223> OTHER INFORMATION: wherein x is a D-ASP
<220> FEATURE:
<221> NAME/KEY: MISC_FEATURE
<222> LOCATION: (3)..(3)
<223> OTHER INFORMATION: wherein x is a D-GLU
<220> FEATURE:
<221> NAME/KEY: MISC_FEATURE
<222> LOCATION: (16)..(16)
<223> OTHER INFORMATION: wherein x at position 16 is attached to
      polyethylene glycol
<220> FEATURE:
<221> NAME/KEY: MISC_FEATURE
<222> LOCATION: (16)..(16)
<223> OTHER INFORMATION: wherein x is a D-GLU

<400> SEQUENCE: 24

Xaa Xaa Xaa Cys Glu Leu Cys Val Asn Val Ala Cys Thr Gly Cys Xaa
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (2)..(2)
<223> OTHER INFORMATION: wherein x is a D-ASP
<220> FEATURE:
<221> NAME/KEY: MISC_FEATURE
<222> LOCATION: (16)..(16)
<223> OTHER INFORMATION: wherein x at position 16 is attached to
      polyethylene glycol
<220> FEATURE:
<221> NAME/KEY: MISC_FEATURE
<222> LOCATION: (16)..(16)
<223> OTHER INFORMATION: wherein x is a D-LEU
```

-continued

```
<400> SEQUENCE: 25

Xaa Xaa Glu Cys Glu Leu Cys Val Asn Val Ala Cys Thr Gly Cys Xaa
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x at position 1 is attached to
      polyethylene glycol
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (2)..(2)
<223> OTHER INFORMATION: wherein x is a D-ASP
<220> FEATURE:
<221> NAME/KEY: MISC_FEATURE
<222> LOCATION: (16)..(16)
<223> OTHER INFORMATION: wherein x is a D-LEU

<400> SEQUENCE: 26

Xaa Xaa Glu Cys Glu Leu Cys Val Asn Val Ala Cys Thr Gly Cys Xaa
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (16)..(16)
<223> OTHER INFORMATION: wherein x is 3-(2-naphthyl)alanine
<220> FEATURE:
<221> NAME/KEY: MISC_FEATURE
<222> LOCATION: (16)..(16)
<223> OTHER INFORMATION: wherein x is a D-amino acid

<400> SEQUENCE: 27

Xaa Asp Glu Cys Glu Leu Cys Val Asn Val Ala Cys Thr Gly Cys Xaa
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (8)..(8)
<223> OTHER INFORMATION: wherein x at position 8 is alpha-amino
      isobutyric acid
<220> FEATURE:
<221> NAME/KEY: MISC_FEATURE
<222> LOCATION: (10)..(10)
```

<223> OTHER INFORMATION: wherein x at position 10 is alpha-amino
      isobutyric acid
<220> FEATURE:
<221> NAME/KEY: MISC_FEATURE
<222> LOCATION: (16)..(16)
<223> OTHER INFORMATION: wherein x is a D-LEU

<400> SEQUENCE: 28

Xaa Asp Glu Cys Glu Leu Cys Xaa Asn Xaa Ala Cys Thr Gly Cys Xaa
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (7)..(7)
<223> OTHER INFORMATION: wherein ASP at position 7 is attached to a
      Lactam bridge
<220> FEATURE:
<221> NAME/KEY: MISC_FEATURE
<222> LOCATION: (15)..(15)
<223> OTHER INFORMATION: wherein x at position 15 is ornithine
<220> FEATURE:
<221> NAME/KEY: MISC_FEATURE
<222> LOCATION: (16)..(16)
<223> OTHER INFORMATION: wherein x is a D-LEU

<400> SEQUENCE: 29

Xaa Asp Glu Cys Glu Leu Asp Val Asn Val Ala Cys Thr Gly Xaa Xaa
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (16)..(16)
<223> OTHER INFORMATION: wherein x is a D-LEU

<400> SEQUENCE: 30

Xaa Asp Glu Cys Glu Tyr Cys Val Asn Val Ala Cys Thr Gly Cys Xaa
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (16)..(16)
<223> OTHER INFORMATION: wherein x is a D-LEU

```
<400> SEQUENCE: 31

Xaa Asp Glu Cys Glu Ser Cys Val Asn Val Ala Cys Thr Gly Cys Xaa
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x at position 1 is attached to
      polyethylene glycol
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (16)..(16)
<223> OTHER INFORMATION: wherein x is a D-LEU
<220> FEATURE:
<221> NAME/KEY: MISC_FEATURE
<222> LOCATION: (16)..(16)
<223> OTHER INFORMATION: wherein x at position 16 is attached to
      polyethylene glycol

<400> SEQUENCE: 32

Xaa Asp Glu Cys Glu Tyr Cys Val Asn Val Ala Cys Thr Gly Cys Xaa
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x at position 1 is attached to
      polyethylene glycol
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (16)..(16)
<223> OTHER INFORMATION: wherein x is a D-LEU

<400> SEQUENCE: 33

Xaa Asp Glu Cys Glu Tyr Cys Val Asn Val Ala Cys Thr Gly Cys Xaa
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (16)..(16)
<223> OTHER INFORMATION: wherein x at position 16 is attached to
      polyethylene glycol
<220> FEATURE:
```

```
<221> NAME/KEY: MISC_FEATURE
<222> LOCATION: (16)..(16)
<223> OTHER INFORMATION: wherein x is a D-LEU

<400> SEQUENCE: 34

Xaa Asp Glu Cys Glu Tyr Cys Val Asn Val Ala Cys Thr Gly Cys Xaa
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x at position 1 is attached to
      polyethylene glycol
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (16)..(16)
<223> OTHER INFORMATION: wherein x is a D-LEU
<220> FEATURE:
<221> NAME/KEY: MISC_FEATURE
<222> LOCATION: (16)..(16)
<223> OTHER INFORMATION: wherein x at position 16 is attached to
      polyethylene glycol

<400> SEQUENCE: 35

Xaa Asp Glu Cys Glu Ser Cys Val Asn Val Ala Cys Thr Gly Cys Xaa
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x at position 1 is attached to
      polyethylene glycol
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (16)..(16)
<223> OTHER INFORMATION: wherein x is a D-LEU

<400> SEQUENCE: 36

Xaa Asp Glu Cys Glu Ser Cys Val Asn Val Ala Cys Thr Gly Cys Xaa
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
```

```
<222> LOCATION: (16)..(16)
<223> OTHER INFORMATION: wherein x at position 16 is attached to
      polyethylene glycol
<220> FEATURE:
<221> NAME/KEY: MISC_FEATURE
<222> LOCATION: (16)..(16)
<223> OTHER INFORMATION: wherein x is a D-LEU

<400> SEQUENCE: 37

Xaa Asp Glu Cys Glu Ser Cys Val Asn Val Ala Cys Thr Gly Cys Xaa
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 38

Asn Asp Glu Cys Glu Leu Cys Val Asn Val Ala Cys Thr Gly Cys Ser
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (16)..(16)
<223> OTHER INFORMATION: wherein SER at position 16 is attached to
      polyethylene glycol

<400> SEQUENCE: 39

Asn Asp Glu Cys Glu Leu Cys Val Asn Val Ala Cys Thr Gly Cys Ser
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol

<400> SEQUENCE: 40

Asn Asp Glu Cys Glu Leu Cys Val Asn Val Ala Cys Thr Gly Cys Ser
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein SER at position 16 is attached to
      polyethylene glycol
```

```
<400> SEQUENCE: 41

Asn Asp Glu Cys Glu Leu Cys Val Asn Val Ala Cys Thr Gly Cys Ser
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (16)..(16)
<223> OTHER INFORMATION: wherein x is a D-SER
<220> FEATURE:
<221> NAME/KEY: MISC_FEATURE
<222> LOCATION: (16)..(16)
<223> OTHER INFORMATION: wherein x at position 16 is attached to
      polyethylene glycol

<400> SEQUENCE: 42

Asn Asp Glu Cys Glu Leu Cys Val Asn Val Ala Cys Thr Gly Cys Xaa
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (16)..(16)
<223> OTHER INFORMATION: wherein x is a D-SER

<400> SEQUENCE: 43

Asn Asp Glu Cys Glu Leu Cys Val Asn Val Ala Cys Thr Gly Cys Xaa
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein x at position 16 is attached to
      polyethylene glycol
<220> FEATURE:
<221> NAME/KEY: MISC_FEATURE
<222> LOCATION: (16)..(16)
<223> OTHER INFORMATION: wherein x is a D-SER

<400> SEQUENCE: 44

Asn Asp Glu Cys Glu Leu Cys Val Asn Val Ala Cys Thr Gly Cys Xaa
1               5                   10                  15

<210> SEQ ID NO 45
```

```
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (5)..(6)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (8)..(11)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (13)..(14)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (16)..(16)
<223> OTHER INFORMATION: wherein x is any natural, unnatural amino acid
      or amino acid analogue and may be an L-amino acid, a D-amino acid,
      a methylated amino acid or any combination of thereof

<400> SEQUENCE: 45

Asn Asp Glu Cys Xaa Xaa Cys Xaa Xaa Xaa Xaa Cys Xaa Xaa Cys Xaa
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(3)
<223> OTHER INFORMATION: wherein x is any natural, unnatural amino acid
      or amino acid analogue that is one, two or three residues in
      length and may be an L-amino acid, a D-amino acid, a methylated
      amino acid or any combination of thereof
<220> FEATURE:
<221> NAME/KEY: MISC_FEATURE
<222> LOCATION: (5)..(6)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (8)..(11)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (13)..(14)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (16)..(16)
<223> OTHER INFORMATION: wherein x is any natural, unnatural amino acid
      or amino acid analogue that is zero or one residue in length and
      may be an L-amino acid, a D-amino acid, a methylated amino acid or
      any combination of thereof

<400> SEQUENCE: 46

Xaa Xaa Xaa Cys Xaa Xaa Cys Xaa Xaa Xaa Xaa Cys Xaa Xaa Cys Xaa
1               5                   10                  15
```

```
<210> SEQ ID NO 47
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(3)
<223> OTHER INFORMATION: wherein x is any natural, unnatural amino acid
      or amino acid analogue that is one, two or three residues in
      length and may be an L-amino acid, a D-amino acid, a methylated
      amino acid or any combination of thereof
<220> FEATURE:
<221> NAME/KEY: MISC_FEATURE
<222> LOCATION: (4)..(4)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (6)..(6)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (7)..(7)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (12)..(12)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (15)..(15)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (16)..(16)
<223> OTHER INFORMATION: wherein x is any natural, unnatural amino
      acid or amino acid analogue that is zero or one residue in
      length and may be an L-amino acid, a D-amino acid, a methylated
      amino acid or any combination of thereof

<400> SEQUENCE: 47

Xaa Xaa Xaa Xaa Glu Xaa Xaa Val Asn Val Ala Xaa Thr Gly Xaa Xaa
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(3)
<223> OTHER INFORMATION: wherein x is any natural, unnatural amino acid
      or amino acid analogue that is one, two or three residues in
      length and may be an L-amino acid, a D-amino acid, a methylated
      amino acid or any combination of thereof
<220> FEATURE:
<221> NAME/KEY: MISC_FEATURE
<222> LOCATION: (4)..(4)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (5)..(6)
<223> OTHER INFORMATION: wherein x is any natural, unnatural amino acid
      or amino acid analogue and may be an L-amino acid, a D-amino acid,
      a methylated amino acid or any combination of thereof
```

```
<220> FEATURE:
<221> NAME/KEY: MISC_FEATURE
<222> LOCATION: (7)..(7)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (8)..(11)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (12)..(12)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (13)..(14)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (15)..(15)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (16)..(16)
<223> OTHER INFORMATION: wherein x is any natural, unnatural amino acid
      or amino acid analogue that is zero or one residue in length and
      may be an L-amino acid, a D-amino acid, a methylated amino acid
      or any combination of thereof

<400> SEQUENCE: 48

Xaa Xaa Xaa Xaa Xaa Xaa Xaa Xaa Xaa Xaa Xaa Xaa Xaa Xaa Xaa Xaa
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (5)..(6)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (8)..(8)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (10)..(11)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (13)..(14)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (16)..(16)
<223> OTHER INFORMATION: wherein x is any natural, unnatural amino acid
      or amino acid analogue and may be an L-amino acid, a D-amino acid,
      a methylated amino acid or any combination of thereof

<400> SEQUENCE: 49
```

Asn Asp Asp Cys Xaa Xaa Cys Xaa Asn Xaa Xaa Cys Xaa Xaa Cys Xaa
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (5)..(6)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (8)..(8)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (10)..(11)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (13)..(14)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (16)..(16)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (16)..(16)
<223> OTHER INFORMATION: wherein x is a D-amino acid

<400> SEQUENCE: 50

Xaa Glu Glu Cys Xaa Xaa Cys Xaa Asn Xaa Xaa Cys Xaa Xaa Cys Xaa
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (2)..(2)
<223> OTHER INFORMATION: wherein x is a D-GLU
<220> FEATURE:
<221> NAME/KEY: MISC_FEATURE
<222> LOCATION: (5)..(6)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (8)..(8)

```
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (10)..(11)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (13)..(14)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (16)..(16)
<223> OTHER INFORMATION: wherein x is a D-amino acid
<220> FEATURE:
<221> NAME/KEY: MISC_FEATURE
<222> LOCATION: (16)..(16)
<223> OTHER INFORMATION: wherein x is any natural, unnatural amino acid
      or amino acid analogue and may be an L-amino acid, a D-amino acid,
      a methylated amino acid or any combination of thereof

<400> SEQUENCE: 51

Xaa Xaa Asp Cys Xaa Xaa Cys Xaa Asn Xaa Xaa Cys Xaa Xaa Cys Xaa
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (2)..(2)
<223> OTHER INFORMATION: wherein x is a D-ASP
<220> FEATURE:
<221> NAME/KEY: MISC_FEATURE
<222> LOCATION: (5)..(6)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (8)..(8)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (10)..(11)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (13)..(14)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (16)..(16)
<223> OTHER INFORMATION: wherein x is a D-amino acid
<220> FEATURE:
<221> NAME/KEY: MISC_FEATURE
<222> LOCATION: (16)..(16)
<223> OTHER INFORMATION: wherein x is any natural, unnatural amino acid
      or amino acid analogue and may be an L-amino acid, a D-amino acid,
``` a methylated amino acid or any combination of thereof

<400> SEQUENCE: 52

Xaa Xaa Glu Cys Xaa Xaa Cys Xaa Asn Xaa Xaa Cys Xaa Xaa Cys Xaa
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (2)..(2)
<223> OTHER INFORMATION: wherein x is a D-ASP
<220> FEATURE:
<221> NAME/KEY: MISC_FEATURE
<222> LOCATION: (3)..(3)
<223> OTHER INFORMATION: wherein x is a D-GLU
<220> FEATURE:
<221> NAME/KEY: MISC_FEATURE
<222> LOCATION: (5)..(6)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (8)..(8)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (10)..(11)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (13)..(14)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (16)..(16)
<223> OTHER INFORMATION: wherein x is a D-amino acid
<220> FEATURE:
<221> NAME/KEY: MISC_FEATURE
<222> LOCATION: (16)..(16)
<223> OTHER INFORMATION: wherein x is any natural, unnatural amino acid
      or amino acid analogue and may be an L-amino acid, a D-amino acid,
      a methylated amino acid or any combination of thereof

<400> SEQUENCE: 53

Xaa Xaa Xaa Cys Xaa Xaa Cys Xaa Tyr Xaa Xaa Cys Xaa Xaa Cys Xaa
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE

```
<222> LOCATION: (2)..(2)
<223> OTHER INFORMATION: wherein x is a D-GLU
<220> FEATURE:
<221> NAME/KEY: MISC_FEATURE
<222> LOCATION: (3)..(3)
<223> OTHER INFORMATION: wherein x is a D-GLU
<220> FEATURE:
<221> NAME/KEY: MISC_FEATURE
<222> LOCATION: (5)..(6)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (8)..(8)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (10)..(11)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (13)..(14)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (16)..(16)
<223> OTHER INFORMATION: wherein x is a D-amino acid
<220> FEATURE:
<221> NAME/KEY: MISC_FEATURE
<222> LOCATION: (16)..(16)
<223> OTHER INFORMATION: wherein x is any natural, unnatural amino acid
      or amino acid analogue and may be an L-amino acid, a D-amino acid,
      a methylated amino acid or any combination of thereof

<400> SEQUENCE: 54

Xaa Xaa Xaa Cys Xaa Xaa Cys Xaa Tyr Xaa Xaa Cys Xaa Xaa Cys Xaa
1               5                   10                  15

<210> SEQ ID NO 55
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 55

Cys Cys Glu Tyr Cys Cys Asn Pro Ala Cys Thr Gly Cys Tyr
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 56

Cys Cys Glu Tyr Cys Cys Asn Pro Ala Cys Thr Gly Cys
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Chemically Synthesized
```

```
<220> FEATURE:
<221> NAME/KEY: MISC_FEATURE
<222> LOCATION: (1)..(1)
<223> OTHER INFORMATION: wherein CYS at position 1 is attached to
      polyethylene glycol
<220> FEATURE:
<221> NAME/KEY: MISC_FEATURE
<222> LOCATION: (14)..(14)
<223> OTHER INFORMATION: wherein TYR at position 14 is attached to
      polyethylene glycol

<400> SEQUENCE: 57

Cys Cys Glu Tyr Cys Cys Asn Pro Ala Cys Thr Gly Cys Tyr
1               5                   10

<210> SEQ ID NO 58
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 58

Asn Phe Cys Cys Glu Ser Cys Cys Asn Pro Ala Cys Thr Gly Cys Tyr
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 59

Asn Phe Cys Cys Glu Phe Cys Cys Asn Pro Ala Cys Thr Gly Cys Tyr
1               5                   10                  15

<210> SEQ ID NO 60
<211> LENGTH: 14
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (14)..(14)
<223> OTHER INFORMATION: wherein x is a D-TYR

<400> SEQUENCE: 60

Cys Cys Glu Tyr Cys Cys Asn Pro Ala Cys Thr Gly Cys Xaa
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein CYS at position 1 is attached to
      polyethylene glycol

<400> SEQUENCE: 61

Cys Cys Glu Tyr Cys Cys Asn Pro Ala Cys Thr Gly Cys Tyr
1               5                   10

<210> SEQ ID NO 62
```

```
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 62

Asn Phe Cys Cys Glu Thr Cys Cys Asn Pro Ala Cys Thr Gly Cys Tyr
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein x is a D-TYR

<400> SEQUENCE: 63

Asn Phe Cys Cys Glu Ser Cys Cys Asn Pro Ala Cys Thr Gly Cys Xaa
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is a D-ASN

<400> SEQUENCE: 64

Xaa Phe Cys Cys Glu Ser Cys Cys Asn Pro Ala Cys Thr Gly Cys Tyr
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (16)..(16)
<223> OTHER INFORMATION: wherein x is a D-TYR

<400> SEQUENCE: 65

Xaa Phe Cys Cys Glu Ser Cys Cys Asn Pro Ala Cys Thr Gly Cys Xaa
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein x is a D-TYR

<400> SEQUENCE: 66
```

```
Asn Phe Cys Cys Glu Thr Cys Cys Asn Pro Ala Cys Thr Gly Cys Xaa
1               5                   10                  15
```

<210> SEQ ID NO 67
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is a D-ASN

<400> SEQUENCE: 67

```
Xaa Phe Cys Cys Glu Thr Cys Cys Asn Pro Ala Cys Thr Gly Cys Tyr
1               5                   10                  15
```

<210> SEQ ID NO 68
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (16)..(16)
<223> OTHER INFORMATION: wherein x is a D-TYR

<400> SEQUENCE: 68

```
Xaa Phe Cys Cys Glu Thr Cys Cys Asn Pro Ala Cys Thr Gly Cys Xaa
1               5                   10                  15
```

<210> SEQ ID NO 69
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein x is a D-TYR

<400> SEQUENCE: 69

```
Asn Phe Cys Cys Glu Phe Cys Cys Asn Pro Ala Cys Thr Gly Cys Xaa
1               5                   10                  15
```

<210> SEQ ID NO 70
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is a D-ASN

<400> SEQUENCE: 70

```
Xaa Phe Cys Cys Glu Phe Cys Cys Asn Pro Ala Cys Thr Gly Cys Tyr
1               5                   10                  15
```

<210> SEQ ID NO 71
<211> LENGTH: 16

```
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is a D-ASN
<220> FEATURE:
<221> NAME/KEY: MISC_FEATURE
<222> LOCATION: (16)..(16)
<223> OTHER INFORMATION: wherein x is a D-TYR

<400> SEQUENCE: 71

Xaa Phe Cys Cys Glu Phe Cys Cys Asn Pro Ala Cys Thr Gly Cys Xaa
1               5                   10                  15

<210> SEQ ID NO 72
<211> LENGTH: 14
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (14)..(14)
<223> OTHER INFORMATION: wherein TYR at position 14 is attached to
      polyethylene glycol

<400> SEQUENCE: 72

Cys Cys Glu Tyr Cys Cys Asn Pro Ala Cys Thr Gly Cys Tyr
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein CYS at position 1 is attached to
      polyethylene glycol
<220> FEATURE:
<221> NAME/KEY: MISC_FEATURE
<222> LOCATION: (13)..(13)
<223> OTHER INFORMATION: wherein CYS at position 13 is attached to
      polyethylene glycol

<400> SEQUENCE: 73

Cys Cys Glu Tyr Cys Cys Asn Pro Ala Cys Thr Gly Cys
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein CYS at position 1 is attached to
      polyethylene glycol

<400> SEQUENCE: 74

Cys Cys Glu Tyr Cys Cys Asn Pro Ala Cys Thr Gly Cys
1               5                   10

<210> SEQ ID NO 75
```

```
<211> LENGTH: 13
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (13)..(13)
<223> OTHER INFORMATION: wherein CYS at position 13 is attached to
      polyethylene glycol

<400> SEQUENCE: 75

Cys Cys Glu Tyr Cys Cys Asn Pro Ala Cys Thr Gly Cys
1               5                   10

<210> SEQ ID NO 76
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (16)..(16)
<223> OTHER INFORMATION: wherein TYR at position 16 is attached to
      polyethylene glycol

<400> SEQUENCE: 76

Asn Phe Cys Cys Glu Ser Cys Cys Asn Pro Ala Cys Thr Gly Cys Tyr
1               5                   10                  15

<210> SEQ ID NO 77
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol

<400> SEQUENCE: 77

Asn Phe Cys Cys Glu Ser Cys Cys Asn Pro Ala Cys Thr Gly Cys Tyr
1               5                   10                  15

<210> SEQ ID NO 78
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein TYR at position 16 is attached to
      polyethylene glycol

<400> SEQUENCE: 78

Asn Phe Cys Cys Glu Ser Cys Cys Asn Pro Ala Cys Thr Gly Cys Tyr
1               5                   10                  15

<210> SEQ ID NO 79
<211> LENGTH: 16
<212> TYPE: PRT
```

```
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (16)..(16)
<223> OTHER INFORMATION: wherein TYR at position 16 is attached to
      polyethylene glycol

<400> SEQUENCE: 79

Asn Phe Cys Cys Glu Phe Cys Cys Asn Pro Ala Cys Thr Gly Cys Tyr
1               5                   10                  15

<210> SEQ ID NO 80
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol

<400> SEQUENCE: 80

Asn Phe Cys Cys Glu Phe Cys Cys Asn Pro Ala Cys Thr Gly Cys Tyr
1               5                   10                  15

<210> SEQ ID NO 81
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein TYR at position 16 is attached to
      polyethylene glycol

<400> SEQUENCE: 81

Asn Phe Cys Cys Glu Phe Cys Cys Asn Pro Ala Cys Thr Gly Cys Tyr
1               5                   10                  15

<210> SEQ ID NO 82
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (16)..(16)
<223> OTHER INFORMATION: wherein TYR at position 16 is attached to
      polyethylene glycol

<400> SEQUENCE: 82

Asn Phe Cys Cys Glu Tyr Cys Cys Asn Pro Ala Cys Thr Gly Cys Tyr
1               5                   10                  15
```

<210> SEQ ID NO 83
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
       polyethylene glycol

<400> SEQUENCE: 83

Asn Phe Cys Cys Glu Tyr Cys Cys Asn Pro Ala Cys Thr Gly Cys Tyr
1               5                   10                  15

<210> SEQ ID NO 84
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein TYR at position 16 is attached to
       polyethylene glycol

<400> SEQUENCE: 84

Asn Phe Cys Cys Glu Tyr Cys Cys Asn Pro Ala Cys Thr Gly Cys Tyr
1               5                   10                  15

<210> SEQ ID NO 85
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 85

Cys Cys Glu Ser Cys Cys Asn Pro Ala Cys Thr Gly Cys Tyr
1               5                   10

<210> SEQ ID NO 86
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 86

Cys Cys Glu Phe Cys Cys Asn Pro Ala Cys Thr Gly Cys Tyr
1               5                   10

<210> SEQ ID NO 87
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 87

Cys Cys Glu Ser Cys Cys Asn Pro Ala Cys Thr Gly Cys
1               5                   10

<210> SEQ ID NO 88
<211> LENGTH: 13
<212> TYPE: PRT
<213> ORGANISM: Artificial Sequence

```
<220> FEATURE:
<223> OTHER INFORMATION: Chemically Synthesized

<400> SEQUENCE: 88

Cys Cys Glu Phe Cys Cys Asn Pro Ala Cys Thr Gly Cys
1               5                   10

<210> SEQ ID NO 89
<211> LENGTH: 14
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(2)
<223> OTHER INFORMATION: wherein x is penicillamine
<220> FEATURE:
<221> NAME/KEY: MISC_FEATURE
<222> LOCATION: (5)..(6)
<223> OTHER INFORMATION: wherein x is penicillamine
<220> FEATURE:
<221> NAME/KEY: MISC_FEATURE
<222> LOCATION: (10)..(10)
<223> OTHER INFORMATION: wherein x is penicillamine
<220> FEATURE:
<221> NAME/KEY: MISC_FEATURE
<222> LOCATION: (13)..(13)
<223> OTHER INFORMATION: wherein x is penicillamine

<400> SEQUENCE: 89

Xaa Xaa Glu Tyr Xaa Xaa Asn Pro Ala Xaa Thr Gly Xaa Tyr
1               5                   10

<210> SEQ ID NO 90
<211> LENGTH: 13
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(2)
<223> OTHER INFORMATION: wherein x is penicillamine
<220> FEATURE:
<221> NAME/KEY: MISC_FEATURE
<222> LOCATION: (5)..(6)
<223> OTHER INFORMATION: wherein x is penicillamine
<220> FEATURE:
<221> NAME/KEY: MISC_FEATURE
<222> LOCATION: (10)..(10)
<223> OTHER INFORMATION: wherein x is penicillamine
<220> FEATURE:
<221> NAME/KEY: MISC_FEATURE
<222> LOCATION: (13)..(13)
<223> OTHER INFORMATION: wherein x is penicillamine

<400> SEQUENCE: 90

Xaa Xaa Glu Tyr Xaa Xaa Asn Pro Ala Xaa Thr Gly Xaa
1               5                   10

<210> SEQ ID NO 91
<211> LENGTH: 22
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(6)
<223> OTHER INFORMATION: wherein x is any natural, unnatural amino acid
      or amino acid analogue and may be an L-amino acid, a D-amino acid,
      a methylated amino acid or any combination of thereof
```

```
<220> FEATURE:
<221> NAME/KEY: MISC_FEATURE
<222> LOCATION: (11)..(11)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (15)..(17)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (19)..(20)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (22)..(22)
<223> OTHER INFORMATION: wherein x is any natural, unnatural amino acid
      or amino acid analogue and may be an L-amino acid, a D-amino acid,
      a methylated amino acid or any combination of thereof

<400> SEQUENCE: 91

Xaa Xaa Xaa Xaa Xaa Xaa Asn Tyr Cys Cys Xaa Tyr Cys Cys Xaa Xaa
1               5                   10                  15

Xaa Cys Xaa Xaa Cys Xaa
            20

<210> SEQ ID NO 92
<211> LENGTH: 22
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(6)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (11)..(11)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (15)..(17)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (19)..(20)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (22)..(22)
<223> OTHER INFORMATION: wherein x is any natural, unnatural amino acid
      or amino acid analogue and may be an L-amino acid, a D-amino acid,
      a methylated amino acid or any combination of thereof

<400> SEQUENCE: 92

Xaa Xaa Xaa Xaa Xaa Xaa Asn Phe Cys Cys Xaa Phe Cys Cys Xaa Xaa
1               5                   10                  15

Xaa Cys Xaa Xaa Cys Xaa
            20
```

```
<210> SEQ ID NO 93
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (5)..(5)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (9)..(11)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (13)..(14)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (16)..(16)
<223> OTHER INFORMATION: wherein x is any natural, unnatural amino acid
      or amino acid analogue and may be an L-amino acid, a D-amino acid,
      a methylated amino acid or any combination of thereof

<400> SEQUENCE: 93

Asn Phe Cys Cys Xaa Phe Cys Cys Xaa Xaa Xaa Cys Xaa Xaa Cys Xaa
1               5                   10                  15

<210> SEQ ID NO 94
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (3)..(3)
<223> OTHER INFORMATION: wherein x is penicillamine
<220> FEATURE:
<221> NAME/KEY: MISC_FEATURE
<222> LOCATION: (5)..(5)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (8)..(8)
<223> OTHER INFORMATION: wherein x is penicillamine
<220> FEATURE:
<221> NAME/KEY: MISC_FEATURE
<222> LOCATION: (9)..(11)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (13)..(14)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (16)..(16)
<223> OTHER INFORMATION: wherein x is any natural, unnatural amino acid
      or amino acid analogue and may be an L-amino acid, a D-amino acid,
      a methylated amino acid or any combination of thereof

<400> SEQUENCE: 94
```

```
Asn Phe Xaa Cys Xaa Phe Cys Xaa Xaa Xaa Xaa Cys Xaa Xaa Cys Xaa
1               5                   10                  15
```

<210> SEQ ID NO 95
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (3)..(4)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (5)..(6)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (7)..(8)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (9)..(11)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (12)..(12)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (13)..(14)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (15)..(15)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (16)..(16)
<223> OTHER INFORMATION: wherein x is any natural, unnatural amino acid
      or amino acid analogue and may be an L-amino acid, a D-amino acid,
      a methylated amino acid or any combination of thereof

<400> SEQUENCE: 95

```
Asn Phe Xaa Xaa Xaa Xaa Xaa Xaa Xaa Xaa Xaa Xaa Xaa Xaa Xaa Xaa
1               5                   10                  15
```

<210> SEQ ID NO 96
<211> LENGTH: 14
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(2)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (4)..(4)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:

```
<221> NAME/KEY: MISC_FEATURE
<222> LOCATION: (5)..(6)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (10)..(10)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (13)..(13)
<223> OTHER INFORMATION: wherein x is a cysteine, penicillamine
      homocysteine, or 3-mercaptoproline

<400> SEQUENCE: 96

Xaa Xaa Glu Xaa Xaa Xaa Asn Pro Ala Xaa Thr Gly Xaa Tyr
1               5                   10

<210> SEQ ID NO 97
<211> LENGTH: 13
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(2)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (4)..(4)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (5)..(6)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (10)..(10)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (13)..(13)
<223> OTHER INFORMATION: wherein x is a cysteine, penicillamine
      homocysteine, or 3-mercaptoproline

<400> SEQUENCE: 97

Xaa Xaa Glu Xaa Xaa Xaa Asn Pro Ala Xaa Thr Gly Xaa
1               5                   10

<210> SEQ ID NO 98
<211> LENGTH: 20
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(6)
<223> OTHER INFORMATION: wherein x is any natural, unnatural amino acid
      or amino acid analogue that is zero, one, two, three, four, five
      or six residues in length and may be an L-amino acid, a D-amino
      acid, a methylated amino acid or any combination of thereof
<220> FEATURE:
<221> NAME/KEY: MISC_FEATURE
<222> LOCATION: (7)..(8)
<223> OTHER INFORMATION: wherein x is a cysteine, penicillamine
      homocysteine, or 3-mercaptoproline
<220> FEATURE:
```

```
<221> NAME/KEY: MISC_FEATURE
<222> LOCATION: (9)..(10)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (11)..(12)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (13)..(15)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (16)..(16)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (17)..(18)
<223> OTHER INFORMATION: wherein x is any natural, unnatural amino acid
      or amino acid analogue and may be an L-amino acid, a D-amino acid,
      a methylated amino acid or any combination of thereof
<220> FEATURE:
<221> NAME/KEY: MISC_FEATURE
<222> LOCATION: (19)..(19)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (20)..(20)
<223> OTHER INFORMATION: wherein x is any natural, unnatural amino acid
      or amino acid analogue that is zero or one residue in length and
      may be an L-amino acid, a D-amino acid, a methylated amino acid or
      any combination of thereof

<400> SEQUENCE: 98

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 99
<211> LENGTH: 5
<212> TYPE: PRT
<213> ORGANISM: Artificial Sequence
<220> FEATURE:
<223> OTHER INFORMATION: Chemically Synthesized

<400> SEQUENCE: 99

Gln His Asn Pro Arg
1               5

<210> SEQ ID NO 100
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 100

Val Gln His Asn Pro Arg
1               5

<210> SEQ ID NO 101
<211> LENGTH: 7
<212> TYPE: PRT
<213> ORGANISM: Artificial Sequence
```

```
<220> FEATURE:
<223> OTHER INFORMATION: Chemically Synthesized

<400> SEQUENCE: 101

Val Arg Gln His Asn Pro Arg
1               5

<210> SEQ ID NO 102
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 102

Val Arg Gly Gln His Asn Pro Arg
1               5

<210> SEQ ID NO 103
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 103

Val Arg Gly Pro Gln His Asn Pro Arg
1               5

<210> SEQ ID NO 104
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 104

Val Arg Gly Pro Arg Gln His Asn Pro Arg
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 105

Val Arg Gly Pro Arg Arg Gln His Asn Pro Arg
1               5                   10

<210> SEQ ID NO 106
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 106

Arg Gln His Asn Pro Arg
1               5

<210> SEQ ID NO 107
<211> LENGTH: 34
<212> TYPE: PRT
<213> ORGANISM: Artificial Sequence
<220> FEATURE:
```

<223> OTHER INFORMATION: Chemically Synthesized

<400> SEQUENCE: 107

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 108
<211> LENGTH: 27
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein HIS at position 1 is attached to an
      R-NH-, wherein R is a hydrogen or organic compound having from 1
      to 10 carbon atoms
<220> FEATURE:
<221> NAME/KEY: MISC_FEATURE
<222> LOCATION: (27)..(27)
<223> OTHER INFORMATION: wherein LYS at position 27 is attached to CONH2

<400> SEQUENCE: 108

His Ala Glu Gly Thr Phe Thr Ser Asp Val Ser Tyr Leu Glu Gly Gln
1               5                   10                  15

Ala Ala Lys Glu Phe Ile Ala Trp Leu Val Lys
            20                  25

<210> SEQ ID NO 109
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 109

Lys Tyr Tyr Arg Trp Arg
1               5

<210> SEQ ID NO 110
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 110

Arg Tyr Tyr Arg Trp Arg
1               5

<210> SEQ ID NO 111
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 111

Lys Trp Arg Tyr Tyr Arg
1               5

<210> SEQ ID NO 112

```
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 112

Arg Tyr Tyr Arg Trp Lys
1               5

<210> SEQ ID NO 113
<211> LENGTH: 6
<212> TYPE: PRT
<213> ORGANISM: Artificial Sequence
<220> FEATURE:
<223> OTHER INFORMATION: Chemically Synthesized
<220> FEATURE:
<221> NAME/KEY: x
<222> LOCATION: (1)..(1)
<223> OTHER INFORMATION: wherein x is a D-ARG
<220> FEATURE:
<221> NAME/KEY: x
<222> LOCATION: (2)..(3)
<223> OTHER INFORMATION: wherein x is a D-TYR
<220> FEATURE:
<221> NAME/KEY: x
<222> LOCATION: (4)..(4)
<223> OTHER INFORMATION: wherein x is a D-ARG
<220> FEATURE:
<221> NAME/KEY: x
<222> LOCATION: (5)..(5)
<223> OTHER INFORMATION: wherein x is a D-TRP
<220> FEATURE:
<221> NAME/KEY: x
<222> LOCATION: (6)..(6)
<223> OTHER INFORMATION: wherein x is a D-LYS

<400> SEQUENCE: 113

Xaa Xaa Xaa Xaa Xaa Xaa
1               5

<210> SEQ ID NO 114
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 114

Arg Tyr Tyr Arg Ile Lys
1               5

<210> SEQ ID NO 115
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 115

Arg Tyr Tyr Arg Ile Arg
1               5

<210> SEQ ID NO 116
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 116
```

Arg Tyr Tyr Lys Ile Lys
1               5

<210> SEQ ID NO 117
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 117

Arg Tyr Tyr Lys Ile Arg
1               5

<210> SEQ ID NO 118
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 118

Arg Tyr Tyr Lys Trp Arg
1               5

<210> SEQ ID NO 119
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 119

Arg Tyr Tyr Lys Trp Lys
1               5

<210> SEQ ID NO 120
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 120

Arg Tyr Tyr Arg Trp Arg
1               5

<210> SEQ ID NO 121
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 121

Lys Tyr Tyr Arg Trp Lys
1               5

<210> SEQ ID NO 122
<211> LENGTH: 5
<212> TYPE: PRT
<213> ORGANISM: Artificial Sequence
<220> FEATURE:
<223> OTHER INFORMATION: Enkephalin pentapeptide
<220> FEATURE:
<221> NAME/KEY: MISC_FEATURE
<222> LOCATION: (2)..(2)

```
<223> OTHER INFORMATION: wherein the Xaa is a D-Lys
<220> FEATURE:
<221> NAME/KEY: MISC_FEATURE
<222> LOCATION: (5)..(5)
<223> OTHER INFORMATION: wherein the Xaa is an L-homoserine

<400> SEQUENCE: 122

Tyr Xaa Gly Phe Xaa
1               5

<210> SEQ ID NO 123
<211> LENGTH: 4
<212> TYPE: PRT
<213> ORGANISM: Artificial Sequence
<220> FEATURE:
<223> OTHER INFORMATION: frakefamide
<220> FEATURE:
<221> NAME/KEY: MISC_FEATURE
<222> LOCATION: (2)..(2)
<223> OTHER INFORMATION: wherein the Xaa is a D-Ala
<220> FEATURE:
<221> NAME/KEY: MISC_FEATURE
<222> LOCATION: (4)..(4)
<223> OTHER INFORMATION: wherein the Phe is aminated

<400> SEQUENCE: 123

Tyr Xaa Phe Phe
1
```

AGONISTS OF GUANYLATE CYCLASE USEFUL FOR THE TREATMENT OF GASTROINTESTINAL DISORDERS, INFLAMMATION, CANCER AND OTHER DISORDERS

RELATED APPLICATIONS

This application is a continuation application of U.S. application Ser. No. 13/010,267 filed on Jan. 20, 2011, which is a continuation application of U.S. application Ser. No. 12/133,344, now U.S. Pat. No. 7,879,802, filed on Jun. 4, 2008, which claims the benefit of priority to U.S. Provisional Application No. 60/933,194 filed on Jun. 4, 2007, the contents of each of which are incorporated by reference in their entireties.

INCORPORATION-BY-REFERENCE OF SEQUENCE LISTING

The contents of the text file named "40737-503C02US_ST25", which was created on Apr. 3, 2013 and is 67 KB in size, are hereby incorporated by reference in their entireties.

FIELD OF THE INVENTION

The present invention relates to the therapeutic use of guanylate cyclase C (GC-C) agonists as a means for enhancing the intracellular production of cGMP. The agonists may be used either alone or in combination with inhibitors of cGMP-specific phosphodiesterase to prevent or treat inflammation, cancer and other disorders, particularly of the gastrointestinal tract and the lung.

BACKGROUND OF THE INVENTION

Uroguanylin, guanylin and bacterial ST peptides are structurally related peptides that bind to a guanylate cyclase receptor and stimulate intracellular production of cyclic guanosine monophosphate (cGMP) (1-6). This results in the activation of the cystic fibrosis transmembrane conductance regulator (CFTR), an apical membrane channel for efflux of chloride from enterocytes lining the intestinal tract (1-6). Activation of CFTR and the subsequent enhancement of transepithelial secretion of chloride lead to stimulation of sodium and water secretion into the intestinal lumen. Therefore, by serving as paracrine regulators of CFTR activity, cGMP receptor agonists regulate fluid and electrolyte transport in the GI tract (1-6; U.S. Pat. No. 5,489,670). Thus, the cGMP-mediated activation of CFTR and the downstream signaling plays an important role in normal functioning of gut physiology. Therefore, any abnormality in this process could potentially lead to gastrointestinal disorders such as irritable bowel syndrome, inflammatory bowel disease, excessive acidity and cancer (25, 26).

The process of epithelial renewal involves the proliferation, migration, differentiation, senescence, and eventual loss of GI cells in the lumen (7, 8). The GI mucosa can be divided into three distinct zones based on the proliferation index of epithelial cells. One of these zones, the proliferative zone, consists of undifferentiated stem cells responsible for providing a constant source of new cells. The stem cells migrate upward toward the lumen to which they are extruded. As they migrate, the cells lose their capacity to divide and become differentiated for carrying out specialized functions of the GI mucosa (9). Renewal of GI mucosa is very rapid with complete turnover occurring within a 24-48 hour period (9). During this process mutated and unwanted cells are replenished with new cells. Hence, homeostasis of the GI mucosa is regulated by continual maintenance of the balance between proliferation and apoptotic rates (8).

The rates of cell proliferation and apoptosis in the gut epithelium can be increased or decreased in a wide variety of different circumstances, e.g., in response to physiological stimuli such as aging, inflammatory signals, hormones, peptides, growth factors, chemicals and dietary habits. In addition, an enhanced proliferation rate is frequently associated with a reduction in turnover time and an expansion of the proliferative zone (10). The proliferation index has been observed to be much higher in pathological cases of ulcerative colitis and other GI disorders (11). Thus, intestinal hyperplasia is the major promoter of gastrointestinal inflammation and carcinogenesis.

In addition to a role for uroguanylin and guanylin as modulators of intestinal fluid and ion secretion, these peptides may also be involved in the continual renewal of GI mucosa by maintaining the balance between proliferation and apoptosis in cells lining GI mucosa. Therefore, any disruption in this renewal process, due to reduced production of uroguanylin and/or guanylin can lead to GI inflammation and cancer (25, 26). This is consistent with previously published data in WO 01/25266, which suggest a peptide with the active domain of uroguanylin may function as an inhibitor of polyp development in the colon and may constitute a treatment of colon cancer. However, recent data also suggest that uroguanylin also binds to a currently unknown receptor, which is distinct from GC-C receptor (3,4). Knockout mice lacking this guanylate cyclase receptor show resistance to ST peptides in the intestine, but effects of uroguanylin and ST peptides are not disturbed in the kidney in vivo (3). These results were further supported by the fact that membrane depolarization induced by guanylin was blocked by genistein, a tyrosine kinase inhibitor, whereas hyperpolarization induced by uroguanylin was not effected (12, 13). Thus, it is not clear if the anti-colon cancer and anti-inflammatory activities of uroguanylin and its analogs are mediated through binding to one or both of these receptors.

Inflammatory bowel disease is a general name given to a group of disorders that cause intestines to become inflamed, characterized by red and swollen tissue. Gastrointestinal (GI) inflammation can be a chronic condition and often leads to GI cancer (14). Examples of such inflammatory bowel diseases (IBD) include Crohn's disease and ulcerative colitis (UC). It is estimated that as many as 1,000,000 Americans are afflicted with IBD, with male and female patients appearing to be equally affected. Most cases are diagnosed before age 30, but the disease can occur in the sixth, seventh, and later decades of life.

Crohn's disease is a serious inflammatory disease that predominantly effects ileum and colon, but can also occur in other sections of the GI tract, whereas UC is exclusively an inflammatory disease of the colon, the large intestine (15). Unlike Crohn's disease, in which all layers of the intestine are involved, and in which there can be normal healthy bowel in between patches of diseased bowel, UC affects only the innermost lining (mucosa) of the colon in a continuous manner (16). Depending on which portion of the GI tract is involved, Crohn's disease may be referred to as ileitis, regional enteritis, colitis, etc. Crohn's disease and UC differ from spastic colon or irritable bowel syndrome, which are motility disorders of the GI tract.

While the precise cause of IBD is not known, it is believed that the disruption of the process of continual renewal of GI mucosa may be involved in disease (17,18). The renewal process of the GI lining is an efficient and dynamic process involving the continual proliferation and replenishment of unwanted damaged cells. Proliferation rates of cells lining the GI mucosa are very high, second only to the hematopoietic system. Thus, the balance between proliferation and apoptosis is important to the maintenance of the homeostasis of the GI mucosa (19,20).

GI homeostasis depends on both proliferation and programmed cellular death (apoptosis) of epithelial cells lining the gut mucosa. Hence, cells are continually lost from the villus into the lumen of the gut and are replenished at a substantially equal rate by the proliferation of cells in the crypts, followed by their upward movement to the villus. It has become increasingly apparent that the control of cell death is an equally, if not more, important regulator of cell number and proliferation index (19,20). Reduced rates of apoptosis are often associated with abnormal growth, inflammation, and neoplastic transformation. Thus, both decreased proliferation and/or increased cell death may reduce cell number, whereas increased proliferation and/or reduced cell death may increase the proliferation index of intestinal tissue (20), which may lead to GI inflammatory diseases and cancer.

Uroguanylin and guanylin peptides also appear to promote apoptosis by controlling cellular ion flux. Alterations in apoptosis have been associated with tumor progression to the metastatic phenotype. While a primary gastrointestinal (GI) cancer is limited to the small intestine, colon, and rectum, it may metastasize and spread to such localities as bone, lymph nodes, liver, lung, peritoneum, ovaries, and brain. By enhancing the efflux of K+ and influx of Ca++, uroguanylin and related peptides may promote the death of transformed cells and thereby inhibit metastasis Irritable bowel syndrome (IBS) and chronic idiopathic constipation are pathological conditions that can cause a great deal of intestinal discomfort and distress but unlike the IBD diseases such as ulcerative colitis and Crohn's disease, IBS does not cause the serious inflammation or changes in bowel tissue and it is not thought to increase the risk of colorectal cancer. In the past, inflammatory bowel disease (IBD), celiac disease and irritable bowel syndrome (IBS) were regarded as completely separate disorders. Now, with the description of inflammation, albeit low-grade, in IBS, and of symptom overlap between IBS and celiac disease, this contention has come under question. Acute bacterial gastroenteritis is the strongest risk factor identified to date for the subsequent development of postinfective irritable bowel syndrome. Clinical risk factors include prolonged acute illness and the absence of vomiting. A genetically determined susceptibility to inflammatory stimuli may also be a risk factor for irritable bowel syndrome. The underlying pathophysiology indicates increased intestinal permeability and low-grade inflammation, as well as altered motility and visceral sensitivity (27). Serotonin (5-hydroxytryptamine [5-HT]) is a key modulator of gut function and is known to play a major role in pathophysiology of IBS. It has been shown that the activity of 5-HT is regulated by cGMP (28). Therefore, based on this observation as well as other effects of cGMP, we believe that GC-C agonists will be useful in the treatment of IBS.

Given the prevalence of inflammatory conditions in Western societies and the attendant risk of developing cancerous lesions from inflamed tissue, particularly intestinal tissue, a need exists to improve the treatment options for inflammatory conditions, particularly of the gastrointestinal tract.

SUMMARY OF THE INVENTION

The present invention is based upon the development of agonists of guanylate cyclase receptor. The agonists are analogs of uroguanylin and bacterial ST peptides and have superior properties such as for example high resistance to degradation at the N-terminus and C-terminus from carboxypeptidases and/or by other proteolytic enzymes present in the stimulated human intestinal juices and human gastric juices.

The peptides of the invention may be used to treat any condition that responds to enhanced intracellular levels of cGMP. Intracellular levels of cGMP can be increased by enhancing intracellular production of cGMP and/or by inhibition of its degradation by cGMP-specific phosphodiesterases. Among the specific conditions that can be treated or prevented are gastrointestinal disorders, inflammatory disorders, lung disorders, cancer, cardiac disorders, eye disorders, oral disorders, blood disorders, liver disorders, skin disorders, prostate disorders, endocrine disorders, increasing gastrointestinal motility and obesity. Gastointestinal disorders include for example, irritable bowel syndrome (IBS), nonulcer dyspepsia, chronic intestinal pseudo-obstruction, functional dyspepsia, colonic pseudo-obstruction, duodenogastric reflux, gastroesophageal reflux disease (GERD), ileus inflammation (e.g., post-operative ileus), gastroparesis, heartburn (high acidity in the GI tract), constipation (e.g., constipation associated with use of medications such as opioids, osteoarthritis drugs, osteoporosis drugs; post surgical constipation, constipation associated with neuropathic disorders. Inflammatory disorders include tissue and organ inflammation such as kidney inflammation (e.g., nephritis), gastrointestinal system inflammation (e.g., Crohn's disease and ulcerative colitis); pancreatic inflammation (e.g., pancreatis), lung inflammation (e.g., bronchitis or asthma) or skin inflammation (e.g., psoriasis, eczema). Lung Disorders include for example chronic obstructive pulmonary disease (COPD), and fibrosis. Cancer includes tissue and organ carcinogenesis including metatases such as for example gastrointestinal cancer, (e.g., gastric cancer, esophageal cancer, pancreatic cancer colorectal cancer, intestinal cancer, anal cancer, liver cancer, gallbladder cancer, or colon cancer; lung cancer; thyroid cancer; skin cancer (e.g., melanoma); oral cancer; urinary tract cancer (e.g. bladder cancer or kidney cancer); blood cancer (e.g. myeloma or leukemia) or prostate cancer. Cardiac disorders include for example, congestive heart failure, trachea cardia hypertension, high cholesterol, or high tryglycerides. Liver disorders include for example cirrhosis and fibrosis. In addition, GC-C agonist may also be useful to facilitate liver regeneration in liver transplant patients. Eye disorders include for example increased intra-ocular pressure, glaucoma, dry eyes retinal degeneration, disorders of tear glands or eye inflammation. Skin disorders include for example xerosis. Oral disorders include for example dry mouth (xerostomia), Sjögren's syndrome, gum diseases (e.g., periodontal disease), or salivary gland duct blockage or malfunction. Prostate disorders include for example benign prostatic hyperplasia (BPH). Endocrine disorders include for example diabetes mellitus, hyperthyroidism, hypothyroidism, and cystic fibrosis.

In one aspect, the present invention is directed to a peptide consisting essentially of the amino acid sequence of, SEQ ID NOs: 2-54 and 57-98 and to therapeutic compositions which contain these peptides. Preferred peptides include SEQ ID NO: 8, 9, 10, 58 and 59. The term "consisting essentially of" includes peptides that are identical to a recited sequence identification number and other sequences that do not differ substantially in terms of either structure or function. For the purpose of the present application, a peptide differs substantially if its structure varies by more than three amino acids from a peptide of SEQ ID NOs 2-54 and 57-98 or if its activation of cellular cGMP production is reduced by more than 50% compared to a control peptide such as SEQ ID NO:1, 55 or 56. Preferably, substantially similar peptides should differ by no more than two amino acids and not differ by more than about 25% with respect to activating cGMP production. The instant peptide sequences comprise at least 12 amino acid residues, preferably between 12 and 26 amino acids in length.

The peptides may be in a pharmaceutical composition in unit dose form, together with one or more pharmaceutically acceptable carrier, excipients or diluents. The term "unit dose form" refers to a single drug delivery entity, e.g., a tablet, capsule, solution or inhalation formulation. The amount of peptide present should be sufficient to have a positive therapeutic effect when administered to a patient (typically, between 100 µg and 3 g). What constitutes a "positive therapeutic effect" will depend upon the particular condition being treated and will include any significant improvement in a condition readily recognized by one of skill in the art. For example, it may constitute a reduction in inflammation, shrinkage of polyps or tumors, a reduction in metastatic lesions, etc.

In yet another aspect, an invention provides administering to said patient an effective dose of an inhibitor of cGMP-specific phosphodiesterase (cGMP-PDE) either concurrently or sequentially with said guanylate cyclase receptor agonist. The cGMP-PDE inhibitor include for example suldinac sulfone, zaprinast, and motapizone, vardenifil, and sildenafil. In addition, GC-C agonist peptides may be used in combination with inhibitors of cyclic nucleotide transporters.

Optionally, anti-inflammatory agents are also administered. Anti-inflammatory agents include for example steroids and non-steroidal anti-inflammatory drugs (NSAIDS).

Other features and advantages of the invention will be apparent from and are encompassed by the following detailed description and claims.

DETAILED DESCRIPTION

Figure 1A:
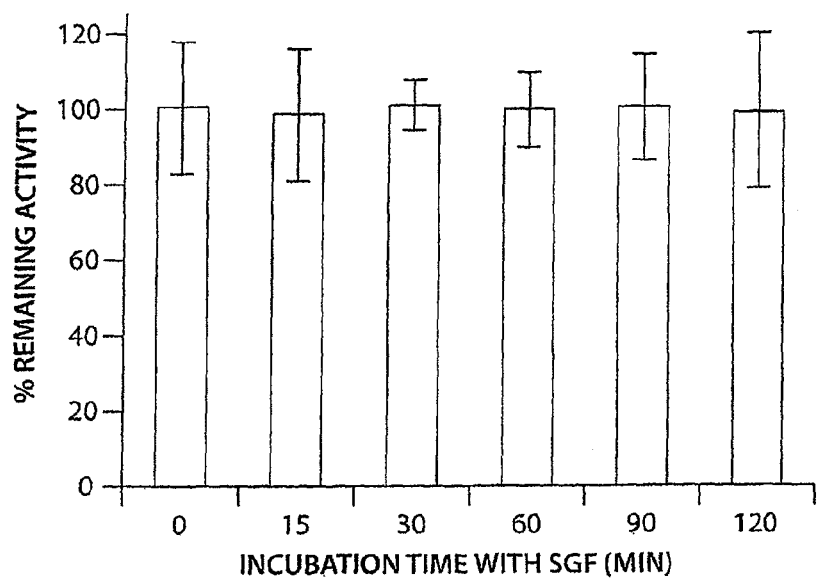
FIG. 1A is a bar chart showing the biological activity of SP-304 after incubation with simulated gastric fluid (SGF) for times as indicated. The biological activity of SP-304 was determined by measuring its ability to stimulate cGMP synthesis in T84 cells. Following the incubations, samples were used for their abilities to stimulate cGMP synthesis in T84 cells. The cGMP stimulation activity in sample at 0 min of incubation with SGF was taken as 100%. The activities in samples from other times of incubations with SGF were calculated as percentage of the activity in the sample at 0 min. The data is average of triplicates±SD

The present invention is based upon the development of agonists of guanylate cyclase-C (GC-C). The agonists are analogs of uroguanylin and bacterial ST peptides and have superior properties such as for example high resistance to degradation at the N-terminus and C-terminus from carboxypeptidases and/or by other proteolytic enzymes such as those present in the stimulated human intestinal juices and human gastric juices.

The GC-C is expressed on various cells including on gastrointestinal epithelial cells, and on extra-intestinal tissues including kidney, lung, pancreas, pituitary, adrenal, developing liver, heart and male and female reproductive tissues (reviewed in Vaandrager 2002 Mol Cell Biochem 230:73-83). The GC-C is a key regulator of fluid and electrolyte balance in the intestine and kidney. In the intestine, when stimulated, the GC-C causes an increase in intestinal epithelial cGMP. This increase in cGMP causes a decrease in water and sodium absorption and an increase in chloride and potassium ion secretion, leading to changes in intestinal fluid and electrolyte transport and increased intestinal motility.

The gualylate cyclase-C agonists according to the invention include SEQ ID NO:2-54, and SEQ ID NO: 57-98 and are summarized below in Table I and Table II. The gualylate cyclase-C agonists according to the invention are collectively referred to herein as "GCRA peptides".

TABLE I

GCRA peptides

| Name | Position of Disulfide bonds | Structure | SEQ ID NO |
|---|---|---|---|
| SP-304 | C4:C12, C7:C15 | $Asn^1$-$Asp^2$-$Glu^3$-$Cys^4$-$Glu^5$-$Leu^6$-$Cys^7$-$Va^8$-$Asn^9$-$Val^{10}$-$Ala^{11}$-$Cys^{12}$-$Thr^{13}$-$Gly^{14}$-$Cys^{15}$-$Leu^{16}$ | 1 |
| SP-326 | C3:C11, C6:C14 | $Asp^1$-$Glu^2$-$Cys^3$-$Glu^4$-$Leu^5$-$Cys^6$-$Val^7$-$Asn^8$-$Val^9$-$Ala^{10}$-$Cys^{11}$-$Thr^{12}$-$Gly^{13}$-$Cys^{14}$-$Leu^{15}$ | 2 |
| SP-327 | C2:C10, C5:C13 | $Asp^1$-$Glu^2$-$Cys^3$-$Glu^4$-$Leu^5$-$Cys^6$-$Val^7$-$Asn^8$-$Val^9$-$Ala^{10}$-$Cys^{11}$-$Thr^{12}$-$Gly^{13}$-$Cys^{14}$ | 3 |
| SP-328 | C2:C10, C5:C13 | $Glu^1$-$Cys^2$-$Glu^3$-$Leu^4$-$Cys^5$-$Val^6$-$Asn^7$-$Val^8$-$Ala^9$-$Cys^{10}$-$Thr^{11}$-$Gly^{12}$-$Cys^{13}$-$Leu^{14}$ | 4 |
| SP-329 | C2:C10, C5:C13 | $Glu^1$-$Cys^2$-$Glu^3$-$Leu^4$-$Cys^5$-$Val^6$-$Asn^7$-$Val^8$-$Ala^9$-$Cys^{10}$-$Thr^{11}$-$Gly^{12}$-$Cys^{13}$ | 5 |
| SP-330 | C1:C9, C4:C12 | $Cys^1$-$Glu^2$-$Leu^3$-$Cys^4$-$Val^5$-$Asn^6$-$Val^7$-$Ala^8$-$Cys^9$-$Thr^{10}$-$Gly^{11}$-$Cys^{12}$-$Leu^{13}$ | 6 |
| SP-331 | C1:C9, C4:C12 | $Cys^1$-$Glu^2$-$Leu^3$-$Cys^4$-$Val^5$-$Asn^6$-$Val^7$-$Ala^8$-$Cys^9$-$Thr^{10}$-$Gly^{11}$-$Cys^{12}$ | 7 |
| SP332 | C4:C12, C7:C15 | $Asn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$ | 8 |
| SP--333 | C4:C12, C7:C15 | $dAsn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$ | 9 |

TABLE I -continued

GCRA peptides

| Name | Position of Disulfide bonds | Structure | SEQ ID NO |
|---|---|---|---|
| SP-334 | C4:C12, C7:C15 | dAsn$^1$-dAsp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 10 |
| SP-335 | C4:C12, C7:C15 | dAsn$^1$-dAsp$^2$-dGlu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 11 |
| SP-336 | C4:C12, C7:C15 | dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 12 |
| SP-337 | C4:C12, C7:C15 | dAsn$^1$-Asp$^2$-Glu$^3$-Cys$^4$-Glu$^5$-dLeu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 13 |
| SP-338 | C4:C12, C7:C15 | Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$ | 14 |
| SP-342 | C4:C12, C7:C15 | PEG3-Asn$^1$-Asp$^2$-Glu$^3$-Cys$^4$-Glu$^5$-Leu$^6$-Cys7-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 15 |
| SP-343 | C4:C12, C7:C15 | PEG3-dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 16 |
| SP-344 | C4:C12, C7:C15 | PEG3-dAsn$^1$-dAsp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 17 |
| SP-347 | C4:C12, C7:C15 | dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 18 |
| SP-348 | C4:C12, C7:C15 | PEG3-Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 19 |
| SP-350 | C4:C12, C7:C15 | PEG3-dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 20 |
| SP-352 | C4:C12, C7:C15 | Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 21 |
| SP-358 | C4:C12, C7:C15 | PEG3-dAsn$^1$-dAsp$^2$-dGlu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 22 |
| SP-359 | C4:C12, C7:C15 | PEG3-dAsn$^1$-dAsp$^2$-dGlu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 23 |
| SP-360 | C4:C12, C7:C15 | dAsn$^1$-dAsp$^2$-dGlu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 24 |
| SP-361 | C4:C12, C7:C15 | dAsn$^1$-dAsp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 25 |
| SP-362 | C4:C12, C7:C15 | PEG3-dAsn$^1$-dAsp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 26 |
| SP-368 | C4:C12, C7:C15 | dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dNal$^{16}$ | 27 |
| SP-369 | C4:C12, C7:C15 | dAsn$^1$-Asp$^2$-Glu$^3$-Cys$^4$-Glu$^5$-Leu$^6$-Cys$^7$-AIB$^8$-Asn$^9$-AIB$^{10}$-Ala$^{11}$-Cys$^{12}$-Thr$^{13}$-Gly$^{14}$-Cys$^{15}$-dLeu$^{16}$ | 28 |
| SP-370 | C4:C12, C7:C15 | dAsn$^1$-Asp$^2$-Glu$^3$-Cys$^4$-Glu$^5$-Leu$^6$-Asp[Lactam]$^7$-Val$^8$-Asn$^9$-Val$^{10}$-Ala$^{11}$-Cys$^{12}$-Thr$^{13}$-Gly$^{14}$-Orn$^{15}$-dLeu$^{16}$ | 29 |
| SP-371 | C4:C12, C7:C15 | dAsn$^1$-Asp$^2$-Glu$^3$-Cys$^4$-Glu$^5$-Tyr$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 30 |
| SP-372 | C4:C12, C7:C15 | dAsn$^1$-Asp$^2$-Glu$^3$-Cys$^4$-Glu$^5$-Ser$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 31 |
| N1 | C4:C12, C7:C15 | PEG3-dAsn$^1$-Asp$^2$-Glu$^3$-Cys$^4$-Glu$^5$-Tyr$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 32 |
| N2 | C4:C12, C7:C15 | PEG3-dAsn$^1$-Asp$^2$-Glu$^3$-Cys$^4$-Glu$^5$-Tyr$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 33 |

TABLE I -continued

GCRA peptides

| Name | Position of Disulfide bonds | Structure | SEQ ID NO |
|---|---|---|---|
| N3 | C4:C12, C7:C15 | dAsn$^1$-Asp$^2$-Glu$^3$-Cys$^4$-Glu$^5$-Tyr$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 34 |
| N4 | C4:C12, C7:C15 | PEG3-dAsn$^1$-Asp$^2$-Glu$^3$-Cys$^4$-Glu$^5$-Ser$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 35 |
| N5 | C4:C12, C7:C15 | PEG3-dAsn$^1$-Asp$^2$-Glu$^3$-Cys$^4$-Glu$^5$-Ser$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 36 |
| N6 | C4:C12, C7:C15 | dAsn$^1$-Asp$^2$-Glu$^3$-Cys$^4$-Glu$^5$-Ser$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 37 |
| N7 | C4:C12, C7:C15 | Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 38 |
| N8 | C4:C12, C7:C15 | PEG3-Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$-PEG3 | 39 |
| N9 | C4:C12, C7:C15 | PEG3-Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 40 |
| N10 | C4:C12, C7:C15 | Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$-PEG3 | 41 |
| N11 | C4:C12, C7:C15 | PEG3-Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dSer$^{16}$-PEG3 | 42 |
| N12 | C4:C12, C7:C15 | PEG3-Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dSer$^{16}$ | 43 |
| N13 | C4:C12, C7:C15 | Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dSer$^{16}$-PEG3 | 44 |
| Formula I | C4:C12, C7:C15 | Asn$^1$-Asp$^2$-Glu$^3$-Cys$^4$-Xaa$^5$-Xaa$^6$-Cys$^7$-Xaa$^8$-Xaa$^9$-Xaa$^{10}$-Xaa$^{11}$-Cys$^{12}$-Xaa$^{13}$-Xaa$^{14}$-Cys$^{15}$-Xaa$^{16}$ | 45 |
| Formula II | C4:C12, C7:C15 | Xaa$_{n1}$-Cys$^4$-Xaa$^5$-Xaa$^6$-Cys$^7$-Xaa$^8$-Xaa$^9$-Xaa10-Xaa$^{11}$-Cys$^{12}$-Xaa$^{13}$-Xaa$^{14}$-Cys$^{15}$-Xaa$^{16}$ | 46 |
| Formula III | 4:12, 7:15 | Xaa$_{n1}$-Maa$^4$-Glu$^5$-Xaa$^6$-Maa$^7$-Val$^8$-Asn$^9$-Val$^{10}$-Ala$^{11}$-Maa$^{12}$-Thr$^{13}$-Gly$^{14}$-Maa$^{15}$-Xaan2 | 47 |
| Formula IV | 4:12, 7:15 | Xaa$_{n1}$-Maa$^4$-Xaa$^5$-Xaa$^6$-Maa$^7$-Xaa$^8$-Xaa$^9$-Xaa$^{10}$-Xaa$^{11}$-Maa$^{12}$-Xaa$^{13}$-Xaa$^{14}$-Maa$^{15}$-Xaan2 | 48 |
| Formula V) | C4:C12, C7:C15 | Asn$^1$-Asp2-Asp$^3$-Cys$^4$-Xaa$^5$-Xaa$^6$-Cys$^7$-Xaa$^8$-Asn$^9$-Xaa$^{10}$-Xaa$^{11}$-Cys$^{12}$-Xaa$^{13}$-Xaa$^{14}$-Cys$^{15}$-Xaa$^{16}$ | 49 |
| Formula VI | C4:C12, C7:C15 | dAsn$^1$-Glu$^2$-Glu$^3$-Cys$^4$-Xaa$^5$-Xaa$^6$-Cys$^7$-Xaa$^8$-Asn$^9$-Xaa$^{10}$-Xaa$^{11}$-Cys$^{12}$-Xaa$^{13}$-Xaa$^{14}$-Cys$^{15}$-d-Xaa$^{16}$ | 50 |
| Formula VII | C4:C12, C7:C15 | dAsn$^1$-dGlu$^2$-Asp$^3$-Cys$^4$-Xaa$^5$-Xaa$^6$-Cys$^7$-Xaa$^8$-Asn$^9$-Xaa$^{10}$-Xaa$^{11}$-Cys$^{12}$-Xaa$^{13}$-Xaa$^{14}$-Cys$^{15}$-d-Xaa$^{16}$ | 51 |
| Formula VII (NEW) | C4:C12, C7:C15 | dAsn$^1$-dAsp$^2$-Glu$^3$-Cys$^4$-Xaa$^5$-Xaa$^6$-Cys$^7$-Xaa$^8$-Asn$^9$-Xaa$^{10}$-Xaa$^{11}$-Cys$^{12}$-Xaa$^{13}$-Xaa$^{14}$-Cys$^{15}$-d-Xaa$^{16}$ | 52 |
| Formula VIII (NEW) | C4:C12, C7:C15 | dAsn$^1$-dAsp$^2$-dGlu$^3$-Cys$^4$-Xaa$^5$-Xaa$^6$-Cys$^7$-Xaa$^8$-Tyr$^9$-Xaa$^{10}$-Xaa$^{11}$-Cys$^{12}$-Xaa$^{13}$-Xaa$^{14}$-Cys$^{15}$-d-Xaa$^{16}$ | 53 |
| Formula IX | C4:C12, C7:C15 | dAsn$^1$-dGlu$^2$-dGlu$^3$-Cys$^4$-Xaa$^5$-Xaa$^6$-Cys$^7$-Xaa$^8$-Tyr$^9$-Xaa$^{10}$-Xa$^{11}$-Cys$^{12}$-Xaa$^{13}$-Xaa$^{14}$-Cys$^{15}$-d-Xaa$^{16}$ | 54 |

TABLE II

| Name | Position of Disulfide bonds | Structure | SEQ ID NO: |
|---|---|---|---|
| SP-339 | C1:C6, C2:C10, C5:13 | $Cys^1$-$Cys^2$-$Glu^3$-$Tyr^4$-$Cys^5$-$Cys^6$-$Asn^7$-$Pro^8$-$Ala^9$-$Cys^{10}$-$Thr^{11}$-$Gly^{12}$-$Cys^{13}$-$Tyr^{14}$ | 55 |
| SP-340 | C1:C6, C2:C10, C5:13 | $Cys^1$-$Cys^2$-$Glu^3$-$Tyr^4$-$Cys^5$-$Cys^6$-$Asn^7$-$Pro^8$-$Ala^9$-$Cys^{10}$-$Thr^{11}$-$Gly^{12}$-$Cys^{13}$ | 56 |
| SP-349 | C1:C6, C2:C10, C5:13 | PEG3-$Cys^1$-$Cys^2$-$Glu^3$-$Tyr^4$-$Cys^5$-$Cys^6$-$Asn^7$-$Pro^8$-$Ala^9$-$Cys^{10}$-$Thr^{11}$-$Gly^{12}$-$Cys^{13}$-$Tyr^{14}$-PEG3 | 57 |
| SP-353 | C3:C8, C4:C12, C7:15 | $Asn^1$-$Phe^2$-$Cys^3$-$Cys^4$-$Glu^5$-$Ser^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$ | 58 |
| SP-354 | C3:C8, C4:C12, C7:15 | $Asn^1$-$Phe^2$-$Cys^3$-$Cys^4$-$Glu^5$-$Phe^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$ | 59 |
| SP-355 | C1:C6, C2:C10, C5:13 | $Cys^1$-$Cys^2$-$Glu^3$-$Tyr^4$-$Cys^5$-$Cys^6$-$Asn^7$-$Pro^8$-$Ala^9$-$Cys^{10}$-$Thr^{11}$-$Gly^{12}$-$Cys^{13}$-$dTyr^{14}$ | 60 |
| SP-357 | C1:C6, C2:C10, C5:13 | PEG3-$Cys^1$-$Cys^2$-$Glu^3$-$Tyr^4$-$Cys^5$-$Cys^6$-$Asn^7$-$Pro^8$-$Ala^9$-$Cys^{10}$-$Thr^{11}$-$Gly^{12}$-$Cys^{13}$-$Tyr^{14}$ | 61 |
| SP-374 | C3:C8, C4:C12, C7:15 | $Asn^1$-$Phe^2$-$Cys^3$-$Cys^4$-$Glu^5$-$Thr^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$ | 62 |
| SP-375 | C3:C8, C4:C12, C7:15 | $Asn^1$-$Phe^2$-$Cys^3$-$Cys4$-$Glu^5$-$Ser^6$-$Cys^7$-$Cys^8$-$Asn^9$-$Pro^{10}$-$Ala^{11}$-$Cys^{12}$-$Thr^{13}$-$Gly^{14}$-$Cys^{15}$-$dTyr^{16}$ | 63 |
| SP-376 | C3:C8, C4:C12, C7:15 | $dAsn^1$-$Phe^2$-$Cys^3$-$Cys^4$-$Glu^5$-$Ser^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$ | 64 |
| SP-377 | C3:C8, C4:C12, C7:15 | $dAsn^1$-$Phe^2$-$Cys^3$-$Cys^4$-$Glu^5$-$Ser^6$-$Cys^7$-$Cys^8$-$Asn^9$-$Pro^{10}$-$Ala^{11}$-$Cys^{12}$-$Thr^{13}$-$Gly^{14}$-$Cys^{15}$-$dTyr^{16}$ | 65 |
| SP-378 | C3:C8, C4:C12, C7:15 | $Asn^1$-$Phe^2$-$Cys^3$-$Cys^4$-$Glu^5$-$Thr^6$-$Cys^7$-$Cys^8$-$Asn^9$-$Pro^{10}$-$Ala^{11}$-$Cys^{12}$-$Thr^{13}$-$Gly^{14}$-$Cys^{15}$-$dTyr^{16}$ | 66 |
| SP-379 | C3:C8, C4:C12, C7:15 | $dAsn^1$-$Phe^2$-$Cys^3$-$Cys^4$-$Glu^5$-$Thr^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$ | 67 |
| SP-380 | C3:C8, C4:C12, C7:15 | $dAsn^1$-$Phe^2$-$Cys^3$-$Cys^4$-$Glu^5$-$Thr^6$-$Cys^7$-$Cys^8$-$Asn^9$-$Pro^{10}$-$Ala^{11}$-$Cys^{12}$-$Thr^{13}$-$Gly^{14}$-$Cys^{15}$-$dTyr^{16}$ | 68 |
| SP-381 | C3:C8, C4:C12, C7:15 | $Asn^1$-$Phe^2$-$Cys^3$-$Cys^4$-$Glu^5$-$Phe^6$-$Cys^7$-$Cys^8$-$Asn^9$-$Pro^{10}$-$Ala^{11}$-$Cys^{12}$-$Thr^{13}$-$Gly^{14}$-$Cys^{15}$-$dTyr^{16}$ | 69 |
| SP-382 | C3:C8, C4:C12, C7:15 | $dAsn^1$-$Phe^2$-$Cys^3$-$Cys^4$-$Glu^5$-$Phe^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$ | 70 |
| SP-383 | C3:C8, C4:C12, C7:15 | $dAsn^1$-$Phe^2$-$Cys^3$-$Cys^4$-$Glu^5$-$Phe^6$-$Cys^7$-$Cys^8$-$Asn^9$-$Pro^{10}$-$Ala^{11}$-$Cys^{12}$-$Thr^{13}$-$Gly^{14}$-$Cys^{15}$-$dTyr^{16}$ | 71 |
| SP384 | C1:C6, C2:C10, C5:13 | $Cys^1$-$Cys^2$-$Glu^3$-$Tyr^4$-$Cys^5$-$Cys^6$-$Asn^7$-$Pro^8$-$Ala^9$-$Cys^{10}$-$Thr^{11}$-$Gly^{12}$-$Cys^{13}$-$Tyr^{14}$-PEG3 | 72 |

TABLE II -continued

GCRA Peptides

| Name | Position of Disulfide bonds | Structure | SEQ ID NO: |
|---|---|---|---|
| N14 | C1:C6, C2:C10, C5:13 | PEG3-Cys$^1$-Cys$^2$-Glu$^3$-Tyr$^4$-Cys$^5$-Cys$^6$-Asn$^7$-Pro$^8$-Ala$^9$-Cys$^{10}$-Thr$^{11}$-Gly$^{12}$-Cys$^{13}$-PEG3 | 73 |
| N15 | C1:C6, C2:C10, C5:13 | PEG3-Cys$^1$-Cys$^2$-Glu$^3$-Tyr$^4$-Cys$^5$-Cys$^6$-Asn$^7$-Pro$^8$-Ala$^9$-Cys$^{10}$-Thr$^{11}$-Gly$^{12}$-Cys$^{13}$ | 74 |
| N16 | C1:C6, C2:C10, C5:13 | Cys$^1$-Cys$^2$-Glu$^3$-Tyr$^4$-Cys$^5$-Cys$^6$-Asn$^7$-Pro$^8$-Ala$^9$-Cys$^{10}$-Thr$^{11}$-Gly$^{12}$-Cys$^{13}$-PEG3 | 75 |
| N17 | C3:C8, C4:C12, C7:15 | PEG3-Asn$^1$-Phe$^2$-Cys$^3$-Cys$^4$-Glu$^5$-Ser$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$-PEG3 | 76 |
| N18 | C3:C8, C4:C12, C7:15 | PEG3-Asn$^1$-Phe$^2$-Cys$^3$-Cys$^4$-Glu$^5$-Ser$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$ | 77 |
| N19 | C3:C8, C4:C12, C7:15 | Asn$^1$-Phe$^2$-Cys$^3$-Cys$^4$-Glu$^5$-Ser$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$-PEG3 | 78 |
| N20 | C3:C8, C4:C12, C7:15 | PEG3-Asn$^1$-Phe$^2$-Cys$^3$-Cys$^4$-Glu$^5$-Phe$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$-PEG3 | 79 |
| N21 | C3:C8, C4:C12, C7:15 | PEG3-Asn$^1$-Phe$^2$-Cys$^3$-Cys$^4$-Glu$^5$-Phe$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$ | 80 |
| N22 | C3:C8, C4:C12, C7:15 | Asn$^1$-Phe$^2$-Cys$^3$-Cys$^4$-Glu$^5$-Phe$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$-PEG3 | 81 |
| N23 | C3:C8, C4:C12, C7:15 | PEG3-Asn$^1$-Phe$^2$-Cys$^3$-Cys$^4$-Glu$^5$-Tyr$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$-PEG3 | 82 |
| N24 | C3:C8, C4:C12, C7:15 | PEG3-Asn$^1$-Phe$^2$-Cys$^3$-Cys$^4$-Glu$^5$-Tyr$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$ | 83 |
| N25 | C3:C8, C4:C12, C7:15 | Asn$^1$-Phe$^2$-Cys$^3$-Cys$^4$-Glu$^5$-Tyr$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$-PEG3 | 84 |
| N26 | C1:C6, C2:C10, C5:13 | Cys$^1$-Cys$^2$-Glu3-Ser$^4$-Cys$^5$-Cys$^6$-Asn$^7$-Pro$^8$-Ala$^9$-Cys$^{10}$-Thr$^{11}$-Gly$^{12}$-Cys$^{13}$-Tyr$^{14}$ | 85 |
| N27 | C1:C6, C2:C10, C5:13 | Cys$^1$-Cys$^2$-Glu3-Phe$^4$-Cys$^5$-Cys$^6$-Asn$^7$-Pro$^8$-Ala$^9$-Cys$^{10}$-Thr$^{11}$-Gly$^{12}$-Cys$^{13}$-Tyr$^{14}$ | 86 |
| N28 | C1:C6, C2:C10, C5:13 | Cys$^1$-Cys$^2$-Glu3-Ser$^4$-Cys$^5$-Cys$^6$-Asn$^7$-Pro$^8$-Ala$^9$-Cys$^{10}$-Thr$^{11}$-Gly$^{12}$-Cys$^{13}$- | 87 |
| N29 | C1:C6, C2:C10, C5:13 | Cys$^1$-Cys$^2$-Glu3-Phe$^4$-Cys$^5$-Cys$^6$-Asn$^7$-Pro$^8$-Ala$^9$-Cys$^{10}$-Thr$^{11}$-Gly$^{12}$-Cys$^{13}$ | 88 |
| N30 | 1:6, 2:10, 5:13 | Pen$^1$-Pen$^2$-Glu3-Tyr$^4$-Pen$^5$-Pen$^6$-Asn$^7$-Pro$^8$-Ala$^9$-Pen$^{10}$-Thr$^{11}$-Gly$^{12}$-Pen$^{13}$-Tyr$^{14}$ | 89 |
| N31 | 1:6, 2:10, 5:13 | Pen$^1$-Pen$^2$-Glu3-Tyr$^4$-Pen$^5$-Pen$^6$-Asn$^7$-Pro$^8$-Ala$^9$-Pen$^{10}$-Thr$^{11}$-Gly$^{12}$-Pen$^{13}$ | 90 |
| Formula X | C9:C14, C10:C18, C13:21 | Xaa$^1$-Xaa$^2$-Xaa$^3$-Xaa$^4$-Xaa$^5$-Xaa$^6$-Asn$^7$-Tyr$^8$-Cys$^9$-Cys$^{10}$-Xaa$^{11}$-Tyr$^{12}$-Cys$^{13}$-Cys$^{14}$-Xaa$^{15}$-Xaa$^{16}$-Xaa$^{17}$-Cys$^{18}$-Xaa$^{19}$-Xaa$^{20}$-Cys$^{21}$-Aaa$^{22}$ | 91 |

TABLE II -continued

GCRA Peptides

| Name | Position of Disulfide bonds | Structure | SEQ ID NO: |
|---|---|---|---|
| Formula XI | C9:C14, C10:C18, C13:21 | $Xaa^1$-$Xaa^2$-$Xaa^3$-$Xaa^4$-$Xaa^5$-$Xaa^6$-$Asn^7$-$Phe^8$-$Cys^9$-$Cys^{10}$-$Xaa^{11}$-$Phe^{12}$-$Cys^{13}$-$Cys^{14}$-$Xaa^{15}$-$Xaa^{16}$-$Xaa^{17}$-$Cys^{18}$-$Xaa^{19}$-$Xaa^{20}$-$Cys^{21}$-$Aaa^{22}$ | 92 |
| Formula XII | C3:C8, C4:C12, C7:15 | $Asn^1$-$Phe^2$-$Cys^3$-$Cys^4$-$Xaa^5$-$Phe^6$-$Cys^7$-$Cys^8$-$Xaa^9$-$Xaa^{10}$-$Xaa^{11}$-$Cys^{12}$-$Xaa^{13}$-$Xaa^{14}$-$Cys^{15}$-$Xaa^{16}$ | 93 |
| Formula XIII | 3:8, 4:12, C:15 | $Asn^1$-$Phe^2$-$Pen^3$-$Cys^4$-$Xaa^5$-$Phe^6$-$Cys^7$-$Pen^8$-$Xaa^9$-$Xaa^{10}$-$Xaa^{11}$-$Cys12$-$Xaa^{13}$-$Xaa^{14}$-$Cys^{15}$-$Xaa^{16}$ | 94 |
| Formula XIV | 3:8, 4:12, 7:15 | $Asn^1$-$Phe^2$-$Maa^3$-$Maa^4$-$Xaa^5$-$Xaa^6$-$Maa^7$-$Maa^8$-$Xaa^9$-$Xaa^{10}$-$Xaa^{11}$-$Maa^{12}$-$Xaa^{13}$-$Xaa^{14}$-$Maa^{15}$-$Aaa^{16}$ | 95 |
| Formula XV | 1:6, 2:10, 5:13 | $Maa^1$-$Maa^2$-$Glu3$-$Xaa^4$-$Maa^5$-$Maa^6$-$Asn^7$-$Pro^8$-$Ala^9$-$Maa^{10}$-$Thr^{11}$-$Gly^{12}$-$Maa^{13}$-$Tyr^{14}$ | 96 |
| Formula XVI | 1:6, 2:10, 5:13 | $Maa^1$-$Maa^2$-$Glu3$-$Xaa^4$-$Maa^5$-$Maa^6$-$Asn^7$-$Pro^8$-$Ala^9$-$Maa^{10}$-$Thr^{11}$-$Gly^{12}$-$Maa^{13}$- | 97 |
| Formula XVII | 1:6, 2:10, 5:13 | $Xaa_{n3}$-$Maa^1$-$Maa^2$-$Xaa^3$-$Xaa^4$-$Maa^5$-$Maa^6$-$Xaa^7$-$Xaa^8$-$Xaa^9$-$Maa^{10}$-$Xaa^{11}$-$Xaa^{12}$-$Maa^{13}$-$Xaa_{n2}$ | 98 |

The GCRA peptides described herein bind the guanylate cyclase C (GC-C) and stimulate intracellular production of cyclic guanosine monophosphate (cGMP). Optionally, the GCRA peptides induce apoptosis. In some aspects, the GCRA peptides stimulate intracellular cGMP production at higher levels than naturally occurring GC-C agonists (e.g., uroguanylin, guanylin, and ST peptides) and/or SP-304. For example, the GCRA peptides of the invention stimulate 5%, 10%, 20%, 30%, 40%, 50%, 75%, 90% or more intracellular cGMP compared to naturally occurring GC-C agonists and/or SP-304. The terms induced and stimulated are used interchangeably throughout the specification. The GCRA peptides described herein are more stable than naturally occurring GC-C agonists and/or SP-304. By more stable it is meant that the peptide degrade less and/or more slowly in simulated gastrointestinal fluid and/or simulated intestinal fluid compared to naturally occurring GC-C agonists and/or SP-304. For example, the GCRA peptide of the invention degrade 2%, 3%, 5%, 10%, 15%, 20%, 30%, 40%, 50%, 75%, 90% or less compared to naturally occurring GC-C agonists and/or SP-304.

The GCRA peptides described herein have therapeutic value in the treatment of a wide variety of disorders and conditions including for example gastrointestinal disorders, inflammatory disorders, lung disorders, cancer, cardiac disorders, eye disorders, oral disorders, blood disorders, liver disorders, skin disorders, prostate disorders, endocrine disorders, increasing gastrointestinal motility and obesity. Gastointestinal disorders include for example, irritable bowel syndrome (IBS), non-ulcer dyspepsia, chronic intestinal pseudo-obstruction, functional dyspepsia, colonic pseudo-obstruction, duodenogastric reflux, gastroesophageal reflux disease (GERD)ileus (e.g., post-operative ileus), gastroparesis, heartburn (high acidity in the GI tract), constipation (e.g., constipation associated with use of medications such as opioids, osteoarthritis drugs, osteoporosis drugs; post surgical constipation, constipation associated with neuropathic disorders. Inflammatory disorders include tissue and organ inflammation such as kidney inflammation (e.g., nephritis), gastrointestinal system inflammation (e.g., Crohn's disease and ulcerative colitis); pancreatic inflammation (e.g., pancreatis), lung inflammation (e.g., bronchitis or asthma) or skin inflammation (e.g., psoriasis, eczema). Lung Disorders include for example chronic obstructive pulmonary disease (COPD), and fibrosis. Cancer includes tissue and organ carcinogenesis including metatases such as for example gastrointestinal cancer, (e.g., gastric cancer, esophageal cancer, pancreatic cancer colorectal cancer, intestinal cancer, anal cancer, liver cancer, gallbladder cancer, or colon cancer; lung cancer; thyroid cancer; skin cancer (e.g., melanoma); oral cancer; urinary tract cancer (e.g. bladder cancer or kidney cancer); blood cancer (e.g. myeloma or leukemia) or prostate cancer. Cardiac disorders include for example, congestive heart failure, trachea cardia hypertension, high cholesterol, or high tryglycerides. Liver disorders include for example cirrhosis and fibrosis. Eye disorders include for example increased intra-ocular pressure, glaucoma, dry eyes retinal degeneration, disorders of tear glands or eye inflammation. Skin disorders include for example xerosis. Oral disorders include for example dry mouth (xerostomia), Sjögren's syndrome, gum diseases (e.g., periodontal disease), or salivary gland duct blockage or malfunction. Prostate disorders include for example Benign prostatic hyperplasia (BPH). Endocrine disorders include for example diabetes mellitus, hyperthyroidism, hypothyroidism, and cystic fibrosis.

As used herein, the term "guanylate cyclase C (GC-C)" refers to the class of guanylate cyclase C receptor on any cell type to which the inventive agonist peptides or natural agonists described herein bind. As used herein, "intestinal guanylate cyclase receptor" is found exclusively on epithelial cells lining the GI mucosa. Uroguanylin, guanylin, and ST peptides are expected to bind to these receptors and may induce apoptosis. The possibility that there may be different receptors for each agonist peptide is not excluded. Hence, the term refers to the class of guanylate cyclase receptors on epithelial cells lining the GI mucosa.

As used herein, the term "GCR agonist" is meant to refer to peptides and/or other compounds that bind to an intestinal guanylate cyclase C and stimulate fluid and electrolyte transport. This term also covers fragments and pro-peptides that bind to GC-C and stimulate fluid and water secretion.

As used herein, the term "substantially equivalent" is meant to refer to a peptide that has an amino acid sequence equivalent to that of the binding domain where certain residues may be deleted or replaced with other amino acids without impairing the peptide's ability to bind to an intestinal guanylate cyclase receptor and stimulate fluid and electrolyte transport.

Addition of carriers (e.g., phosphate-buffered saline or PBS) and other components to the composition of the present invention is well within the level of skill in this art. In addition to the compound, such compositions may contain pharmaceutically acceptable carriers and other ingredients known to facilitate administration and/or enhance uptake. Other formulations, such as microspheres, nanoparticles, liposomes, and immunologically-based systems may also be used in accordance with the present invention. Other examples include formulations with polymers (e.g., 20% w/v polyethylene glycol) or cellulose, or enteric formulations.

The present invention is based upon several concepts. The first is that there is a cGMP-dependent mechanism which regulates the balance between cellular proliferation and apoptosis and that a reduction in cGMP levels, due to a deficiency of uroguanylin/guanylin and/or due to the activation of cGMP-specific phosphodiesterases, is an early and critical step in neoplastic transformation. A second concept is that the release of arachidonic acid from membrane phospholipids, which leads to the activation of cytoplasmic phospholipase A2 (cPLA2), cyclooxygenase-2 (COX-2) and possibly 5-lipoxygenase (5-LO) during the process of inflammation, is down-regulated by a cGMP-dependent mechanism, leading to reduced levels of prostaglandins and leukotrienes, and that increasing intracellular levels of cGMP may therefore produce an anti-inflammatory response. In addition, a cGMP-dependent mechanism, is thought to be involved in the control of proinflammatory processes. Therefore, elevating intracellular levels of cGMP may be used as a means of treating and controlling gastrointestinal disorders, inflammatory disorders, lung disorders, cancer, cardiac disorders, eye disorders, oral disorders, blood disorders, liver disorders, skin disorders, prostate disorders, endocrine disorders, increasing gastrointestinal motility and obesity. Gastointestinal disorders include for example, irritable bowel syndrome (IBS), non-ulcer dyspepsia, chronic intestinal pseudo-obstruction, functional dyspepsia, colonic pseudo-obstruction, duodenogastric reflux, gastroesophageal reflux disease (GERD)ileus (e.g., post-operative ileus), gastroparesis, heartburn (high acidity in the GI tract), constipation (e.g., constipation associated with use of medications such as opioids, osteoarthritis drugs, osteoporosis drugs; post surgical constipation, constipation associated with neuropathic disorders. Inflammatory disorders include tissue and organ inflammation such as kidney inflammation (e.g., nephritis), gastrointestinal system inflammation (e.g., Crohn's disease and ulcerative colitis); pancreatic inflammation (e.g., pancreatis), lung inflammation (e.g., bronchitis or asthma) or skin inflammation (e.g., psoriasis, eczema). Lung Disorders include for example COPD and fibrosis. Cancer includes tissue and organ carcinogenesis including metatases such as for example gastrointestinal cancer, (e.g., gastric cancer, esophageal cancer, pancreatic cancer colorectal cancer, intestinal cancer, anal cancer, liver cancer, gallbladder cancer, or colon cancer; lung cancer; thyroid cancer; skin cancer (e.g., melanoma); oral cancer; urinary tract cancer (e.g. bladder cancer or kidney cancer); blood cancer (e.g. myeloma or leukemia) or prostate cancer. Cardiac disorders include for example, congestive heart failure, trachea cardia hypertension, high cholesterol, or high tryglycerides. Liver disorders include for example cirrhosis and fibrosis. Eye disorders include for example increased intra-ocular pressure, glaucoma, dry eyes retinal degeneration, disorders of tear glands or eye inflammation. Skin disorders include for example xerosis. Oral disorders include for example dry mouth (xerostomia), Sjögren's syndrome, gum diseases (e.g., periodontal disease), or salivary gland duct blockage or malfunction. Prostate disorders include for example Benign prostatic hyperplasia (BPH). Endocrine disorders include for example diabetes mellitus, hyperthyroidism, hypothyroidism, and cystic fibrosis.

Without intending to be bound by any theory, it is envisioned that ion transport across the plasma membrane may prove to be an important regulator of the balance between cell proliferation and apoptosis that will be affected by agents altering cGMP concentrations. Uroguanylin has been shown to stimulate K+ efflux, Ca++ influx and water transport in the gastrointestinal tract (3). Moreover, atrial natriuretic peptide (ANP), a peptide that also binds to a specific guanylate cyclase receptor, has also been shown to induce apoptosis in rat mesangial cells, and to induce apoptosis in cardiac myocytes by a cGMP mechanism (21-24).

Binding of the present agonists to a guanylate cyclase receptor stimulates production of cGMP. This ligand-receptor interaction, via activation of a cascade of cGMP-dependent protein kinases and CFTR, induces apoptosis in target cells. Therefore, administration of the novel peptides defined by SEQ ID NO:2-54, and SEQ ID NO: 57-98, as shown in Tables I and II, or peptides similar to uroguanylin, or guanylin or E. coli ST peptide are useful in eliminating or, at least retarding, the onset of gastrointestinal disorders, inflammatory disorders, lung disorders, cancer, cardiac disorders, eye disorders, oral disorders, blood disorders, liver disorders, skin disorders, prostate disorders, endocrine disorders, increasing gastrointestinal motility and obesity. Gastointestinal disorders include for example, irritable bowel syndrome (IBS), non-ulcer dyspepsia, chronic intestinal pseudo-obstruction, functional dyspepsia, colonic pseudo-obstruction, duodenogastric reflux, gastroesophageal reflux disease (GERD), ileus inflammation (e.g., post-operative ileus), gastroparesis, heartburn (high acidity in the GI tract), constipation (e.g., constipation associated with use of medications such as opioids, osteoarthritis drugs, osteoporosis drugs; post surgical constipation, constipation associated with neuropathic disorders. Inflammatory disorders include tissue and organ inflammation such as kidney inflammation (e.g., nephritis), gastrointestinal system inflammation (e.g., Crohn's disease and ulcerative colitis); pancreatic inflammation (e.g., pancreatis), lung inflammation (e.g., bronchitis or asthma) or skin inflammation (e.g., psoriasis, eczema). Lung Disorders include for example chronic obstructive pulmonary disease (COPD), and fibrosis. Cancer includes tissue and organ carcinogenesis including metatases such as for example gastrointestinal cancer, (e.g., gastric cancer, esophageal cancer, pancreatic cancer colorectal cancer, intestinal cancer, anal cancer, liver cancer, gallbladder cancer, or colon cancer; lung cancer; thyroid cancer; skin cancer (e.g., melanoma); oral cancer; urinary tract cancer (e.g. bladder cancer or kidney cancer); blood cancer (e.g. myeloma or leukemia) or prostate cancer. Cardiac disorders include for example, congestive heart failure, trachea cardia hypertension, high cholesterol, or high tryglycerides. Liver disorders include for example cirrhosis and fibrosis. Eye disorders include for example increased intra-ocular pressure, glaucoma, dry eyes retinal degeneration, disorders of tear glands or eye inflammation. Skin disorders include for example xerosis. Oral disorders include for example dry mouth (xerostomia), Sjögren's syndrome, gum diseases (e.g., periodontal disease), or salivary gland duct blockage or malfunction. Prostate disorders include for example Benign prostatic hyperplasia (BPH). Endocrine disorders include for example diabetes mellitus, hyperthyroidism, hypothyroidism, and cystic fibrosis.

Uroguanylin is a circulating peptide hormone with natriuretic activity and has been found to stimulate fluid and electrolyte transport in a manner similar to another family of heat stable enterotoxins (ST peptides) secreted by pathogenic strains of E. coli and other enteric bacteria that activate guanylate cyclase receptor and cause secretory diarrhea. Unlike bacterial ST peptides, the binding of uroguanylin to guanylate cyclase receptor is dependent on the physiological pH of the gut. Therefore, uroguanylin is expected to regulate fluid and electrolyte transport in a pH dependent manner and without causing severe diarrhea.

GCRA Peptides

In one aspect, the invention provides a GCRA peptide. The GCRA peptides are analogues uroguanylin and bacterial ST peptide. No particular length is implied by the term "peptide". In some embodiments, the GCRA peptide is less than 25 amino acids in length, e.g., less than or equal to 20, 15, 14, 13, 12, 11, 10, or 5 amino acid in length.

The GCRA peptides can be polymers of L-amino acids, D-amino acids, or a combination of both. For example, in various embodiments, the peptides are D retro-inverso peptides. The term "retro-inverso isomer" refers to an isomer of a linear peptide in which the direction of the sequence is reversed and the chirality of each amino acid residue is inverted. See, e.g., Jameson et al., Nature, 368, 744-746 (1994); Brady et al., Nature, 368, 692-693 (1994). The net result of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence of the invention may be made into an D retro-inverso peptide by synthesizing a reverse of the sequence for the corresponding native L-amino acid sequence. For example a GCRA peptide includes the sequence of SEQ ID NO: SEQ ID NO:2-54, and SEQ ID NO: 57-98. In various embodiments, the GCRA peptide includes the amino acid sequence of SEQ ID NO:45-54 and SEQ ID NO:87-98 where the peptide induces cGMP production by a cell. In various embodiments the GCRA peptide of the invention includes the amino acid sequence according to Formulas I-IX (e.g. SEQ ID NO:45-54) with the proviso that the GCRA peptide is not SEQ ID NO:1. In further embodiments the GCRA peptide of the invention include the amino acid sequence according to Formulas X-XVII (e.g. SEQ ID NO:87-98) with the proviso that the GCRA peptide is not SEQ ID NO:55 or SEQ ID NO:56. By inducing cGMP production is meant that the GCRA peptide induces the production of intracellular cGMP. Intracellular cGMP is measured by methods known in the art. For example, the GCRA peptide of the invention stimulate 5%, 10%, 20%, 30%, 40%, 50%, 75%, 90% or more intracellular cGMP compared to naturally occurring GC-C agonists. Optionally, the GCRA peptides of the invention of the invention stimulate 5%, 10%, 20%, 30%, 40%, 50%, 75%, 90% or more intracellular cGMP compared SP-304 (SEQ ID NO:1). In further embodiments, the GCRA peptide stimulates apoptosis, e.g., programmed cell death or activate the cystic fibrosis transmembrane conductance regulator (CFTR). In some embodiments the GCRA peptides described herein are more stable than naturally occurring GC-C agonists and/or SP-304 (SEQ ID NO:1), SP-339 (SEQ ID NO: 55) or SP-340 (SEQ ID NO: 56). By more stable it is meant that the peptide degrade less and/or more slowly in simulated gastric fluid and/or simulated intestinal fluid compared to naturally occurring GC-C agonists and/or SP-304. For example, the GCRA peptide of the invention degrade 2%, 3%, 5%, 10%, 15%, 20%, 30%, 40%, 50%, 75%, 90% or less compared to naturally occurring GC-C agonists and/or SP-304, SP-339 or SP-340.

As used herein PEG3, 3 PEG, is meant to denote polyethylene glycol such as include aminoethyloxy-ethyloxy-acetic acid (AeeA). As used herein, (e.g., in Formulas I-XVII, SEQ ID NO:45-54 and SEQ ID NO:87-98) $X_{aa}$ is any any natural, unnatural amino acid or amino acid analogue; $M_{aa}$ is a Cysteine (Cys), Penicillamine (Pen) homocysteine, or 3-mercaptoproline; $Xaa_{n1}$ is meant to denote an amino acid sequence of any any natural, unnatural amino acid or amino acid analogue that is one, two or three residues in length; $Xaa_{n2}$ is meant to denote an amino acid sequence of any any natural, unnatural amino acid or amino acid analogue that is zero or one residue in length; and $Xaa_{n3}$ is meant to denote an amino acid sequence of any any natural, unnatural amino acid or amino acid analogue that is zero, one, two, three, four, five or six residues in length. Additionally, any amino acid represented by Xaa, $Xaa_{n1}$, $Xaa_{n2}$, or $Xaa_{n3}$ may be an L-amino acid, a D-amino acid, a methylated amino acid or any combination of thereof. Optionally, any GCRA peptide represented by Formulas I-VII may contain on or more polyethylene glycol residues at the N-terminus, C-terminus or both. An exemplary polyethylene glycol include aminoethyloxy-ethyloxy-acetic acid and polymers thereof.

In some embodiments, GCRA peptides include peptides containing the amino acid sequence of Formula I, wherein at least one amino acid of Formula I is a D-amino acid or a methylated amino acid and/or the amino acid at position 16 is a serine. Preferably, the amino acid at position 16 of Formula I is a D-amino acid or a methylated amino acid. For example, the amino acid at position 16 of Formula I is a d-leucine or a d-serine. Optionally, one or more of the amino acids at position 1-3 of Formula I are D-amino acids or methylated amino acids or a combination of D-amino acids or methylated amino acids. For example, Asn1, Asp2 or Glu3 (or a combination thereof) of Formula I is a D-amino acids or a methylated amino acid. Preferably, the amino acid at position $Xaa^6$ of Formula I is a leucine, serine or tyrosine.

In alternative embodiments, GCRA peptides include peptides containing containing the amino acid sequence of Formula II, wherein at least one amino acid of Formula II is a D-amino acid or a methylated amino acid. Preferably, the amino acid denoted by $Xaa_{n2}$ of Formula II is a D-amino acid or a methylated amino acid. In some embodiments the amino acid denoted by $Xaa_{n2}$ of Formula II is a leucine, d-leucine, serine or d-serine. Preferably, the one or more of the amino acids denoted by $Xaa_{n1}$ of Formula II is a D-amino acid or a methylated amino acid. Preferably, the amino acid at position $Xaa^6$ of Formula II is a leucine, serine or tyrosine.

In some embodiments, GCRA peptides include peptides containing the amino acid sequence of Formula III, wherein 1) at at least one amino acid of Formula I is a D-amino acid or a methylated amino acid and/or 2) Maa is not a cysteine. Preferably, the amino acid denoted by $Xaa_{n2}$ of Formula III is a D-amino acid or a methylated amino acid. In some embodiments the amino acid denoted by $Xaa_{n2}$ of Formula III is a leucine, d-leucine, serine or d-serine. Preferably, the one or more of the amino acids denoted by $Xaa_{n1}$ of Formula III is a D-amino acid or a methylated amino acid. Preferably, the amino acid at position $Xaa^6$ of Formula III is a leucine, serine or tyrosine.

In other embodiments, GCRA peptides include peptides containing containing the amino acid sequence of Formula IV, wherein at least one amino acid of Formula IV is a D-amino acid or a methylated amino acid and/or 2) Maa is not a cysteine. Preferably, the $Xaa_{n2}$ of Formula IV is a D-amino acid or a methylated amino acid. In some embodiments the amino acid denoted by $Xaa_{n2}$ of Formula IV is a leucine, d-leucine, serine or d-serine. Preferably, the one or more of the amino acids denoted by $Xaa_{n1}$ of Formula IV is a D-amino acid or a methylated amino acid. Preferably, the amino acid denoted $Xaa^6$ of Formula IV is a leucine, serine or tyrosine. In further embodiments, GCRA peptides include peptides containing the amino acid sequence of Formula V, wherein at at least one amino acid of Formula V is a D-amino acid or a methylated amino acid. Preferably, the amino acid at position 16 of Formula V is a D-amino acid or a methylated amino acid. For example, the amino acid at position 16 (i.e., $Xaa^{16}$) of Formula V is a d-leucine or a d-serine. Optionally, one or more of the amino acids at position 1-3 of Formula V are D-amino acids or methylated amino acids or a combination of D-amino acids or methylated amino acids. For example, Asn1, Asp2 or Glu3 (or a combination thereof) of Formula V is a D-amino acids or a methylated amino acid. Preferably, the amino acid denoted at $Xaa^6$ of Formula V is a leucine, serine or tyrosine.

In additional embodiments, GCRA peptides include peptides containing containing the amino acid sequence of Formula VI, VII, VIII, IX. Preferably, the amino acid at position 6 of Formula VI, VII, VIII, IX. is a leucine, serine or tyrosine. In some aspects the amino acid at position 16 of Formula VI, VII, VIII, IX is a leucine or a serine. Preferably, the amino acid at position 16 of Formula V is a D-amino acid or a methylated amino acid.

In preferred embodiments, the GCRA peptide is SP-332 (SEQ ID NO:8), SP-333 (SEQ ID NO:9) or SP-334 (SEQ ID NO:10).

In additional embodiments, GCRA peptides include peptides containing containing the amino acid sequence of Formula X, XI, XII, XIII, XIV, XV, XVI or XVII. Optionally, one or more amino acids of Formulas X, XI, XII, XIII, XIV, XV, XVI or XVII is a D-amino acid or a methylated amino acid. Preferably, the amino acid at the carboxy terminus of the peptides according to Formulas X, XI, XII, XIII, XIV, XV, XVI or XVII is a D-amino acid or a methylated amino acid. For example the amino acid at the carboxy terminus of the peptides according to Formulas X, XI, XII, XIII, XIV, XV, XVI or XVII is a D-tyrosine Preferably, the amino acid denoted by $Xaa^6$ of Formula XIV is a tyrosine, phenylanaline or a serine. Most preferably the amino acid denoted by $Xaa^6$ of Formula XIV is a phenyalanine or a serine. Preferably, the amino acid denoted by $Xaa^4$ of Formula XV, XVI or XVII is a tyrosine, phenylalanine or a serine. Most preferably, the amino acid position $Xaa^4$ of Formula V, XVI or XVII is a phenyalanine or a serine.

In preferred embodiments, the GCRA peptide is SP-353 (SEQ ID NO:58) or SP-354 (SEQ ID NO:59).

In certain embodiments, one or more amino acids of the GCRA peptides can be replaced by a non-naturally occurring amino acid or a naturally or non-naturally occurring amino acid analog. There are many amino acids beyond the standard 20 (Ala, Arg, Asn, Asp, Cys, Gln, Glu, Gly, His, Ile, Leu, Lys, Met, Phe, Pro, Ser, Thr, Trp, Tyr, and Val). Some are naturally-occurring others are not. (See, for example, Hunt, The Non-Protein Amino Acids: In Chemistry and Biochemistry of the Amino Acids, Barrett, Chapman and Hall, 1985). For example, an aromatic amino acid can be replaced by 3,4-dihydroxy-L-phenylalanine, 3-iodo-L-tyrosine, triiodothyronine, L-thyroxine, phenylglycine (Phg) or nor-tyrosine (norTyr). Phg and norTyr and other amino acids including Phe and Tyr can be substituted by, e.g., a halogen, —CH3, —OH, —CH2NH3, —C(O)H, —CH2CH3, —CN, —CH2CH2CH3, —SH, or another group. Any amino acid can be substituted by the D-form of the amino acid.

With regard to non-naturally occurring amino acids or naturally and non-naturally occurring amino acid analogs, a number of substitutions in the polypeptide and agonists described herein are possible alone or in combination.

For example, glutamine residues can be substituted with gamma-Hydroxy-Glu or gamma-Carboxy-Glu. Tyrosine residues can be substituted with an alpha substituted amino acid such as L-alpha-methylphenylalanine or by analogues such as: 3-Amino-Tyr; Tyr(CH3); Tyr(PO3(CH3)2); Tyr (SO3H); beta-Cyclohexyl-Ala; beta-(1-Cyclopentenyl)-Ala; beta-Cyclopentyl-Ala; beta-Cyclopropyl-Ala; beta-Quinolyl-Ala; beta-(2-Thiazolyl)-Ala; beta-(Triazole-1-yl)-Ala; beta-(2-Pyridyl)-Ala; beta-(3-Pyridyl)-Ala; Amino-Phe; Fluoro-Phe; Cyclohexyl-Gly; tBu-Gly; beta-(3-benzothienyl)-Ala; beta-(2-thienyl)-Ala; 5-Methyl-Trp; and A-Methyl-Trp. Proline residues can be substituted with homopro (L-pipecolic acid); hydroxy-Pro; 3,4-Dehydro-Pro; 4-fluoro-Pro; or alpha-methyl-Pro or an N(alpha)-C(alpha) cyclized amino acid analogues with the structure: n=0, 1, 2, 3 Alanine residues can be substituted with alpha-substituted or N-methylated amino acid such as alpha-amino isobutyric acid (aib), L/D-alpha-ethylalanine (L/D-isovaline), L/D-methylvaline, or L/D-alpha-methylleucine or a non-natural amino acid such as beta-fluoro-Ala. Alanine can also be substituted with: n=0, 1, 2, 3 Glycine residues can be substituted with alpha-amino isobutyric acid (aib) or L/D-alpha-ethylalanine (L/D-isovaline).

Further examples of unnatural amino acids include: an unnatural analog of tyrosine; an unnatural analogue of glutamine; an unnatural analogue of phenylalanine; an unnatural analogue of serine; an unnatural analogue of threonine; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; an amino acid that is amidated at a site that is not naturally amidated, a metal-containing amino acid; a radioactive amino acid; a photo-caged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid (e.g., an amino acid containing deuterium, tritium, $^{13}C$, $^{15}N$, or $^{18}O$); a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an α,α disubstituted amino acid; a β-amino acid; a cyclic amino acid other than proline; an O-methyl-L-tyrosine; an L-3-(2-naphthyl)alanine; a 3-methyl-phenylalanine; a ρ-acetyl-L- phenylalanine; an O-4-allyl-L-tyrosine; a 4-propyl-L-tyrosine; a tri-O-acetyl-GlcNAc β-serine; an L-Dopa; a fluorinated phenylalanine; an isopropyl-L-phenylalanine; a p-azido-L-phenylalanine; a p-acyl-L-phenylalanine; a p-benzoyl-L-phenylalanine; an L-phosphoserine; a phosphonoserine; a phosphonotyrosine; a p-iodo-phenylalanine; a 4-fluorophenylglycine; a p-bromophenylalanine; a p-amino-L-phenylalanine; an isopropyl-L-phenylalanine; L-3-(2-naphthyl)alanine; D-3-(2-naphthyl)alanine (dNal); an amino-, isopropyl-, or O-allyl-containing phenylalanine analogue; a dopa, 0-methyl-L-tyrosine; a glycosylated amino acid; a p-(propargyloxy)phenylalanine; dimethyl-Lysine; hydroxy-proline; mercaptopropionic acid; methyl-lysine; 3-nitro-tyrosine; norleucine; pyro-glutamic acid; Z (Carbobenzoxyl); ϵ-Acetyl-Lysine; β-alanine; aminobenzoyl derivative; aminobutyric acid (Abu); citrulline; aminohexanoic acid; aminoisobutyric acid (AIB); cyclohexylalanine; d-cyclohexylalanine; hydroxyproline; nitro-arginine; nitro-phenylalanine; nitro-tyrosine; norvaline; octahydroindole carboxylate; ornithine (Orn); penicillamine (PEN); tetrahydroisoquinoline; acetamidomethyl protected amino acids and pegylated amino acids. Further examples of unnatural amino acids and amino acid analogs can be found in U.S. 20030108885, U.S. 20030082575, US20060019347 (paragraphs 410-418) and the references cited therein. The polypeptides of the invention can include further modifications including those described in US20060019347, paragraph 589. Exemplary GCRA peptides which include a n0n-naturally occurring amino acid include for example SP-368 and SP-369.

In some embodiments, an amino acid can be replaced by a naturally-occurring, non-essential amino acid, e.g., taurine.

Alternatively, the GCRA peptides are cyclic peptides. GCRA cyclic peptide are prepared by methods known in the art. For example, macrocyclization is often accomplished by forming an amide bond between the peptide N- and C-termini, between a side chain and the N- or C-terminus [e.g., with $K_3Fe(CN)_6$ at pH 8.5] (Samson et al., Endocrinology, 137: 5182-5185 (1996)), or between two amino acid side chains, such as cysteine. See, e.g., DeGrado, Adv Protein Chem, 39: 51-124 (1988). In various aspects the GCRA peptides are [4,12; 7,15] bicycles.

In some GCRA peptides one or both members of one or both pairs of Cys residues which normally form a disulfide bond can be replaced by homocysteine, penicillamine, 3-mercaptoproline (Kolodziej et al. 1996 Int J Pept Protein Res 48:274); β, β dimethylcysteine (Hunt et al. 1993 Int JPept Protein Res 42:249) or diaminopropionic acid (Smith et al. 1978 J Med Chem 2 1:117) to form alternative internal cross-links at the positions of the normal disulfide bonds.

In addition, one or more disulfide bonds can be replaced by alternative covalent cross-links, e.g., an amide linkage (—CH2CH(O)NHCH 2- or —CH2NHCH(O)CH 2-), an ester linkage, a thioester linkage, a lactam bridge, a carbamoyl linkage, a urea linkage, a thiourea linkage, a phosphonate ester linkage, an alkyl linkage (—CH2CH2CH2CH2-), an alkenyl linkage (—CH 2CH=CHCH 2-), an ether linkage (—CH2CH2OCH2- or —CH2OCH2CH2-), a thioether linkage (—CH2CH2SCH2- or —CH2SCH2CH2-), an amine linkage (—CH2CH2NHCH2- or —CH2NHCH 2CH2-) or a thioamide linkage (—CH2CH(S)HNHCH 2- or —CH2NHCH(S)CH 2-). For example, Ledu et al. (Proc Nat'l Acad. Sci. 100:11263-78, 2003) describe methods for preparing lactam and amide cross-links. Exemplary GCRA peptides which include a lactam bridge include for example SP-370.

The GCRA peptides can have one or more conventional polypeptide bonds replaced by an alternative bond. Such replacements can increase the stability of the polypeptide. For example, replacement of the polypeptide bond between a residue amino terminal to an aromatic residue (e.g. Tyr, Phe, Trp) with an alternative bond can reduce cleavage by carboxy peptidases and may increase half-life in the digestive tract. Bonds that can replace polypeptide bonds include: a retro-inverso bond (C(O)—NH instead of NH—C(O); a reduced amide bond (NH—CH2); a thiomethylene bond (S—CH2 or CH2-S); an oxomethylene bond (O—CH 2 or CH2-O); an ethylene bond (CH2-CH2); a thioamide bond (C(S)—NH); a trans-olefine bond (CH=CH); a fluoro substituted trans-olefine bond (CF=CH); a ketomethylene bond (C(O)—CHR or CHR—C(O) wherein R is H or CH3; and a fluoro-ketomethylene bond (C(O)—CFR or CFR—C(O) wherein R is H or F or CH3.

The GCRA peptides can be modified using standard modifications. Modifications may occur at the amino (N-), carboxy (C-) terminus, internally or a combination of any of the preceeding. In one aspect described herein, there may be more than one type of modification on the polypeptide. Modifications include but are not limited to: acetylation, amidation, biotinylation, cinnamoylation, farnesylation, formylation, myristoylation, palmitoylation, phosphorylation (Ser, Tyr or Thr), stearoylation, succinylation, sulfurylation and cyclisation (via disulfide bridges or amide cyclisation), and modification by Cys3 or Cys5. The GCRA peptides described herein may also be modified by 2,4-dinitrophenyl (DNP), DNP-lysine, modification by 7-Amino-4-methyl-coumarin (AMC), flourescein, NBD (7-Nitrobenz-2-Oxa-1,3-Diazole), p-nitro-anilide, rhodamine B, EDANS (5-((2-aminoethyl)amino)naphthalene-1-sulfonic acid), dabcyl, dabsyl, dansyl, texas red, FMOC, and Tamra (Tetramethylrhodamine). The GCRA peptides described herein may also be conjugated to, for example, polyethylene glycol (PEG); alkyl groups (e.g., C1-C20 straight or branched alkyl groups); fatty acid radicals; combinations of PEG, alkyl groups and fatty acid radicals (See, U.S. Pat. No. 6,309,633; Soltero et al., 2001 Innovations in Pharmaceutical Technology 106-110); BSA and KLH (Keyhole Limpet Hemocyanin). The addition of PEG and other polymers which can be used to modify polypeptides of the invention is described in US20060 19347 section IX.

Also included in the invention are peptides that biologically or functional equivalent to the peptides described herein. The term "biologically equivalent" or functional equivalent" is intended to mean that the compositions of the present invention are capable of demonstrating some or all of the cGMP production modulatory effects.

GCRA peptides can also include derivatives of GCRA peptides which are intended to include hybrid and modified forms of GCRA peptides in which certain amino acids have been deleted or replaced and modifications such as where one or more amino acids have been changed to a modified amino acid or unusual amino acid and modifications such as glycosylation so long the modified form retains the biological activity of GCRA peptides. By retaining the biological activity, it is meant that cGMP and or apoptosis is induced by the GCRA peptide, although not necessarily at the same level of potency as that of a naturally-occurring GCRA peptide identified.

Preferred variants are those that have conservative amino acid substitutions made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a GCRA polypeptide is replaced with another amino acid residue from the same side chain family. Alternatively, in another embodiment, mutations can be introduced randomly along all or part of a GCRA coding sequence, such as by saturation mutagenesis, and the resultant mutants can be screened to identify mutants that retain activity.

Also included within the meaning of substantially homologous is any GCRA peptide which may be isolated by virtue of cross-reactivity with antibodies to the GCRA peptide.

Preparation of GCRA Peptides

GCRA peptides are easily prepared using modern cloning techniques, or may be synthesized by solid state methods or by site-directed mutagenesis. A GCRA peptide may include dominant negative forms of a polypeptide.

Chemical synthesis may generally be performed using standard solution phase or solid phase peptide synthesis techniques, in which a peptide linkage occurs through the direct condensation of the amino group of one amino acid with the carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (See, Gross and Meienhofer, eds., "The Peptides: Analysis, Synthesis, Biology,"Vol. 1-4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection is necessary to minimize racemization during segment condensation. Solubility considerations are also a factor. Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., J. Am. Chem. Soc., 1963, 85:2149, which involves assembling a linear peptide chain on a resin support using protected amino acids. Solid phase peptide synthesis typically utilizes either the Boc or Fmoc strategy, which are well known in the art.

Those of ordinary skill in the art will recognize that, in solid phase synthesis, deprotection and coupling reactions must go to completion and the side-chain blocking groups must be stable throughout the synthesis. In addition, solid phase synthesis is generally most suitable when peptides are to be made on a small scale.

Acetylation of the N-terminal can be accomplished by reacting the final peptide with acetic anhydride before cleavage from the resin. C-amidation is accomplished using an appropriate resin such as methylbenzhydrylamine resin using the Boc technology.

Alternatively the GCRA peptides are produced by modern cloning techniques For example, the GCRA peptides are produced either in bacteria including, without limitation, *E. coli*, or in other existing systems for polypeptide or protein production (e.g., *Bacillus subtilis*, baculovirus expression systems using *Drosophila* Sf9 cells, yeast or filamentous fungal expression systems, mammalian cell expression systems), or they can be chemically synthesized. If the GCRA peptide or variant peptide is to be produced in bacteria, e.g., *E. coli*, the nucleic acid molecule encoding the polypeptide may also encode a leader sequence that permits the secretion of the mature polypeptide from the cell. Thus, the sequence encoding the polypeptide can include the pre sequence and the pro sequence of, for example, a naturally-occurring bacterial ST polypeptide. The secreted, mature polypeptide can be purified from the culture medium.

The sequence encoding a GCRA peptide described herein can be inserted into a vector capable of delivering and maintaining the nucleic acid molecule in a bacterial cell. The DNA molecule may be inserted into an autonomously replicating vector (suitable vectors include, for example, pGEM3Z and pcDNA3, and derivatives thereof). The vector nucleic acid may be a bacterial or bacteriophage DNA such as bacteriophage lambda or M13 and derivatives thereof. Construction of a vector containing a nucleic acid described herein can be followed by transformation of a host cell such as a bacterium. Suitable bacterial hosts include but are not limited to, *E. coli, B subtilis, Pseudomonas, Salmonella*. The genetic construct also includes, in addition to the encoding nucleic acid molecule, elements that allow expression, such as a promoter and regulatory sequences. The expression vectors may contain transcriptional control sequences that control transcriptional initiation, such as promoter, enhancer, operator, and repressor sequences.

A variety of transcriptional control sequences are well known to those in the art. The expression vector can also include a translation regulatory sequence (e.g., an untranslated 5' sequence, an untranslated 3' sequence, or an internal ribosome entry site). The vector can be capable of autonomous replication or it can integrate into host DNA to ensure stability during polypeptide production.

The protein coding sequence that includes a GCRA peptide described herein can also be fused to a nucleic acid encoding a polypeptide affinity tag, e.g., glutathione S-transferase (GST), maltose E binding protein, protein A, FLAG tag, hexa-histidine, myc tag or the influenza HA tag, in order to facilitate purification. The affinity tag or reporter fusion joins the reading frame of the polypeptide of interest to the reading frame of the gene encoding the affinity tag such that a translational fusion is generated. Expression of the fusion gene results in translation of a single polypeptide that includes both the polypeptide of interest and the affinity tag. In some instances where affinity tags are utilized, DNA sequence encoding a protease recognition site will be fused between the reading frames for the affinity tag and the polypeptide of interest.

Genetic constructs and methods suitable for production of immature and mature forms of the GCRA peptides and variants described herein in protein expression systems other than bacteria, and well known to those skilled in the art, can also be used to produce polypeptides in a biological system.

The peptides disclosed herein may be modified by attachment of a second molecule that confers a desired property upon the peptide, such as increased half-life in the body, for example, pegylation. Such modifications also fall within the scope of the term "variant" as used herein.

Therapeutic Methods

The present invention provides for both prophylactic and therapeutic methods of treating a subject at risk of (or susceptible to) a disorder or having a disorder associated that is mediated by guanylate cyclase receptor agonists. Disorders mediated by the guanylate cyclase receptor agonists include gastrointestinal disorders, inflammatory disorders, lung disorders, cancer, cardiac disorders, eye disorders, oral disorders, blood disorders, liver disorders, skin disorders, prostate disorders, endocrine disorders, increasing gastrointestinal motility and obesity. Gastointestinal disorders include for example, irritable bowel syndrome (IBS), non-ulcer dyspepsia, chronic intestinal pseudo-obstruction, functional dyspepsia, colonic pseudo-obstruction, duodenogastric reflux, gastroesophageal reflux disease (GERD)ileus (e.g., post-operative ileus), gastroparesis, heartburn (high acidity in the GI tract), constipation (e.g., constipation associated with use of medications such as opioids, osteoarthritis drugs, osteoporosis drugs; post surgical constipation, constipation associated with neuropathic disorders. Inflammatory disorders include tissue and organ inflammation such as kidney inflammation (e.g., nephritis), gastrointestinal system inflammation (e.g., Crohn's disease and ulcerative colitis); pancreatic inflammation (e.g., pancreatis), lung inflammation (e.g., bronchitis or asthma) or skin inflammation (e.g., psoriasis, eczema). Lung Disorders include for example chronic obstructive pulmonary disease (COPD), and fibrosis. Cancer includes tissue and organ carcinogenesis including metatases such as for example gastrointestinal cancer, (e.g., gastric cancer, esophageal cancer, pancreatic cancer colorectal cancer, intestinal cancer, anal cancer, liver cancer, gallbladder cancer, or colon cancer; lung cancer; thyroid cancer; skin cancer (e.g., melanoma); oral cancer; urinary tract cancer (e.g. bladder cancer or kidney cancer); blood cancer (e.g. myeloma or leukemia) or prostate cancer. Cardiac disorders include for example, congestive heart failure, trachea cardia hypertension, high cholesterol, or high tryglycerides. Liver disorders include for example cirrhosis and fibrosis. Eye disorders include for example increased intra-ocular pressure, glaucoma, dry eyes retinal degeneration, disorders of tear glands or eye inflammation. Skin disorders include for example xerosis. Oral disorders include for example dry mouth (xerostomia), Sjögren's syndrome, gum diseases (e.g., periodontal disease), or salivary gland duct blockage or malfunction. Prostate disorders include for example benign prostatic hyperplasia (BPH). Endocrine disorders include for example diabetes mellitus, hyperthyroidism, hypothyroidism, and cystic fibrosis.

The term "treatment" refers to reducing or alleviating symptoms in a subject, preventing symptoms from worsening or progressing, and/or preventing disease in a subject who is free therefrom. For a given subject, improvement in a symptom, its worsening, regression, or progression may be determined by any objective or subjective measure. Efficacy of the treatment may be measured as an improvement in morbidity or mortality (e.g., lengthening of survival curve for a selected population). Thus, effective treatment would include therapy of existing disease, control of disease by slowing or stopping its progression, prevention of disease occurrence, reduction in the number or severity of symptoms, or a combination thereof. The effect may be shown in a controlled study using one or more statistically significant criteria.

Intracellular cGMP induced by exposing, e.g., contacting a tissue (e.g., gastrointestinals tissue) or cell with GCRA agonists. GC-C receptors are expressed throughout the GI tract starting from esophagus, duodenum, jejunum, ilium, caecum and colon. Human colon cancer cell lines (T81, CaCo-2 and HT-29) also express GC-C receptors. By inducing is meant an increase in cGMP production compared to a tissue or cell that has not been in contact with GCRA peptide or variant. Tissues or cells are directly contacted with a GCRA peptide or variant. Alternatively, the GCRA peptide or variant is administered systemically. GCRA peptide or variant are administered in an amount sufficient to increase intracellular cGMP concentration. cGMP production is measured by a cell-based assay known in the art (25).

Disorders are treated, prevented or alleviated by administering to a subject, e.g., a mammal such as a human in need thereof, a therapeutically effective dose of a GCRA peptide. The GCRA peptides may be in a pharmaceutical composition in unit dose form, together with one or more pharmaceutically acceptable excipients. The term "unit dose form" refers to a single drug delivery entity, e.g., a tablet, capsule, solution or inhalation formulation. The amount of peptide present should be sufficient to have a positive therapeutic effect when administered to a patient (typically, between 10 µg and 3 g). What constitutes a "positive therapeutic effect" will depend upon the particular condition being treated and will include any significant improvement in a condition readily recognized by one of skill in the art.

The GCRA peptides can be administered alone or in combination with other agents. For example the GCRA peptides can be administered in combination with inhibitors of cGMP dependent phosphodiesterase, such as, for example, suldinac sulfone, zaprinast, motapizone, vardenafil or sildenifil; one or more other chemotherapeutic agents; or anti-inflammatory drugs such as, for example, steroids or non-steroidal anti-inflammatory drugs (NSAIDS), such as aspirin.

Combination therapy can be achieved by administering two or more agents, e.g., a GCRA peptide described herein and another compound, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so.

The GCRA peptides described herein may be combined with phosphodiesterase inhibitors, e.g., sulindae sulfone, Zaprinast, sildenafil, vardenafil or tadalafil to further enhance levels of cGMP in the target tissues or organs.

Combination therapy can also include two or more administrations of one or more of the agents used in the combination. For example, if agent X and agent Y are used in a combination, one could administer them sequentially in any combination one or more times, e.g., in the order X-Y-X, X-X-Y, Y-X-Y, Y-Y-X, X-X-Y-Y, etc.

Combination therapy can also include the administration of two or more agents via different routes or locations. For example, (a) one agent is administered orally and another agents is administered intravenously or (b) one agent is administered orally and another is administered locally. In each case, the agents can either simultaneously or sequentially. Approximated dosages for some of the combination therapy agents described herein are found in the "BNF Recommended Dose" column of tables on pages 11-17 of WO01/76632 (the data in the tables being attributed to the March 2000 British National Formulary) and can also be found in other standard formularies and other drug prescribing directories. For some drugs, the customary prescribed dose for an indication will vary somewhat from country to country.

The GCRA peptides, alone or in combination, can be combined with any pharmaceutically acceptable carrier or medium. Thus, they can be combined with materials that do not produce an adverse, allergic or otherwise unwanted reaction when administered to a patient. The carriers or mediums used can include solvents, dispersants, coatings, absorption promoting agents, controlled release agents, and one or more inert excipients (which include starches, polyols, granulating agents, microcrystalline cellulose (e.g. celphere, Celphere Beads®), diluents, lubricants, binders, disintegrating agents, and the like), etc. If desired, tablet dosages of the disclosed compositions may be coated by standard aqueous or non-aqueous techniques.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a GCRA agonist) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. Such as mannitol, fructooligosaccharides, polyethylene glycol and other excepients. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, incorporated fully herein by reference.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

The pharmaceutical compositions can be included in a container, pack, or dispenser together with instructions for administration.

Compositions of the present invention may also optionally include other therapeutic ingredients, anti-caking agents, preservatives, sweetening agents, colorants, flavors, desiccants, plasticizers, dyes, glidants, anti-adherents, anti-static agents, surfactants (wetting agents), antioxidants, film-coating agents, and the like. Any such optional ingredient must be compatible with the compound described herein to insure the stability of the formulation.

The composition may contain other additives as needed, including for example lactose, glucose, fructose, galactose, trehalose, sucrose, maltose, raffnose, maltitol, melezitose, stachyose, lactitol, palatinite, starch, xylitol, mannitol, myo-inositol, and the like, and hydrates thereof, and amino acids, for example alanine, glycine and betaine, and polypeptides and proteins, for example albumen.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents such as: BINDERS: corn starch, potato starch, other starches, gelatin, natural and synthetic gums such as acacia, xanthan, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone (e.g., povidone, crospovidone, copovidone, etc), methyl cellulose, Methocel, pre-gelatinized starch (e.g., STARCH 1500® and STARCH 1500 LM®, sold by Colorcon, Ltd.), hydroxypropyl methyl cellulose, microcrystalline cellulose (FMC Corporation, Marcus Hook, Pa., USA), or mixtures thereof, FILLERS: talc, calcium carbonate (e.g., granules or powder), dibasic calcium phosphate, tribasic calcium phosphate, calcium sulfate (e.g., granules or powder), microcrystalline cellulose, powdered cellulose, dextrates, kaolin, mannitol, silicic acid, sorbitol, starch, pre-gelatinized starch, dextrose, fructose, honey, lactose anhydrate, lactose monohydrate, lactose and aspartame, lactose and cellulose, lactose and microcrystalline cellulose, maltodextrin, maltose, mannitol, microcrystalline cellulose & guar gum, molasses, sucrose, or mixtures thereof, DISINTEGRANTS: agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums (like gellan), low-substituted hydroxypropyl cellulose, or mixtures thereof, LUBRICANTS: calcium stearate, magnesium stearate, mineral oil, light mineral oil, glycerin, sorbitol, mannitol, polyethylene glycol, other glycols, stearic acid, sodium lauryl sulfate, sodium stearyl fumarate, vegetable based fatty acids lubricant, talc, hydrogenated vegetable oil (e.g., peanut oil, cottonseed oil, sunflower oil, sesame oil, olive oil, corn oil and soybean oil), zinc stearate, ethyl oleate, ethyl laurate, agar, syloid silica gel (AEROSIL 200, W.R. Grace Co., Baltimore, Md. USA), a coagulated aerosol of synthetic silica (Deaussa Co., Piano, Tex. USA), a pyrogenic silicon dioxide (CAB-O-SIL, Cabot Co., Boston, Mass. USA), or mixtures thereof, ANTI-CAKING AGENTS: calcium silicate, magnesium silicate, silicon dioxide, colloidal silicon dioxide, talc, or mixtures thereof, ANTIMICROBIAL AGENTS: benzalkonium chloride, benzethonium chloride, benzoic acid, benzyl alcohol, butyl paraben, cetylpyridinium chloride, cresol, chlorobutanol, dehydroacetic acid, ethylparaben, methylparaben, phenol, phenylethyl alcohol, phenoxyethanol, phenylmercuric acetate, phenylmercuric nitrate, potassium sorbate, propylparaben, sodium benzoate, sodium dehydroacetate, sodium propionate, sorbic acid, thimersol, thymo, or mixtures thereof, and COATING AGENTS: sodium carboxymethyl cellulose, cellulose acetate phthalate, ethylcellulose, gelatin, pharmaceutical glaze, hydroxypropyl cellulose, hydroxypropyl methylcellulose (hypromellose), hydroxypropyl methyl cellulose phthalate, methylcellulose, polyethylene glycol, polyvinyl acetate phthalate, shellac, sucrose, titanium dioxide, carnauba wax, microcrystalline wax, gellan gum, maltodextrin, methacrylates, microcrystalline cellulose and carrageenan or mixtures thereof.

The formulation can also include other excipients and categories thereof including but not limited to L-histidine, Pluronic®, Poloxamers (such as Lutrol® and Poloxamer 188), ascorbic acid, glutathione, permeability enhancers (e.g. lipids, sodium cholate, acylcarnitine, salicylates, mixed bile salts, fatty acid micelles, chelators, fatty acid, surfactants, medium chain glycerides), protease inhibitors (e.g. soybean trypsin inhibitor, organic acids), pH lowering agents and absorption enhancers effective to promote bioavailability (including but not limited to those described in U.S. Pat. No. 6,086,918 and U.S. Pat. No. 5,912,014), creams and lotions (like maltodextrin and carrageenans); materials for chewable tablets (like dextrose, fructose, lactose monohydrate, lactose and aspartame, lactose and cellulose, maltodextrin, maltose, mannitol, microcrystalline cellulose and guar gum, sorbitol crystalline); parenterals (like mannitol and povidone); plasticizers (like dibutyl sebacate, plasticizers for coatings, polyvinylacetate phthalate); powder lubricants (like glyceryl behenate); soft gelatin capsules (like sorbitol special solution); spheres for coating (like sugar spheres); spheronization agents (like glyceryl behenate and microcrystalline cellulose); suspending/gelling agents (like carrageenan, gellan gum, mannitol, microcrystalline cellulose, povidone, sodium starch glycolate, xanthan gum); sweeteners (like aspartame, aspartame and lactose, dextrose, fructose, honey, maltodextrin, maltose, mannitol, molasses, sorbitol crystalline, sorbitol special solution, sucrose); wet granulation agents (like calcium carbonate, lactose anhydrous, lactose monohydrate, maltodextrin, mannitol, microcrystalline cellulose, povidone, starch), caramel, carboxymethylcellulose sodium, cherry cream flavor and cherry flavor, citric acid anhydrous, citric acid, confectioner's sugar, D&C Red No. 33, D&C Yellow #10 Aluminum Lake, disodium edetate, ethyl alcohol 15%, FD&C Yellow No. 6 aluminum lake, FD&C Blue #1 Aluminum Lake, FD&C Blue No. 1, FD&C blue no. 2 aluminum lake, FD&C Green No. 3, FD&C Red No. 40, FD&C Yellow No. 6 Aluminum Lake, FD&C Yellow No. 6, FD&C Yellow No. 10, glycerol palmitostearate, glyceryl monostearate, indigo carmine, lecithin, manitol, methyl and propyl parabens, mono ammonium glycyrrhizinate, natural and artificial orange flavor, pharmaceutical glaze, poloxamer 188, Polydextrose, polysorbate 20, polysorbate 80, polyvidone, pregelatinized corn starch, pregelatinized starch, red iron oxide, saccharin sodium, sodium carboxymethyl ether, sodium chloride, sodium citrate, sodium phosphate, strawberry flavor, synthetic black iron oxide, synthetic red iron oxide, titanium dioxide, and white wax.

Solid oral dosage forms may optionally be treated with coating systems (e.g. Opadry® fx film coating system, for example Opadry® blue (OY-LS-20921), Opadry® white (YS-2-7063), Opadry® white (YS-1-7040), and black ink (S-1-8 106).

The agents either in their free form or as a salt can be combined with a polymer such as polylactic-glycoloic acid (PLGA), poly-(I)-lactic-glycolic-tartaric acid (P(I)LGT) (WO 01/12233), polyglycolic acid (U.S. Pat. No. 3,773,919), polylactic acid (U.S. Pat. No. 4,767,628), poly(ε-caprolactone) and poly(alkylene oxide) (U.S. 20030068384) to create a sustained release formulation. Such formulations can be used to implants that release a polypeptide or another agent over a period of a few days, a few weeks or several months depending on the polymer, the particle size of the polymer, and the size of the implant (See, e.g., U.S. Pat. No. 6,620, 422). Other sustained release formulations and polymers for use in are described in EP 0 467 389 A2, WO 93/24150, U.S. Pat. No. 5,612,052, WO 97/40085, WO 03/075887, WO 01/01964A2, U.S. Pat. No. 5,922,356, WO 94/155587, WO 02/074247A2, WO 98/25642, U.S. Pat. No. 5,968,895, U.S. Pat. No. 6,180,608, U.S. 20030171296. U.S. 20020176841, U.S. Pat. No. 5,672,659, U.S. Pat. No. 5,893,985, U.S. Pat. No. 5,134,122, U.S. Pat. No. 5,192,741, U.S. Pat. No. 5,192, 741, U.S. Pat. No. 4,668,506, U.S. Pat. No. 4,713,244, U.S. Pat. No. 5,445,832 U.S. Pat. No. 4,931,279, U.S. Pat. No. 5,980,945, WO 02/058672, WO 9726015, WO 97/04744, and US200200 19446. In such sustained release formulations microparticles (Delie and Blanco-Prieto 2005 Molecule 10:65-80) of polypeptide are combined with microparticles of polymer. One or more sustained release implants can be placed in the large intestine, the small intestine or both. U.S. Pat. No. 6,011,01 and WO 94/06452 describe a sustained release formulation providing either polyethylene glycols (i.e. PEG 300 and PEG 400) or triacetin. WO 03/053401 describes a formulation which may both enhance bioavailability and provide controlled release of the agent within the GI tract. Additional controlled release formulations are described in WO 02/38129, EP 326151, U.S. Pat. No. 5,236, 704, WO 02/30398, WO 98/13029; U.S. 20030064105, U.S. 20030138488A1, U.S. 20030216307A1, U.S. Pat. No. 6,667, 060, WO 01/49249, WO 01/49311, WO 01/49249, WO 01/49311, and U.S. Pat. No. 5,877,224 materials which may include those described in WO04041195 (including the seal and enteric coating described therein) and pH-sensitive coatings that achieve delivery in the colon including those described in U.S. Pat. No. 4,910,021 and WO9001329. U.S. Pat. No. 4,910,021 describes using a pH-sensitive material to coat a capsule. WO9001329 describes using pH-sensitive coatings on beads containing acid, where the acid in the bead core prolongs dissolution of the pH-sensitive coating. U.S. Pat. No. 5,175,003 discloses a dual mechanism polymer mixture composed of pH-sensitive enteric materials and film-forming plasticizers capable of conferring permeability to the enteric material, for use in drug-delivery systems; a matrix pellet composed of a dual mechanism polymer mixture permeated with a drug and sometimes covering a pharmaceutically neutral nucleus; a membrane-coated pellet comprising a matrix pellet coated with a dual mechanism polymer mixture envelope of the same or different composition; and a pharmaceutical dosage form containing matrix pellets. The matrix pellet releases acid-soluble drugs by diffusion in acid pH and by disintegration at pH levels of nominally about 5.0 or higher.

The GCRA peptideds described herein may be formulated in the pH triggered targeted control release systems described in WO04052339. The agents described herein may be formulated according to the methodology described in any of WO03105812 (extruded hyrdratable polymers); WO0243767 (enzyme cleavable membrane translocators); WO03007913 and WO03086297 (mucoadhesive systems); WO02072075 (bilayer laminated formulation comprising pH lowering agent and absorption enhancer); WO04064769 (amidated polypeptides); WO05063156 (solid lipid suspension with pseudotropic and/or thixotropic properties upon melting); WO03035029 and WO03035041 (erodible, gastric retentive dosage forms); U.S. Pat. No. 5,007,790 and U.S. Pat. No. 5,972,389 (sustained release dosage forms); WO041 1271 1 (oral extended release compositions); WO05027878, WO02072033, and WO02072034 (delayed release compositions with natural or synthetic gum); WO05030182 (controlled release formulations with an ascending rate of release); WO05048998 (microencapsulation system); U.S. Pat. No. 5,952,314 (biopolymer); U.S. Pat. No. 5,108,758 (glassy amylose matrix delivery); U.S. Pat. No. 5,840,860 (modified starch based delivery). JP10324642 (delivery system comprising chitosan and gastric resistant material such as wheat gliadin or zein); U.S. Pat. No. 5,866,619 and U.S. Pat. No. 6,368,629 (saccharide containing polymer); U.S. Pat. No. 6,531,152 (describes a drug delivery system containing a water soluble core (Ca pectinate or other water-insoluble polymers) and outer coat which bursts (e.g. hydrophobic polymer-Eudragrit)); U.S. Pat. No. 6,234,464; U.S. Pat. No. 6,403,130 (coating with polymer containing casein and high methoxy pectin; WO0174 175 (Maillard reaction product); WO05063206 (solubility increasing formulation); WO040 19872 (transferring fusion proteins).

The GCRA peptides described herein may be formulated using gastrointestinal retention system technology (GIRES; Merrion Pharmaceuticals). GIRES comprises a controlled-release dosage form inside an inflatable pouch, which is placed in a drug capsule for oral administration. Upon dissolution of the capsule, a gas-generating system inflates the pouch in the stomach where it is retained for 16-24 hours, all the time releasing agents described herein.

The GCRA peptides described herein can be formulated in an osmotic device including the ones disclosed in U.S. Pat. No. 4,503,030, U.S. Pat. No. 5,609,590 and U.S. Pat. No. 5,358,502. U.S. Pat. No. 4,503,030 discloses an osmotic device for dispensing a drug to certain pH regions of the gastrointestinal tract. More particularly, the invention relates to an osmotic device comprising a wall formed of a semi-permeable pH sensitive composition that surrounds a compartment containing a drug, with a passageway through the wall connecting the exterior of the device with the compartment. The device delivers the drug at a controlled rate in the region of the gastrointestinal tract having a pH of less than 3.5, and the device self-destructs and releases all its drug in the region of the gastrointestinal tract having a pH greater than 3.5, thereby providing total availability for drug absorption. U.S. Pat. Nos. 5,609,590 and 5,358,502 disclose an osmotic bursting device for dispensing a beneficial agent to an aqueous environment. The device comprises a beneficial agent and osmagent surrounded at least in part by a semi-permeable membrane. The beneficial agent may also function as the osmagent. The semi-permeable membrane is permeable to water and substantially impermeable to the beneficial agent and osmagent. A trigger means is attached to the semi-permeable membrane (e.g., joins two capsule halves). The trigger means is activated by a pH of from 3 to 9 and triggers the eventual, but sudden, delivery of the beneficial agent. These devices enable the pH-triggered release of the beneficial agent core as a bolus by osmotic bursting.

Exemplary Agents for Combination Therapy

Analgesic Agents

The GCRA peptides described herein can be used in combination therapy with an analgesic agent, e.g., an analgesic compound or an analgesic polypeptide. These polypeptides and compounds can be administered with the GCRA peptides described herein (simultaneously or sequentially). They can also be optionally covalently linked or attached to an agent described herein to create therapeutic conjugates. Among the useful analgesic agents are: Ca channel blockers, 5HT receptor antagonists (for example 5HT3, 5HT4 and 5HT1 receptor antagonists), opioid receptor agonists (loperamide, fedotozine, and fentanyl), NK1 receptor antagonists, CCK receptor agonists (e.g., loxiglumide), NK1 receptor antagonists, NK3 receptor antagonists, norepinephrine-serotonin reuptake inhibitors (NSR1), vanilloid and cannabanoid receptor agonists, and sialorphin. Analgesics agents in the various classes are described in the literature.

Among the useful analgesic polypeptides are sialorphin-related polypeptides, including those comprising the amino acid sequence QHNPR (SEQ ID NO: 99), including: VQHNPR (SEQ ID NO: 100); VRQHNPR (SEQ ID NO: 101); VRGQHNPR (SEQ ID NO: 102); VRGPQHNPR (SEQ ID NO: 103); VRGPRQHNPR (SEQ ID NO: 104); VRGPRRQHNPR (SEQ ID NO: 105); and RQHNPR (SEQ ID NO: 106). Sialorphin-related polypeptides bind to neprilysin and inhibit neprilysin-mediated breakdown of substance P and Met-enkephalin. Thus, compounds or polypeptides that are inhibitors of neprilysin are useful analgesic agents which can be administered with the polypeptides described herein in a co-therapy or linked to the polypeptides described herein, e.g., by a covalent bond. Sialophin and related polypeptides are described in U.S. Pat. No. 6,589,750; U.S. 20030078200 A1; and WO 02/051435 A2.

Opioid receptor antagonists and agonists can be administered with the GCRA peptides described herein in co-therapy or linked to the agent described herein, e.g., by a covalent bond. For example, opioid receptor antagonists such as naloxone, naltrexone, methyl nalozone, nalmefene, cypridime, beta funaltrexamine, naloxonazine, naltrindole, and nor-binaltorphimine are thought to be useful in the treatment of IBS. It can be useful to formulate opioid antagonists of this type is a delayed and sustained release formulation such that initial release of the antagonist is in the mid to distal small intestine and/or ascending colon. Such antagonists are described in WO 01/32180 A2. Enkephalin pentapeptide (HOE825; Tyr-D-Lys-Gly-Phe-L-homoserine) (SEQ ID NO: 122) is an agonist of the mu and delta opioid receptors and is thought to be useful for increasing intestinal motility {Eur. J. Pharm. 219: 445, 1992), and this polypeptide can be used in conjunction with the polypeptides described herein. Also useful is trimebutine which is thought to bind to mu/delta/kappa opioid receptors and activate release of motilin and modulate the release of gastrin, vasoactive intestinal polypeptide, gastrin and glucagons. Kappa opioid receptor agonists such as fedotozine, asimadoline, and ketocyclazocine, and compounds described in WO03/097051 and WO05/007626 can be used with or linked to the polypeptides described herein. In addition, mu opioid receptor agonists such as morphine, diphenyloxylate, frakefamide (H-Tyr-D-Ala-Phe(F)-Phe-NH2; WO 01/019849 A1) (SEQ ID NO: 123) and loperamide can be used.

Tyr-Arg (kyotorphin) is a dipeptide that acts by stimulating the release of met-enkephalins to elicit an analgesic effect (J. Biol. Chem. 262:8165, 1987). Kyotorphin can be used with or linked to the GCRA peptides described herein.

Chromogranin-derived polypeptide (CgA 47-66; See, e.g., Ghia et al. 2004 Regulatory polypeptides 119:199) can be used with or linked to the GCRA peptides described herein.

CCK receptor agonists such as caerulein from amphibians and other species are useful analgesic agents that can be used with or linked to the GCRA peptides described herein.

Conotoxin polypeptides represent a large class of analgesic polypeptides that act at voltage gated calcium channels, NMDA receptors or nicotinic receptors. These polypeptides can be used with or linked to the polypeptides described herein. Peptide analogs of thymulin (FR Application 2830451) can have analgesic activity and can be used with or linked to the polypeptides described herein.

CCK (CCKa or CCKb) receptor antagonists, including loxiglumide and dexloxiglumide (the R-isomer of loxiglumide) (WO 88/05774) can have analgesic activity and can be used with or linked to the polypeptides described herein.

Other useful analgesic agents include 5-HT4 agonists such as tegaserod (Zelnorm®), mosapride, metoclopramide, zacopride, cisapride, renzapride, benzimidazolone derivatives such as BIMU 1 and BIMU 8, and lirexapride. Such agonists are described in: EP1321 142 A1, WO 03/053432A1, EP 505322 A1, EP 505322 B1, U.S. Pat. No. 5,510,353, EP 507672 A1, EP 507672 B1, and U.S. Pat. No. 5,273,983.

Calcium channel blockers such as ziconotide and related compounds described in, for example, EP625162B1, U.S. Pat. No. 5,364,842, U.S. Pat. No. 5,587,454, U.S. Pat. No. 5,824,645, U.S. Pat. No. 5,859,186, U.S. Pat. No. 5,994,305, U.S. Pat. No. 6,087,091, U.S. Pat. No. 6,136,786, WO 93/13128A1, EP 1336409A1, EP 835126 A1, EP 835126 B1, U.S. Pat. No. 5,795,864, U.S. Pat. No. 5,891,849, U.S. Pat. No. 6,054,429, WO 97/01351 A1, can be used with or linked to the polypeptides described herein.

Various antagonists of the NK-I, NK-2, and NK-3 receptors (for a review see Giardina et al. 2003. Drugs 6:758) can be can be used with or linked to the polypeptides described herein.

NK1 receptor antagonists such as: aprepitant (Merck & Co Inc), vofopitant, ezlopitant (Pfizer, Inc.), R-673 (Hoffmann-La Roche Ltd), SR-48968 (Sanofi Synthelabo), CP-122,721 (Pfizer, Inc.), GW679769 (Glaxo Smith Kline), TAK-637 (Takeda/Abbot), SR-14033, and related compounds described in, for example, EP 873753 A1, US 20010006972 A1, US 20030109417 A1, WO 01/52844 A1, can be used with or linked to the polypeptides described herein.

NK-2 receptor antagonists such as nepadutant (Menarini Ricerche SpA), saredutant (Sanoft-Synthelabo), GW597599 (Glaxo Smith Kline), SR-144190 (Sanoft-Synthelabo) and UK-290795 (Pfizer Inc) can be used with or linked to the polypeptides described herein.

NK3 receptor antagonists such as osanetant (SR-142801; Sanoft-Synthelabo), SSR-241586, talnetant and related compounds described in, for example, WO 02/094187 A2, EP 876347 A1, WO 97/21680 A1, U.S. Pat. No. 6,277,862, WO 98/1 1090, WO 95/28418, WO 97/19927, and Boden et al. (J Med. Chem. 39:1664-75, 1996) can be used with or linked to the polypeptides described herein.

Norepinephrine-serotonin reuptake inhibitors (NSRI) such as milnacipran and related compounds described in WO 03/077897 A1 can be used with or linked to the polypeptides described herein.

Vanilloid receptor antagonists such as arvanil and related compounds described in WO 01/64212 A1 can be used with or linked to the polypeptides described herein.

The analgesic polypeptides and compounds can be administered with the polypeptides and agonists described herein (simultaneously or sequentially). The analgesic agents can also be covalently linked to the polypeptides and agonists described herein to create therapeutic conjugates. Where the analgesic is a polypeptide and is covalently linked to an agent described herein the resulting polypeptide may also include at least one trypsin cleavage site. When present within the polypeptide, the analgesic polypeptide may be preceded by (if it is at the carboxy terminus) or followed by (if it is at the amino terminus) a trypsin cleavage site that allows release of the analgesic polypeptide.

In addition to sialorphin-related polypeptides, analgesic polypeptides include: AspPhe, endomorphin-1, endomorphin-2, nocistatin, dalargin, lupron, ziconotide, and substance P.

Agents to Treat Gastrointestinal Disorders

Examples of additional therapeutic agents to treat gastrointestinal and other disorders include agents to treat constipation (e.g., a chloride channel activator such as the bicylic fatty acid, Lubiprostone (formerly known as SPI-0211; Sucampo Pharmaceuticals, Inc.; Bethesda, Md.), a laxative (e.g. a bulk-forming laxative (e.g. nonstarch polysaccharides, Colonel Tablet (polycarbophil calcium), Plantago Ovata®, Equalactin® (Calcium Polycarbophil)), fiber (e.g. FIBERCON® (Calcium Polycarbophil), an osmotic laxative, a stimulant laxative (such as diphenylmethanes (e.g. bisacodyl), anthraquinones (e.g. cascara, senna), and surfactant laxatives (e.g. castor oil, docusates), an emollient/lubricating agent (such as mineral oil, glycerine, and docusates), MiraLax (Braintree Laboratories, Braintree Mass.), dexloxiglumide (Forest Laboratories, also known as CR 2017 Rottapharm (Rotta Research Laboratorium SpA)), saline laxatives, enemas, suppositories, and CR 3700 (Rottapharm (Rotta Research Laboratorium SpA); acid reducing agents such as proton pump inhibitors (e.g., omeprazole (Prilosec®), esomeprazole (Nexium®), lansoprazole (Prevacid®), pantoprazole (Protonix®) and rabeprazole (Aciphex®)) and Histamine H2-receptor antagonist (also known as H2 receptor blockers including cimetidine, ranitidine, famotidine and nizatidine); prokinetic agents including itopride, octreotide, bethanechol, metoclopramide (Reglan®), domperidone (Motilium®), erythromycin (and derivatives thereof) or cisapride (Propulsid®); Prokineticin polypeptides homologs, variants and chimeras thereof including those described in U.S. Pat. No. 7,052,674 which can be used with or linked to the polypeptides described herein; pro-motility agents such as the vasostatin-derived polypeptide, chromogranin A (4-16) (See, e.g., Ghia et al. 2004 Regulatory polypeptides 121:31) or motilin agonists (e.g., GM-611 or mitemcinal fumarate) or nociceptin/Orphanin FQ receptor modulators (US20050169917); other peptides which can bind to and/or activate GC-C including those described in US20050287067; complete or partial 5HT (e.g. 5HT1, 5HT2, 5HT3, 5HT4) receptor agonists or antagonists (including 5HT1A antagonists (e.g. AGI-OO1 (AGI therapeutics), 5HT2B antagonists (e.g. PGN 1091 and PGNl 164 (Pharmagene Laboratories Limited), and 5HT4 receptor agonists (such as tegaserod (ZELNORM®), prucalopride, mosapride, metoclopramide, zacopride, cisapride, renzapride, benzimidazolone derivatives such as BIMU 1 and BIMU 8, and lirexapride). Such agonists/modulators are described in: EP1321142 A1, WO 03/053432A1, EP 505322 A1, EP 505322 B1, U.S. Pat. No. 5,510,353, EP 507672 A1, EP 507672 B1, U.S. Pat. No. 5,273,983, and U.S. Pat. No. 6,951, 867); 5HT3 receptor agonists such as MKC-733; and 5HT3 receptor antagonists such as DDP-225 (MC1-225; Dynogen Pharmaceuticals, Inc.), cilansetron (Calmactin®), alosetron (Lotronex®), Ondansetron HCl (Zofran®), Dolasetron (ANZEMET®), palonosetron (Aloxi®), Granisetron (Kytril®), YM060 (ramosetron; Astellas Pharma Inc.; ramosetron may be given as a daily dose of 0.002 to 0.02 mg as described in EP01588707) and ATI-7000 (Aryx Therapeutics, Santa Clara Calif.); muscarinic receptor agonists; anti-inflammatory agents; antispasmodics including but not limited to anticholinergic drugs (like dicyclomine (e.g. Colimex®, Formulex®, Lomine®, Protylol®, Visceral®, Spasmoban®, Bentyl®, Bentylol®), hyoscyamine (e.g. IB-Stat®, Nulev®, Levsin®, Levbid®, Levsinex Timecaps®, Levsin/SL®, Anaspaz®, A-Spas S/L®, Cystospaz®, Cystospaz-M®, Donnamar®, Colidrops Liquid Pediatric®, Gastrosed®, Hyco Elixir®, Hyosol®, Hyospaz®, Hyosyne®, Losamine®, Medispaz®, Neosol®, Spacol®, Spasdel®, Symax®, Symax SL®), Donnatal (e.g. Donnatal Extentabs®), clidinium (e.g. Quarzan, in combination with Librium=Librax), methantheline (e.g. Banthine), Mepenzolate (e.g. Cantil), homatropine (e.g. hycodan, Homapin), Propantheline bromide (e.g. Pro-Banthine), Glycopyrrolate (e.g. Robinul®, Robinul Forte®), scopolamine (e.g. Transderm-Scop®, Transderm-V®), hyosine-N-butylbromide (e.g. Buscopan®), Pirenzepine (e.g. Gastrozepin®) Propantheline Bromide (e.g. Propanthel®), dicycloverine (e.g. Merbentyl®), glycopyrronium bromide (e.g. Glycopyrrolate®), hyoscine hydrobromide, hyoscine methobromide, methanthelinium, and octatropine); peppermint oil; and direct smooth muscle relaxants like cimetropium bromide, mebeverine (DUSPATAL®, DUSPATALIN®, COLOFAC MR®, COLOTAL®), otilonium bromide (octilonium), pinaverium (e.g. Dicetel® (pinaverium bromide; Solvay S. A.)), Spasfon® (hydrated phloroglucinol and trimethylphloroglucinol) and trimebutine (including trimebutine maleate (Modulon®); antidepressants, including but not limited to those listed herein, as well as tricyclic antidepressants like amitriptyline desipramine (Norpramin®), imipramine (Tofranil®), amoxapine (Asendin®), nortriptyline; the selective serotonin reuptake inhibitors (SSRTs) like paroxetine (Paxil®), fluoxetine (Prozac®), sertraline (Zoloft®), and citralopram (Celexa®); and others like doxepin (Sinequan®) and trazodone (Desyrel®); centrally-acting analgesic agents such as opioid receptor agonists, opioid receptor antagonists (e.g., naltrexone); agents for the treatment of Inflammatory bowel disease; agents for the treatment of Crohn's disease and/or ulcerative colitis (e.g., alequel (Enzo Biochem, Inc.; Farmingsale, N.Y.), the anti-inflammatory polypeptide RDP58 (Genzyme, Inc.; Cambridge, Mass.), and TRAFICET-EN™ (ChemoCentryx, Inc.; San Carlos, Calif.); agents that treat gastrointestinal or visceral pain; agents that increase cGMP levels (as described in US20040121994) like adrenergic receptor antagonists, dopamine receptor agonists and PDE (phosphodiesterase) inhibitors including but not limited to those disclosed herein; purgatives that draw fluids to the intestine (e.g., VISICOL®, a combination of sodium phosphate monobasic monohydrate and sodium phosphate dibasic anhydrate); Corticotropin Releasing Factor (CRF) receptor antagonists (including NBI-34041 (Neurocrine Biosciences, San Diego, Calif.), CRH9-41, astressin, R121919 (Janssen Pharmaceutica), CP154,526, NBI-27914, Antalarmin, DMP696 (Bristol-Myers Squibb) CP-316,311

(Pfizer, Inc.), SB723620 (GSK), GW876008 (Neurocrine/ Glaxo Smith Kline), ONO-2333Ms (Ono Pharmaceuticals), TS-041 (Janssen), AAG561 (Novartis) and those disclosed in U.S. Pat. No. 5,063,245, U.S. Pat. No. 5,861,398, US20040224964, US20040198726, US20040176400, US20040171607, US20040110815, US20040006066, and US20050209253); glucagon-like polypeptides (glp-1) and analogues thereof (including exendin-4 and GTP-010 (Gastrotech Pharma A)) and inhibitors of DPP-IV (DPP-IV mediates the inactivation of glp-1); tofisopam, enantiomerically-pure R-tofisopam, and pharmaceutically-acceptable salts thereof (US 20040229867); tricyclic anti-depressants of the dibenzothiazepine type including but not limited to Dextofisopam® (Vela Pharmaceuticals), tianeptine (Stablon®) and other agents described in U.S. Pat. No. 6,683, 072; (E)-4 (1,3bis(cyclohexylmethyl)-1,2,34,-tetrahydro-2, 6-diono-9H-purin-8-yl)cinnamic acid nonaethylene glycol methyl ether ester and related compounds described in WO 02/067942; the probiotic PROBACTRIX® (The BioBalance Corporation; New York, N.Y.) which contains microorganisms useful in the treatment of gastrointestinal disorders; antidiarrheal drugs including but not limited to loperamide (Imodium, Pepto Diarrhea), diphenoxylate with atropine (Lomotil, Lomocot), cholestyramine (Questran, Cholybar), atropine (Co-Phenotrope, Diarsed, Diphenoxylate, Lofene, Logen, Lonox, Vi-Atro, atropine sulfate injection) and Xifaxan® (rifaximin; *Salix* Pharmaceuticals Ltd), TZP-201 (Tranzyme Pharma Inc.), the neuronal acetylcholine receptor (nAChR) blocker AGI-004 (AGI therapeutics), and bismuth subsalicylate (Pepto-bismol); anxiolytic drugs including but not limited toAtivan (lorazepam), alprazolam (Xanax®), chlordiazepoxide/clidinium (Librium®, Librax®), clonazepam (Klonopin®), clorazepate (Tranxene®), diazepam (Valium®), estazolam (ProSom®), flurazepam (Dalmane®), oxazepam (Serax®), prazepam (Centrax®), temazepam (Restoril®), triazolam (Halcion®; Bedelix® (Montmorillonite beidellitic; Ipsen Ltd), Solvay SLV332 (ArQule Inc), YKP (SK Pharma), Asimadoline (Tioga Pharmaceuticals/Merck), AGI-003 (AGI Therapeutics); neurokinin antagonists including those described in US20060040950; potassium channel modulators including those described in U.S. Pat. No. 7,002, 015; the serotonin modulator AZD7371 (AstraZeneca Plc); M3 muscarinic receptor antagonists such as darifenacin (Enablex; Novartis AG and zamifenacin (Pfizer); herbal and natural therapies including but not limited to acidophilus, chamomile tea, evening primrose oil, fennel seeds, wormwood, comfrey, and compounds of Bao-Ji-Wan (magnolol, honokiol, imperatorin, and isoimperatorin) as in U.S. Pat. No. 6,923,992; and compositions comprising lysine and an anti-stress agent for the treatment of irritable bowel syndrome as described in EPO 1550443.

Insulin and Insulin Modulating Agents

The GCRA peptides described herein can be used in combination therapy with insulin and related compounds including primate, rodent, or rabbit insulin including biologically active variants thereof including allelic variants, more preferably human insulin available in recombinant form. Sources of human insulin include pharmaceutically acceptable and sterile formulations such as those available from Eli Lilly (Indianapolis, Ind. 46285) as Humulin™ (human insulin rDNA origin). See, the THE PHYSICIAN'S DESK REFERENCE, 55.sup.th Ed. (2001) Medical Economics, Thomson Healthcare (disclosing other suitable human insulins).

The GCRA peptides described herein can also be used in combination therapy with agents that can boost insulin effects or levels of a subject upon administration, e.g. glipizide and/ or rosiglitazone. The polypeptides and agonistsdescribed herein can be used in combitherapy with SYMLIN® (pramlintide acetate) and Exenatide® (synthetic exendin-4; a 39 aa polypeptide).

Agents for the Treatment of Postoperative Ileus

The GCRA peptides described herein can also be used in combination therapy with agents (e.g., Entereg™ (alvimopan; formerly called ado lor/ADL 8-2698), conivaptan and related agents describe in U.S. Pat. No. 6,645,959) used for the treatment of postoperative ileus and other disorders.

Anti-Hypertensive Agents

The GCRA peptides described herein can be used in combination therapy with an anti-hypertensive agent including but not limited to: (1) diuretics, such as thiazides, including chlorthalidone, chlorthiazide, dichlorophenamide, hydroflumethiazide, indapamide, polythiazide, and hydrochlorothiazide; loop diuretics, such as bumetanide, ethacrynic acid, furosemide, and torsemide; potassium sparing agents, such as amiloride, and triamterene; carbonic anhydrase inhibitors, osmotics (such as glycerin) and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as benazepril; captopril; ceranapril; cilazapril; delapril; enalapril; enalopril; fosinopril; imidapril; lisinopril; losinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, and the like; (8) angiotensin II receptor antagonists such as aprosartan, candesartan, eprosartan, irbesartan, losartan, olmesartan, pratosartan, tasosartan, telmisartan, valsartan, and EXP-3137, FI6828K, and RNH6270, and the like; (9) α/β adrenergic blockers such as nipradilol, arotinolol and amosulalol, and the like; (10) alpha 1 blockers, such as terazosin, urapidil, prazosin, tamsulosin, bunazosin, trimazosin, doxazosin, naftopidil, indoramin, WHP 164, and XENO1O, and the like; (11) alpha 2 agonists such as lofexidine, tiamenidine, moxonidine, rilmenidine and guanobenz, and the like; (12) aldosterone inhibitors, and the like; and (13) angiopoietin-2-binding agents such as those disclosed in WO03/030833. Specific anti-hypertensive agents that can be used in combination with polypeptides and agonists described herein include, but are not limited to: diuretics, such as thiazides (e.g., chlorthalidone, cyclothiazide (CAS RN 2259-96-3), chlorothiazide (CAS RN 72956-09-3, which may be prepared as disclosed in U.S. Pat. No. 2,809,194), dichlorophenamide, hydroflumethiazide, indapamide, polythiazide, bendroflumethazide, methyclothazide, polythiazide, trichlormethazide, chlorthalidone, indapamide, metolazone, quinethazone, althiazide (CAS RN 5588-16-9, which may be prepared as disclosed in British Patent No. 902,658), benzthiazide (CAS RN 91-33-8, which may be prepared as disclosed in U.S. Pat. No. 3,108,097), buthiazide (which may be prepared as disclosed in British Patent Nos. 861,367), and hydrochlorothiazide), loop diuretics (e.g. bumetanide, ethacrynic acid, furosemide, and torasemide), potassium sparing agents (e.g. amiloride, and triamterene (CAS Number 396-01-O)), and aldosterone antagonists (e.g. spironolactone (CAS Number 52-01-7), epirenone, and the like); β-adrenergic blockers such as Amiodarone (Cordarone, Pacerone), bunolol hydrochloride (CAS RN 31969-05-8, Parke-Davis), acebutolol (±N-[3-Acetyl-4-[2-hydroxy-3-[(1 methylethyl)amino]propoxy]phenyl]-butanamide, or (±)-3'-Acetyl-4'-[2-hydroxy-3-(isopropylamino) propoxy]butyranilide), acebutolol hydrochloride (e.g. Sectral®, Wyeth-Ayerst), alprenolol hydrochloride (CAS RN 13707-88-5 see Netherlands Patent Application No. 6,605,692), atenolol (e.g. Tenormin®, Astra-Zeneca), carteolol hydrochloride (e.g. Cartrol® Filmtab®, Abbott), Celiprolol hydrochloride (CAS RN 57470-78-7, also see in U.S. Pat. No. 4,034,009), cetamolol hydrochloride (CAS RN 77590-95-5, see also U.S. Pat. No. 4,059,622), labetalol hydrochloride (e.g. Normodyne®, Schering), esmolol hydrochloride (e.g. Brevibloc®, Baxter), levobetaxolol hydrochloride (e.g. Betaxon™ Ophthalmic Suspension, Alcon), levobunolol hydrochloride (e.g. Betagan® Liquifilm® with C CAP® Compliance Cap, Allergan), nadolol (e.g. Nadolol, Mylan), practolol (CAS RN 6673-85-4, see also U.S. Pat. No. 3,408,387), propranolol hydrochloride (CAS RN 318-98-9), sotalol hydrochloride (e.g. Betapace AF™, Berlex), timolol (2-Propanol,1-[(1,1-dimethylethyl) amino]-3-[[4-4(4-morpholinyl)-1,2,5-thiadiazol-3-yl]oxy]-, hemihydrate, (S)-, CAS RN 91524-16-2), timolol maleate (S)-I-[(1,1-dimethylethyl)amino]-3-[[4-(4-morpholinyl)-1, 2,5-thiadiazol-3-yl]oxy]-2-propanol (Z)-2-butenedioate (1:1) salt, CAS RN 26921-17-5), bisoprolol (2-Propanol, 1-[4-[[2-(1-methylethoxy)ethoxy]-methyl]phenoxyl]-3-[(1-meth-ylethyl)amino]-, (±), CAS RN 66722-44-9), bisoprolol fumarate (such as (±)-1-[4-[[2-(1-Methylethoxy)ethoxy]methyl]phenoxy]-3-[(1-methylethyl)amino]-2-propanol (E)-2-butenedioate (2:1) (salt), e.g., Zebeta™, Lederle Consumer), nebivalol (2H-1-Benzopyran-2-methanol, αα'-[iminobis (methylene)]bis[6-fluoro-3,4-dihydro-, CAS RN 99200-09-6 see also U.S. Pat. No. 4,654,362), cicloprolol hydrochloride, such 2-Propanol, 1-[4-[2-(cyclopropylmethoxy)ethoxy]phenoxy]-3-[1-methylethyl)amino]-, hydrochloride, A.A.S. RN 63686-79-3), dexpropranolol hydrochloride (2-Propanol,1-[1-methylethy)-amino]-3-(1-naphthalenyloxy)-hydrochloride (CAS RN 13071-11-9), diacetolol hydrochloride (Acetamide, N-[3-acetyl-4-[2-hydroxy-3-[(1-methyl-ethyl)amino] propoxy][phenyl]-, monohydrochloride CAS RN 69796-04-9), dilevalol hydrochloride (Benzamide, 2-hydroxy-5-[l-hydroxy-2-[1-methyl-3-phenylpropyl)amino]ethyl]-, monohydrochloride, CAS RN 75659-08-4), exaprolol hydrochloride (2-Propanol, 1-(2-cyclohexylphenoxy)-3-[(1-meth-ylethyl)amino]hydrochloride CAS RN 59333-90-3), flestolol sulfate (Benzoic acid, 2-fluoro-,3-[[2-[aminocarbonyl) amino]-dimethylethyl]amino]-2-hydroxypropyl ester, (+)- sulfate (1:1) (salt), CAS RN 88844-73-9; metalol hydrochloride (Methanesulfonamide, N-[4-[1-hydroxy-2-(methylamino)propyl]phenyl]-, monohydrochloride CAS RN 7701-65-7), metoprolol 2-Propanol, 1-[4-(2-methoxyethyl)phenoxy]-3-[1-methylethyl)amino]-; CAS RN 37350-58-6), metoprolol tartrate (such as 2-Propanol, 1-[4-(2-methoxyethyl)phenoxy]-3-[(1-methylethyl)amino]-, e.g., Lopressor®, Novartis), pamatolol sulfate (Carbamic acid, [2-[4-[2-hydroxy-3-[(1-methylethyl)amino]propoxyl]phenyl]-ethyl]-, methyl ester, (±) sulfate (salt) (2:1), CAS RN 59954-01-7), penbutolol sulfate (2-Propanol, 1-(2-cyclopentylphenoxy)-3-[1,1-dimethyle-thyl)amino]1, (S)-, sulfate (2:1) (salt), CAS RN 38363-32-5), practolol (Acetamide, N-[4-[2-hydroxy-3-[(1-methylethyl)amino]-propoxy]phenyl]-, CAS RN 6673-35-4;) tiprenolol hydrochloride (Propanol, 1-[(1-methylethyl)amino]-3-[2-(methylthio)-phenoxy]-, hydrochloride, (±), CAS RN 39832-43-4), tolamolol (Benzamide, 4-[2-[[2-hydroxy-3-(2-methylphenoxy)-propyl]amino]ethoxyl]-, CAS RN 38103-61-6), bopindolol, indenolol, pindolol, propanolol, tertatolol, and tilisolol, and the like; calcium channel blockers such as besylate salt of amlodipine (such as 3-ethyl-5-methyl-2-(2-aminoethoxymethyl)-4-(2-chlorophenyl)-1,4-dihydro-6-methyl-3,5-pyridinedicarboxylate benzenesulphonate, e.g., Norvasc®, Pfizer), clentiazem maleate (1,5-Benzothiazepin-4(5H)-one, 3-(acetyloxy)-8-chloro-5-[2-(dimethylamino)ethyl]-2,3-dihydro-2-(4-methoxyphenyl)-(2S-cis)-, (Z)-2-butenedioate (1:1), see also U.S. Pat. No. 4,567,195), isradipine (3,5-Pyridinedicarboxylic acid, 4-(4-benzofurazanyl)-1,4-dihydro-2,6-dimethyl-, methyl 1-methylethyl ester, (±)-4(4-benzofurazanyl)-1,4-dihydro-2,6-dimethyl-3,5-pyridinedicarboxylate, see also U.S. Pat. No. 4,466,972); nimodipine (such as is isopropyl (2-methoxyethyl) 1,4-dihydro-2,6-dimethyl-4-(3-nitrophenyl)-3,5-pyridine-dicarboxylate, e.g. Nimotop®, Bayer), felodipine (such as ethyl methyl 4-(2,3-dichlorophenyl)-1,4-dihydro-2,6-dimethyl-3,5-pyridinedicarboxylate-, e.g. Plendil® Extended-Release, Astra-Zeneca LP), nilvadipine (3,5-Pyridinedicarboxylic acid, 2-cyano-1,4-dihydro-6-methyl-4-(3-nitrophenyl)-,3-methyl 5-(1-methylethyl)ester, also see U.S. Pat. No. 3,799,934), nifedipine (such as 3,5-pyridinedicarboxylic acid, 1,4-dihydro-2,6-dimethyl-4-(2-nitrophenyl)-, dimethyl ester, e.g., Procardia XL® Extended Release Tablets, Pfizer), diltiazem hydrochloride (such as 1,5-Benzothiazepin-4(5H)-one,3-(acetyloxy)-5[2-(dimethylamino)ethyl]-2,-3-dihydro-2(4-methoxyphenyl)-, monohydrochloride, (+)-cis., e.g., Tiazac®, Forest), verapamil hydrochloride (such as benzeneacetonitrile, (alpha)-[[3-[[2-(3,4-dimethoxyphenyl)ethyl] methylamino]propyl]-3,4-dimethoxy-(alpha)-(1-methyl-ethyl) hydrochloride, e.g., Isoptin® SR, Knoll Labs), teludipine hydrochloride (3,5-Pyridinedicarboxylic acid, 2-[(dimethylamino)methyl]4-[2-[(1E)-3-(1,1-dimethyl-ethoxy)-3-oxo-1-propenyl]phenyl]-1,4-dihydro-6-methyl-, diethyl ester, monohydrochloride) CAS RN 108700-03-4), belfosdil (Phosphonic acid, [2-(2-phenoxy ethyl)-1,3-propane-diyl]bis-, tetrabutyl ester CAS RN 103486-79-9), fostedil (Phosphonic acid, [[4-(2-benzothiazolyl)phenyl]methyl]-, diethyl ester CAS RN 75889-62-2), aranidipine, azelnidipine, barnidipine, benidipine, bepridil, cinaldipine, clevidipine, efonidipine, gallopamil, lacidipine, lemildipine, lercanidipine, monatepil maleate (1-piperazinebutanamide, N-(6,11-dihydrodibenzo(b,e)thiepin-11-yl)$_4$-(4-fluorophenyl)-, (+)-, (Z)-2-butenedioate (1:1) (±)-N-(6,11-Dihydrodibenzo(b,e)thiep-in-1'-yl)-4-(p-fluorophenyl)-1-piperazinebutyramide maleate (1:1) CAS RN 132046-06-1), nicardipine, nisoldipine, nitrendipine, manidipine, pranidipine, and the like; T-channel calcium antagonists such as mibefradil; angiotensin converting enzyme (ACE) inhibitors such as benazepril, benazepril hydrochloride (such as 3-[[1-(ethoxycarbonyl)-3-phenyl-(1S)-propyl]amino]-2,3,4,5-tetrahydro-2-oxo-1H-1-(3S)-benzazepine-1-acetic acid monohydrochloride, e.g., Lotrel®, Novartis), captopril (such as 1-[(2S)-3-mercapto-2-methylpropionyl]-L-proline, e.g., Captopril, Mylan, CAS RN 62571-86-2 and others disclosed in U.S. Pat. No. 4,046,889), ceranapril (and others disclosed in U.S. Pat. No. 4,452,790), cetapril (alacepril, Dainippon disclosed in Eur. Therap. Res. 39:671 (1986); 40:543 (1986)), cilazapril (Hoffman-LaRoche) disclosed in J. Cardiovasc. Pharmacol. 9:39 (1987), indalapril (delapril hydrochloride (2H-1,2,4-Benzothiadiazine-7-sulfonamide, 3-bicyclo [2.2.1]hept-5-en-2-yl-6-chloro-3,4-dihydro-, 1,1-dioxide CAS RN 2259-96-3); disclosed in U.S. Pat. No. 4,385,051), enalapril (and others disclosed in U.S. Pat. No. 4,374,829), enalapril, enalaprilat, fosinopril, ((such as L-proline, 4-cyclohexyl-1-[[[2-methyl-1-(1-oxopropoxy) propoxy](4-phenylbutyl)phosphinyl]acetyl]-, sodium salt, e.g., Monopril, Bristol-Myers Squibb and others disclosed in U.S. Pat. No. 4,168,267), fosinopril sodium (L-Proline, 4-cyclohexyl-1-[[(R)-[(1S)-2-methyl-1-(1-ox-opropoxy)propox), imidapril, indolapril (Schering, disclosed in J. Cardiovasc. Pharmacol. 5:643, 655 (1983)), lisinopril (Merck), losinopril, moexipril, moexipril hydrochloride (3-Isoquinolinecarboxylic acid, 2-[(2S)-2-[[(1S)-1-(ethoxycarbonyl)-3-phenylpropyl]amino]-1-oxopropyl]-1,-2,3,4-tetrahydro-6,7-dimethoxy-, monohydrochloride, (3S)-CAS RN 82586-52-5), quinapril, quinaprilat, ramipril (Hoechsst) disclosed in EP 79022 and Curr. Ther. Res. 40:74 (1986), perindopril erbumine (such as 2S,3aS,7aS-1-[(S)—N—[(S)-1-Carboxybutyl]alanyl-jhexahydro^-indolinecarboxylic acid, 1-ethyl ester, compound with tert-butylamine (1:1), e.g., Aceon®, Solvay), perindopril (Servier, disclosed in Eur. J. din. Pharmacol. 31:519 (1987)), quanipril (disclosed in U.S. Pat. No. 4,344,949), spirapril (Schering, disclosed in Acta. Pharmacol. Toxicol. 59 (Supp. 5): 173 (1986)), tenocapril, trandolapril, zofenopril (and others disclosed in U.S. Pat. No. 4,316,906), rentiapril (fentiapril, disclosed in Clin. Exp. Pharmacol. Physiol. 10:131 (1983)), pivopril, YS980, teprotide (Bradykinin potentiator BPP9a CAS RN 35115-60-7), BRL 36,378 (Smith Kline Beecham, see EP80822 and EP60668), MC-838 (Chugai, see CA. 102:72588v and Jap. J. Pharmacol. 40:373 (1986), CGS 14824 (Ciba-Geigy, 3-([1-ethoxycarbonyl-3-phenyl-(1S)-propyl]amino)-2,3,4,5-tetrahydro-2-ox-o-1-(3S)-benzazepine-1-acetic acid HCl, see U.K. Patent No. 2103614), CGS 16,617 (Ciba-Geigy, 3(S)-[[(1S)-5-amino-1-carboxypentyl]amino]-2,3,4,-5-tetrahydro-2-oxo-1H-1-benzazepine-1-ethanoic acid, see U.S. Pat. No. 4,473,575), Ru 44570 (Hoechst, see Arzneimittelforschung 34:1254 (1985)), R 31-2201 (Hoffman-LaRoche see FEBS Lett. 165:201 (1984)), CI925 (Pharmacologist 26:243, 266 (1984)), WY-44221 (Wyeth, see J. Med. Chem. 26:394 (1983)), and those disclosed in US2003006922 (paragraph 28), U.S. Pat. No. 4,337,201, U.S. Pat. No. 4,432,971 (phosphonamidates); neutral endopeptidase inhibitors such as omapatrilat (Vanlev®), CGS 30440, cadoxatril and ecadotril, fasidotril (also known as aladotril or alatriopril), sampatrilat, mixanpril, and gemopatrilat, AVE7688, ER4030, and those disclosed in U.S. Pat. No. 5,362,727, U.S. Pat. No. 5,366,973, U.S. Pat. No. 5,225,401, U.S. Pat. No. 4,722,810, U.S. Pat. No. 5,223,516, U.S. Pat. No. 4,749,688, U.S. Pat. No. 5,552,397, U.S. Pat. No. 5,504,080, U.S. Pat. No. 5,612,359, U.S. Pat. No. 5,525, 723, EP0599444, EP0481522, EP0599444, EP0595610, EP0534363, EP534396, EP534492, EP0629627; endothelin antagonists such as tezosentan, A308165, and YM62899, and the like; vasodilators such as hydralazine (apresoline), clonidine (clonidine hydrochloride (1H-Imidazol-2-amine, N-(2, 6-dichlorophenyl)4,5-dihydro-, monohydrochloride CAS RN 4205-91-8), catapres, minoxidil (loniten), nicotinyl alcohol (roniacol), diltiazem hydrochloride (such as 1,5-Benzothiazepin-4(5H)-one,3-(acetyloxy)-5[2-(dimethylamino) ethyl]-2,-3-dihydro-2(4-methoxyphenyl)-, monohydrochloride, (+)-cis, e.g., Tiazac®, Forest), isosorbide dinitrate (such as 1,4:3,6-dianhydro-D-glucitol 2,5-dinitrate e.g., Isordil® Titradose®, Wyeth-Ayerst), sosorbide mononitrate (such as 1,4:3,6-dianhydro-D-glucito-1,5-nitrate, an organic nitrate, e.g., Ismo®, Wyeth-Ayerst), nitroglycerin (such as 2,3 propanetriol trinitrate, e.g., Nitrostat® Parke-Davis), verapamil hydrochloride (such as benzeneacetonitrile, (±)-(alpha)[3-[[2-(3,4 dimethoxypheny Dethyl] methylamino]propyl]-3,4-dimethoxy-(alpha)-(1-methylethyl)hydrochloride, e.g., Covera HS® Extended-Release, Searle), chromonar (which may be prepared as disclosed in U.S. Pat. No. 3,282,938), clonitate (Annalen 1870 155), droprenilamine (which may be prepared as disclosed in DE2521113), lidoflazine (which may be prepared as disclosed in U.S. Pat. No. 3,267,104); prenylamine (which may be prepared as disclosed in U.S. Pat. No. 3,152,173), propatyl nitrate (which may be prepared as disclosed in French Patent No. 1,103,113), mioflazine hydrochloride (1-piperazineacetamide, 3-(aminocarbonyl)-4-[4,4-bis(4-fluorophenyl)butyl]-N-(2,6-dichlorophenyl)-, dihydrochloride CAS RN 83898-67-3), mixidine (Benzeneethanamine, 3,4-dimethoxy-N-(1-methyl-2-pyrrolidinylidene)-Pyrrolidine, 2-[(3,4-dimethoxyphenethyl)imino]-1-methyl-1-Methyl-2-[(3,4-dimethoxyphenethyl)imino]pyrrolidine CAS RN 27737-38-8), molsidomine (1,2,3-Oxadiazolium, 5-[(ethoxycarbonyl)amino]-3-(4-morpholinyl)-, inner salt CAS RN 25717-80-0), isosorbide mononitrate (D-Glucito-1, 1,4:3,6-dianhydro-, 5-nitrate CAS RN 16051-77-7), erythrityl tetranitrate (1,2,3,4-Butanetetrol, tetranitrate, (2R,3S)-rel-CAS RN 7297-25-8), clonitrate(1,2-Propanediol, 3-chloro-, dinitrate (7CI, 8CI, 9CI) CAS RN 2612-33-1), dipyridamole Ethanol, 2,2',2",2"'-[(4,8-di-1-piperidinylpyrimido[5,4-d]pyrimidine-2,6-diyl)dinitrilo]tetrakis-CAS RN 58-32-2), nicorandil (CAS RN 65141-46-0 3-), pyridinecarboxamide (N-[2-(nitrooxy)ethyl]-Nisoldipine-3,5-Pyridinedicarboxylic acid, 1,4-dihydro-2,6-dimethyl-4-(2-nitrophenyl)-, methyl 2-methylpropyl ester CAS RN 63675-72-9), nifedipine-3,5-Pyridinedicarboxylic acid, 1,4-dihydro-2, 6-dimethyl-4-(2-nitrophenyl)-, dimethyl ester CAS RN 21829-25-4), perhexyline maleate (Piperidine, 2-(2,2-dicyclohexylethyl)-, (2Z)-2-butenedioate (1:1) CAS RN 6724-53-4), oxprenolol hydrochloride (2-Propanol, 1-[(1-methylethyl)amino]-3-[2-(2-propenyloxy)phenoxy]-, hydrochloride CAS RN 6452-73-9), pentrinitrol (1,3-Propanediol, 2,2-bis[(nitrooxy)methyl]-, mononitrate (ester) CAS RN 1607-17-6), verapamil (Benzeneacetonitrile, α-[3-[[2-(3,4-dimethoxyphenyl)ethyl]-methylamino]propyl]-3,4-dimethoxy-α-(1-methylethyl)-CAS RN 52-53-9) and the like; angiotensin II receptor antagonists such as, aprosartan, zolasartan, olmesartan, pratosartan, FI6828K, RNH6270, candesartan (1H-Benzimidazole-7-carboxylic acid, 2-ethoxy-1-[[2'-(1H-tetrazol-5-yl)[1,1'-biphenyl]4-yl]methyl]-CAS RN 139481-59-7), candesartan cilexetil (cyclohexylcarbonyloxy)ethyl-2-ethoxy-1-[[2'-(1H-tetrazol-5-yl) biphenyl-4-yl]-1H-benzimidazole carboxylate, CAS RN 145040-37-5, U.S. Pat. No. 5,703,110 and U.S. Pat. No. 5,196,444), eprosartan (3-[1-4-carboxyphenylmethyl)-2-n-butyl-imidazol-5-yl]-(2-thienylmethyl) propenoic acid, U.S. Pat. No. 5,185,351 and U.S. Pat. No. 5,650,650), irbesartan (2-n-butyl-3-[[2'-(1 h-tetrazol-5-yl)biphenyl-4-yl]methyl]1, 3-diazaspiro[4,4]non-1-en-4-one, U.S. Pat. No. 5,270,317 and U.S. Pat. No. 5,352,788), losartan (2-N-butyl-4-chloro-5-hydroxymethyl-1-[(2'-(1H-tetrazol-5-yl)biphenyl-4-yl)-methyl]imidazole, potassium salt, U.S. Pat. No. 5,138,069, U.S. Pat. No. 5,153,197 and U.S. Pat. No. 5,128,355), tasosartan (5,8-dihydro-2,4-dimethyl-8-[(2'-(1H-tetrazol-5-yl)[1,r-biphenyl]4-yl)methyl]-pyrido[2,3-d]pyrimidin-7(6H)-one, U.S. Pat. No. 5,149,699), telmisartan (4'-[(1,4-dimethyl-2'-propyl-(2,6'-bi-1H-benzimidazol)-r-yl)]-[1,1'-biphenyl]-2-carboxylic acid, CAS RN 144701-48-4, U.S. Pat. No. 5,591, 762), milfasartan, abitesartan, valsartan (Diovan® (Novartis), (S)—N-valeryl-N-[[2'-(1H-tetrazol-5-yl)biphenyl-4-yl)methyl]valine, U.S. Pat. No. 5,399,578), EXP-3137 (2-N-butyl-4-chloro-1-[(2'-(1H-tetrazol-5-yl)biphenyl-4-yl)-methyl]imidazole-5-carboxylic acid, U.S. Pat. No. 5,138, 069, U.S. Pat. No. 5,153,197 and U.S. Pat. No. 5,128,355), 3-(2'-(tetrazol-5-yl)-1,r-biphen-4-yl)methyl-5,7-dimethyl-2-ethyl-3H-imidazo[4,5-b]pyridine, 4'[2-ethyl-4-methyl-6-(5,6,7,8-tetrahydroimidazo[1,2-a]pyridin-2-yl]-benzimidazol-1-yl]-methyl]-l,r-biphenyl]-2-carboxylic acid, 2-butyl-6-(1-methoxy-1-methylethyl)-2-[2'-)1H-tetrazol-5-yl)biphenyl-4-ylmethyl]quinazolin-4(3H)-one, 3-[2'-carboxybiphenyl-4-yl)methyl]-2-cyclopropyl-7-methyl-3H-imidazo[4,5-b]pyridine, 2-butyl-4-chloro-1-[(2'-tetrazol-5-yl)biphenyl-4-yl)methyl]imidazole-carboxylic acid, 2-butyl-4-chloro-1-[[2'-(1H-tetrazol-5-yl) [1,1'-biphenyl]-4-yl]methyl]-1H-imidazole-5-carboxylic acid-1-(ethoxycarbonyl-oxy)ethyl ester potassium salt, dipotassium 2-butyl-4-(methylthio)-1-[[2-[[[(propylamino)carbonyl]amino]-sulfonyl](1,1'-biphenyl)-4-yl]methyl]-1H-imidazole-5-carboxylate, methyl-2-[[4-butyl-2-methyl-6-oxo-5-[[2'-(1H-tetrazol-5-yl)-[1,1'-biphenyl]-4-yl]methyl]-1-(6H)-pyrimidinyl]methyl]-3-thiophencarboxylate, 5-[(3,5-dibutyl-1H-1,2,4-triazol-1-yl)methyl]-2-[2-(1H-tetrazol-5-ylphenyl)]pyridine, 6-butyl-2-(2-phenylethyl)-5 [[2'-(1H-tetrazol-5-yl)[1,1'-biphenyl]-4-methyl]pyrimidin-4-(3H)-one D,L lysine salt, 5-methyl-7-n-propyl-8-[[2'-(1H-tetrazol-5-yl)biphenyl-4-yl]methyl]-[1,2,4]-triazolo[1,5-c]pyrimidin-2(3H)-one, 2,7-diethyl-5-[[2'-(5-tetrazoly)biphenyl-4-yl]methyl]-5H-pyrazolo[1,5-b][1,2,4]triazole potassium salt, 2-[2-butyl-4,5-dihydro-4-oxo-3-[2'-(1H-tetrazol-5-yl)-4-biphenylmethyl]-3H-imidazol[4,5-c]pyridine-5-ylmethyl]benzoic acid, ethyl ester, potassium salt, 3-methoxy-2,6-dimethyl-4-[[2'(1H-tetrazol-5-yl)-1,1'-biphenyl-4-yl]methoxy]pyridine, 2-ethoxy-1-[[2'-(5-oxo-2,5-dihydro-1,2,4-oxadiazol-3-yl)biphenyl-4-yl]methyl]-1H-benzimidazole-7-carboxylic acid, 1-[N-(2'-(1H-tetrazol-5-yl)biphenyl-4-yl-methyl)-N-valerolylaminomethyl)cyclopentane-1-carboxylic acid, 7-methyl-2n-propyl-3-[[2'1H-tetrazol-5-yl)biphenyl-4-yl]methyl]-3H-imidazo[4,5-6]pyridine, 2-[5-[(2-ethyl-5,7-dimethyl-3H-imidazo[4,5-b]pyridine-3-yl)methyl]-2-quinolinyl]sodium benzoate, 2-butyl-6-chloro-4-hydroxymethyl-5-methyl-3-[[2'-(1H-tetrazol-5-yl)biphenyl-4-yl]methyl]pyridine, 2-[[[2-butyl-1-[(4-carboxyphenyl)methyl]-1H-imidazol-5-yl]methyl]amino]benzoic acid tetrazol-5-yl)biphenyl-4-yl]methyl] pyrimidin-6-one, 4(S)-[4-(carboxymethyl)phenoxy]-N-[2(R)-[4-(2-sulfobenzamido)imidazol-1-yl]octanoyl]-L-proline, 1-(2,6-dimethylphenyl)-4-butyl-1,3-dihydro-3-[[6-[2-(1H-tetrazol-5-yl)phenyl]-3-pyridinyl]methyl]-2H-imidazol-2-one, 5,8-ethano-5,8-dimethyl-6-n-propyl-5,6,7,8-tetrahydro-1-[[2'(1H-tetrazol-5-yl)biphenyl-4-yl]methyl]-1H,4H-1,3,4a,8a-tetrazacyclopentanaphthalene-9-one, 4-[1-[2'-(1,2,3,4-tetrazol-5-yl)biphen-4-yl)methylamino]-5,6,7,8-tetrahydro-2-trifylquinazoline, 2-(2-chlorobenzoyl)imino-5-ethyl-3-[2'-(1H-tetrazole-5-yl)biphenyl-4-yl)methyl-1,3,4-thiadiazoline, 2-[5-ethyl-3-[2-(1H-tetrazole-5-yl)biphenyl-4-yl]methyl-1,3,4-thiazoline-2-ylidene]aminocarbonyl-1-cyclopentencarboxylic acid dipotassium salt, and 2-butyl-4-[N-methyl-N-(3-methylcrotonoyl)amino]-1-[[2'-(1H-tetrazol-5-yl)biphenyl-4-yl]methyl]-1H-imidzole-5-carboxylic acid 1-ethoxycarbonyloxyethyl ester, those disclosed in patent publications EP475206, EP497150, EP539086, EP539713, EP535463, EP535465, EP542059, EP497121, EP535420, EP407342, EP415886, EP424317, EP435827, EP433983, EP475898, EP490820, EP528762, EP324377, EP323841, EP420237, EP500297, EP426021, EP480204, EP429257, EP430709, EP434249, EP446062, EP505954, EP524217, EP514197, EP514198, EP514193, EP514192, EP450566, EP468372, EP485929, EP503162, EP533058, EP467207 EP399731, EP399732, EP412848, EP453210, EP456442, EP470794, EP470795, EP495626, EP495627, EP499414, EP499416, EP499415, EP511791, EP516392, EP520723, EP520724, EP539066, EP438869, EP505893, EP530702, EP400835, EP400974, EP401030, EP407102, EP411766, EP409332, EP412594, EP419048, EP480659, EP481614, EP490587, EP467715, EP479479, EP502725, EP503838, EP505098, EP505111 EP513,979 EP507594, EP510812, EP511767, EP512675, EP512676, EP512870, EP517357, EP537937, EP534706, EP527534, EP540356, EP461040, EP540039, EP465368, EP498723, EP498722, EP498721, EP515265, EP503785, EP501892, EP519831, EP532410, EP498361, EP432737, EP504888, EP508393, EP508445, EP403159, EP403158, EP425211, EP427463, EP437103, EP481448, EP488532, EP501269, EP500409, EP540400, EP005528, EP028834, EP028833, EP411507, EP425921, EP430300, EP434038, EP442473, EP443568, EP445811, EP459136, EP483683, EP518033, EP520423, EP531876, EP531874, EP392317, EP468470, EP470543, EP502314, EP529253, EP543263, EP540209, EP449699, EP465323, EP521768, EP415594, WO92/14468, WO93/08171, WO93/08169, WO91/00277, WO91/00281, WO91/14367, WO92/00067, WO92/00977, WO92/20342, WO93/04045, WO93/04046, WO91/15206, WO92/14714, WO92/09600, WO92/16552, WO93/05025, WO93/03018, WO91/07404, WO92/02508, WO92/13853, WO91/19697, WO91/11909, WO91/12001, WO91/11999, WO91/15209, WO91/15479, WO92/20687, WO92/20662, WO92/20661, WO93/01177, WO91/14679, WO91/13063, WO92/13564, WO91/17148, WO91/18888, WO91/19715, WO92/02257, WO92/04335, WO92/05161, WO92/07852, WO92/15577, WO93/03033, WO91/16313, WO92/00068, WO92/02510, WO92/09278, WO9210179, WO92/10180, WO92/10186, WO92/10181, WO92/10097, WO92/10183, WO92/10182, WO92/10187, WO92/10184, WO92/10188, WO92/10180, WO92/10185, WO92/20651, WO93/03722, WO93/06828, WO93/03040, WO92/19211, WO92/22533, WO92/06081, WO92/05784, WO93/00341, WO92/04343, WO92/04059, U.S. Pat. No. 5,104,877, U.S. Pat. No. 5,187,168, U.S. Pat. No. 5,149,699, U.S. Pat. No. 5,185,340, U.S. Pat. No. 4,880,804, U.S. Pat. No. 5,138,069, U.S. Pat. No. 4,916,129, U.S. Pat. No. 5,153,197, U.S. Pat. No. 5,173,494, U.S. Pat. No. 5,137,906, U.S. Pat. No. 5,155,126, U.S. Pat. No. 5,140,037, U.S. Pat. No. 5,137,902, U.S. Pat. No. 5,157,026, U.S. Pat. No. 5,053,329, U.S. Pat. No. 5,132,216, U.S. Pat. No. 5,057,522, U.S. Pat. No. 5,066,586, U.S. Pat. No. 5,089,626, U.S. Pat. No. 5,049,565, U.S. Pat. No. 5,087,702, U.S. Pat. No. 5,124,335, U.S. Pat. No. 5,102,880, U.S. Pat. No. 5,128,327, U.S. Pat. No. 5,151,435, U.S. Pat. No. 5,202,322, U.S. Pat. No. 5,187,159, U.S. Pat. No. 5,198,438, U.S. Pat. No. 5,182,288, U.S. Pat. No. 5,036,048, U.S. Pat. No. 5,140,036, U.S. Pat. No. 5,087,634, U.S. Pat. No. 5,196,537, U.S. Pat. No. 5,153,347, U.S. Pat. No. 5,191,086, U.S. Pat. No. 5,190,942, U.S. Pat. No. 5,177,097, U.S. Pat. No. 5,212,177, U.S. Pat. No. 5,208,234, U.S. Pat. No. 5,208,235, U.S. Pat. No. 5,212,195, U.S. Pat. No. 5,130,439, U.S. Pat. No. 5,045,540, U.S. Pat. No. 5,041,152, and U.S. Pat. No. 5,210,204, and pharmaceutically acceptable salts and esters thereof; α/β adrenergic blockers such as nipradilol, arotinolol, amosulalol, bretylium tosylate (CAS RN: 61-75-6), dihydroergtamine mesylate (such as ergotaman-3',6',18-trione,9,-10-dihydro-12'-hydroxy-2'-methyl-5'-(phenylmethyl)-,(5'(a))-, monomethanesulfonate, e.g., DHE 45® Injection, Novartis), carvedilol (such as (±)-1-(Carbazol-4-yloxy)-3-[[2-(o-methoxyphenoxy)ethyl]amino]-2-propanol, e.g., Coreg®, SmithKline Beecham), labetalol (such as 5-[1-hydroxy-2-[(1-methyl-3-phenylpropyl)amino]ethyl]salicylamide monohydrochloride, e.g., Normodyne®, Schering), bretylium tosylate (Benzenemethanaminium, 2-bromo-N-ethyl-N,N-dimethyl-, salt with 4-methylbenzenesulfonic acid (1:1)

CAS RN 61-75-6), phentolamine mesylate (Phenol, 3-[[(4,5-dihydro-1H-imidazol-2-yl)methyl](4-methylphenyl)amino]-, monomethanesulfonate (salt) CAS RN 65-28-1), solypertine tartrate (5H-1,3-Dioxolo[4,5-f]indole, 7-[2-[4-(2-methoxyphenyl)-1-piperazinyl]ethyl]-, (2R,3R)-2,3-dihydroxybutanedioate (1:1) CAS RN 5591-43-5), zolertine hydrochloride (piperazine, 1-phenyl4-[2-(1H-tetrazol-5-yl)ethyl]-, monohydrochloride (8C1, 9C1) CAS RN 7241-94-3) and the like; α adrenergic receptor blockers, such as alfuzosin (CAS RN: 81403-68-1), terazosin, urapidil, prazosin (Minipress®), tamsulosin, bunazosin, trimazosin, doxazosin, naftopidil, indoramin, WHP 164, XENO1O, fenspiride hydrochloride (which may be prepared as disclosed in U.S. Pat. No. 3,399,192), proroxan (CAS RN 33743-96-3), and labetalol hydrochloride and combinations thereof; a 2 agonists such as methyldopa, methyldopa HCL, lofexidine, tiamenidine, moxonidine, rilmenidine, guanobenz, and the like; aldosterone inhibitors, and the like; renin inhibitors including Aliskiren (SPP100; Novartis/Speedel); angiopoietin-2-binding agents such as those disclosed in WO03/030833; anti-angina agents such as ranolazine (hydrochloride 1-piperazineacetamide, N-(2,6-dimethylphenyl)-4-[2-hydroxy-3-(2-methoxyphenoxy)propyl]-, dihydrochloride CAS RN 95635-56-6), betaxolol hydrochloride (2-Propanol, 1-[4-[2(cyclopropylmethoxy)ethyl]phenoxy]-3-[(1-methylethyl)amino]-, hydrochloride CAS RN 63659-19-8), butoprozine hydrochloride (Methanone, [4-[3(dibutylamino)propoxy]phenyl](2-ethyl-3-indolizinyl)-, monohydrochloride CAS RN 62134-34-3), cinepazet maleatel-piperazineacetic acid, 4-[1-oxo-3-(3,4,5-trimethoxyphenyl)-2-propenyl]-, ethyl ester, (2Z)-2-butenedioate (1:1) CAS RN 50679-07-7), tosifen (Benzenesulfonamide, 4-methyl-N-[[[(1S)-1-methyl-2-phenylethyl]amino]carbonyl]-CAS RN 32295-184), verapamilhydrochloride (Benzeneacetonitrile, α-[3-[[2-(3,4-dimethoxyphenyl)ethyl]methylamino]propyl]-3,4-dimethoxy-α-(1-methylethyl)-, monohydrochloride CAS RN 152-114), molsidomine (1,2,3-Oxadiazolium, 5-[(ethoxycarbonyl)amino]-3-(4-morpholinyl)-, inner salt CAS RN 25717-80-0), and ranolazine hydrochloride (1-piperazineacetamide, N-(2,6-dimethylphenyl)-4-[2-hydroxy-3-(2-meth-oxyphenoxy)propyl]-, dihydrochloride CAS RN 95635-56-6); tosifen (Benzenesulfonamide, 4-methyl-N-[[[(1S)-1-methyl-2-phenylethyl]amino]carbonyl]-CAS RN 32295-184); adrenergic stimulants such as guanfacine hydrochloride (such as N-amidino-2-(2,6-dichlorophenyl) acetamide hydrochloride, e.g., Tenex® Tablets available from Robins); methyldopa-hydrochlorothiazide (such as levo-3-(3,4-dihydroxyphenyl)-2-methylalanine) combined with Hydrochlorothiazide (such as 6-chloro-3,4-dihydro-2H-1,2,4-benzothiadiazine-7-sulfonamide 1,1-dioxide, e.g., the combination as, e.g., Aldoril® Tablets available from Merck), methyldopa-chlorothiazide (such as 6-chloro-2H-1,2,4-benzothiadiazine-7-sulfonamide 1,1-dioxide and methyldopa as described above, e.g., Aldoclor®, Merck), clonidine hydrochloride (such as 2-(2,6-dichlorophenylamino)-2-imidazoline hydrochloride and chlorthalidone (such as 2-chloro-5-(1-hydroxy-3-oxo-1-isoindolinyl)benzenesulfonamide), e.g., Combipres®, Boehringer Ingelheim), clonidine hydrochloride (such as 2-(2,6-dichlorophenylamino)-2-imidazoline hydrochloride, e.g., Catapres®, Boehringer Ingelheim), clonidine (1H-Imidazol-2-amine, N-(2,6-dichlorophenyl)4,5-dihydro-CAS RN 4205-90-7), Hyzaar (Merck; a combination of losartan and hydrochlorothiazide), Co-Diovan (Novartis; a combination of valsartan and hydrochlorothiazide), Lotrel (Novartis; a combination of benazepril and amlodipine) and Caduet (Pfizer; a combination of amlodipine and atorvastatin), and those agents disclosed in US20030069221.

Agents for the Treatment of Respiratory Disorders

The GCRA peptides described herein can be used in combination therapy with one or more of the following agents useful in the treatment of respiratory and other disorders including but not limited to: (1) β-agonists including but not limited to: albuterol (PRO VENTIL®, S ALBUT AMOK), VENTOLIN®), bambuterol, bitoterol, clenbuterol, fenoterol, formoterol, isoetharine (BRONKOSOL®, BRONKOMETER®), metaproterenol (ALUPENT®, METAPREL®), pirbuterol (MAXAIR®), reproterol, rimiterol, salmeterol, terbutaline (BRETHAIRE®, BRETHINE®, BRICANYL®), adrenalin, isoproterenol (ISUPREL®), epinephrine bitartrate (PRIMATENE®), ephedrine, orciprenline, fenoterol and isoetharine; (2) steroids, including but not limited to beclomethasone, beclomethasone dipropionate, betamethasone, budesonide, bunedoside, butixocort, dexamethasone, flunisolide, fluocortin, fluticasone, hydrocortisone, methyl prednisone, mometasone, predonisolone, predonisone, tipredane, tixocortal, triamcinolone, and triamcinolone acetonide; (3) β2-agonist-corticosteroid combinations [e.g., salmeterol-fluticasone (AD V AIR®), formoterol-budesonid (S YMBICORT®)]; (4) leukotriene D4 receptor antagonists/leukotriene antagonists/LTD4 antagonists (i.e., any compound that is capable of blocking, inhibiting, reducing or otherwise interrupting the interaction between leukotrienes and the Cys LTI receptor) including but not limited to: zafhiukast, montelukast, montelukast sodium (SINGULAIR®), pranlukast, iralukast, pobilukast, SKB-106,203 and compounds described as having LTD4 antagonizing activity described in U.S. Pat. No. 5,565,473; (5) 5-lipoxygenase inhibitors and/or leukotriene biosynthesis inhibitors [e.g., zileuton and BAY1005 (CA registry 128253-31-6)]; (6) histamine H1 receptor antagonists/antihistamines (i.e., any compound that is capable of blocking, inhibiting, reducing or otherwise interrupting the interaction between histamine and its receptor) including but not limited to: astemizole, acrivastine, antazoline, azatadine, azelastine, astamizole, bromopheniramine, bromopheniramine maleate, carbinoxamine, carebastine, cetirizine, chlorpheniramine, chlorpheniramine maleate, cimetidine clemastine, cyclizine, cyproheptadine, descarboethoxyloratadine, dexchlorpheniramine, dimethindene, diphenhydramine, diphenylpyraline, doxylamine succinate, doxylamine, ebastine, efletirizine, epinastine, famotidine, fexofenadine, hydroxyzine, hydroxyzine, ketotifen, levocabastine, levocetirizine, levocetirizine, loratadine, meclizine, mepyramine, mequitazine, methdilazine, mianserin, mizolastine, noberastine, norasternizole, noraztemizole, phenindamine, pheniramine, picumast, promethazine, pynlamine, pyrilamine, ranitidine, temelastine, terfenadine, trimeprazine, tripelenamine, and triprolidine; (7) an anticholinergic including but not limited to: atropine, benztropine, biperiden, flutropium, hyoscyamine (e.g. Levsin®; Levbid®; Levsin/SL®, Anaspaz®, Levsinex Timecaps®, NuLev®), ilutropium, ipratropium, ipratropium bromide, methscopolamine, oxybutinin, rispenzepine, scopolamine, and tiotropium; (8) an anti-tussive including but not limited to: dextromethorphan, codeine, and hydromorphone; (9) a decongestant including but not limited to: pseudoephedrine and phenylpropanolamine; (10) an expectorant including but not limited to: guafenesin, guaicolsulfate, terpin, ammonium chloride, glycerol guaicolate, and iodinated glycerol; (11) a bronchodilator including but not limited to: theophylline and aminophylline; (12) an anti-inflammatory including but not limited to: fluribiprofen, diclophenac, indomethacin, ketoprofen, S-ketroprophen, tenoxicam; (13) a PDE (phosphodiesterase) inhibitor including but not limited to those disclosed herein; (14) a recombinant humanized monoclonal antibody

[e.g. xolair (also called omalizumab), rhuMab, and talizumab]; (15) a humanized lung surfactant including recombinant forms of surfactant proteins SP-B, SP-C or SP-D [e.g. SURFAXIN®, formerly known as dsc-104 (Discovery Laboratories)], (16) agents that inhibit epithelial sodium channels (ENaC) such as amiloride and related compounds; (17) antimicrobial agents used to treat pulmonary infections such as acyclovir, amikacin, amoxicillin, doxycycline, trimethoprin sulfamethoxazole, amphotericin B, azithromycin, clarithromycin, roxithromycin, clarithromycin, cephalosporins(cefoxitin, cefinetazole etc), ciprofloxacin, ethambutol, gentimycin, ganciclovir, imipenem, isoniazid, itraconazole, penicillin, ribavirin, rifampin, rifabutin, amantadine, rimantidine, streptomycin, tobramycin, and vancomycin; (18) agents that activate chloride secretion through Ca++ dependent chloride channels (such as purinergic receptor (P2Y(2) agonists); (19) agents that decrease sputum viscosity, such as human recombinant DNase 1, (Pulmozyme®); (20) nonsteroidal anti-inflammatory agents (acemetacin, acetaminophen, acetyl salicylic acid, alclofenac, alminoprofen, apazone, aspirin, benoxaprofen, bezpiperylon, bucloxic acid, carprofen, clidanac, diclofenac, diclofenac, diflunisal, diflusinal, etodolac, fenbufen, fenbufen, fenclofenac, fenclozic acid, fenoprofen, fentiazac, feprazone, flufenamic acid, flufenisal, flufenisal, fluprofen, flurbiprofen, flurbiprofen, furofenac, ibufenac, ibuprofen, indomethacin, indomethacin, indoprofen, isoxepac, isoxicam, ketoprofen, ketoprofen, ketorolac, meclofenamic acid, meclofenamic acid, mefenamic acid, mefenamic acid, miroprofen, mofebutazone, nabumetone oxaprozin, naproxen, naproxen, niflumic acid, oxaprozin, oxpinac, oxyphenbutazone, phenacetin, phenylbutazone, phenylbutazone, piroxicam, piroxicam, pirprofen, pranoprofen, sudoxicam, tenoxican, sulfasalazine, sulindac, sulindac, suprofen, tiaprofenic acid, tiopinac, tioxaprofen, tolfenamic acid, tolmetin, tolmetin, zidometacin, zomepirac, and zomepirac); and (21) aerosolized antioxidant therapeutics such as S-Nitrosoglutathione.

Anti-Obesity Agents

The GCRA peptides described herein can be used in combination therapy with an anti-obesity agent. Suitable such agents include, but are not limited to: 1 1β HSD-I (11-beta hydroxy steroid dehydrogenase type 1) inhibitors, such as BVT 3498, BVT 2733, 3-(1-adamantyl)-4-ethyl-5-(ethylthio)-4H-1,2,4-triazole, 3-(1-adamantyl)-5-(3,4,5-trimethoxyphenyl)-4-methyl-4H-1,2,4-triazole, 3-adamantanyl-4,5,6,7,8,9,10,11,12,3a-decahydro-1,2,4-triazolo[4,3-a][1 1]annulene, and those compounds disclosed in WO01/90091, WO 01/90090, WO 01/90092 and WO02/072084; 5HT antagonists such as those in WO03/037871, WO03/037887, and the like; 5HTIa modulators such as carbidopa, benserazide and those disclosed in U.S. Pat. No. 6,207,699, WO03/031439, and the like; 5HT2c (serotonin receptor 2c) agonists, such as BVT933, DPCA37215, IK264, PNU 22394, WAY161503, R-1065, SB 243213 (Glaxo Smith Kline) and YM 348 and those disclosed in U.S. Pat. No. 3,914,250, WO00/77010, WO02/36596, WO02/48124, WO02/10169, WO01/66548, WO02/44152, WO02/51844, WO02/40456, and WO02/40457; 5HT6 receptor modulators, such as those in WO03/030901, WO03/035061, WO03/039547, and the like; acyl-estrogens, such as oleoyl-estrone, disclosed in del Mar-Grasa, M. et al, Obesity Research, 9:202-9 (2001) and Japanese Patent Application No. JP 2000256190; anorectic bicyclic compounds such as 1426 (Aventis) and 1954 (Aventis), and the compounds disclosed in WO00/18749, WO01/32638, WO01/62746, WO01/62747, and WO03/015769; CB 1 (cannabinoid-1 receptor) antagonist/inverse agonists such as rimonabant (Acomplia; Sanofi), SR-147778 (Sanofi), SR-141716 (Sanofi), BAY 65-2520 (Bayer), and SLV 319 (Solvay), and those disclosed in patent publications U.S. Pat. No. 4,973,587, U.S. Pat. No. 5,013,837, U.S. Pat. No. 5,081, 122, U.S. Pat. No. 5,112,820, U.S. Pat. No. 5,292,736, U.S. Pat. No. 5,532,237, U.S. Pat. No. 5,624,941, U.S. Pat. No. 6,028,084, U.S. Pat. No. 6,509,367, U.S. Pat. No. 6,509,367, WO96/33159, WO97/29079, WO98/31227, WO98/33765, WO98/37061, WO98/41519, WO98/43635, WO98/43636, WO99/02499, WO00/10967, WO00/10968, WO01/09120, WO01/58869, WO01/64632, WO01/64633, WO01/64634, WO01/70700, WO01/96330, WO02/076949, WO03/006007, WO03/007887, WO03/020217, WO03/026647, WO03/026648, WO03/027069, WO03/027076, WO03/027114, WO03/037332, WO03/040107, WO03/086940, WO03/084943 and EP658546; CCK-A (cholecystokinin-A) agonists, such as AR-R 15849, GI 181771 (GSK), JMV-180, A-71378, A-71623 and SR146131 (Sanofi), and those described in U.S. Pat. No. 5,739,106; CNTF (Ciliary neurotrophic factors), such as GI-181771 (Glaxo-SmithKline), SR146131 (Sanofi Synthelabo), butabindide, PD 170,292, and PD 149164 (Pfizer); CNTF derivatives, such as Axokine® (Regeneron), and those disclosed in WO94/09134, WO98/22128, and WO99/43813; dipeptidyl peptidase IV (DP-IV) inhibitors, such as isoleucine thiazolidide, valine pyrrolidide, NVP-DPP728, LAF237, P93/01, P 3298, TSL 225 (tryptophyl-1,2,3,4-tetrahydroisoquinoline-3-carboxylic acid; disclosed by Yamada et al, Bioorg. & Med. Chem. Lett. 8 (1998) 1537-1540), TMC-2A/2B/2C, CD26 inhibtors, FE 999011, P9310/K364, VIP 0177, SDZ 274-444, 2-cyanopyrrolidides and 4-cyanopyrrolidides as disclosed by Ashworth et al, Bioorg. & Med. Chem. Lett., Vol. 6, No. 22, pp 1163-1166 and 2745-2748 (1996) and the compounds disclosed patent publications. WO99/38501, WO99/46272, WO99/67279 (Probiodrug), WO99/67278 (Probiodrug), WO99/61431 (Probiodrug), WO02/083128, WO02/062764, WO03/000180, WO03/000181, WO03/000250, WO03/002530, WO03/002531, WO03/002553, WO03/002593, WO03/004498, WO03/004496, WO03/017936, WO03/024942, WO03/024965, WO03/033524, WO03/037327 and EP1258476; growth hormone secretagogue receptor agonists/antagonists, such as NN703, hexarelin, MK-0677 (Merck), SM-130686, CP-424391 (Pfizer), LY 444,711 (Eli Lilly), L-692,429 and L-163,255, and such as those disclosed in U.S. Ser. No. 09/662,448, U.S. provisional application 60/203,335, U.S. Pat. No. 6,358,951, US2002049196, US2002/022637, WO01/56592 and WO02/32888; H3 (histamine H3) antagonist/inverse agonists, such as thioperamide, 3-(1H-imidazol-4-yl)propyl N-(4-pentenyl)carbamate), clobenpropit, iodophenpropit, imoproxifan, GT2394 (Gliatech), and A331440, O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)) and histamine H3 receptor modulators such as those disclosed in WO02/15905, WO03/024928 and WO03/024929; leptin derivatives, such as those disclosed in U.S. Pat. No. 5,552, 524, U.S. Pat. No. 5,552,523, U.S. Pat. No. 5,552,522, U.S. Pat. No. 5,521,283, WO96/23513, WO96/23514, WO96/23515, WO96/23516, WO96/23517, WO96/23518, WO96/23519, and WO96/23520; leptin, including recombinant human leptin (PEG-OB, Hoffman La Roche) and recombinant methionyl human leptin (Amgen); lipase inhibitors, such as tetrahydrolipstatin (orlistat/Xenical®), Triton WR1 339, RHC80267, lipstatin, teasaponin, diethylumbelliferyl phosphate, FL-386, WAY-121898, Bay-N-3176, valilactone, esteracin, ebelactone A, ebelactone B, and RHC 80267, and those disclosed in patent publications WO01/77094, U.S. Pat. No. 4,598,089, U.S. Pat. No. 4,452,813, U.S. Pat. No. 5,512,565, U.S. Pat. No. 5,391,571, U.S. Pat. No. 5,602,151, U.S. Pat. No. 4,405,644, U.S. Pat. No. 4,189,438, and U.S. Pat. No. 4,242,453; lipid metabolism modulators such as maslinic acid, erythrodiol, ursolic acid uvaol, betulinic acid, betulin, and the like and compounds disclosed in WO03/011267; Mc4r (melanocortin 4 receptor) agonists, such as CHIR86036 (Chiron), ME-10142, ME-10145, and HS-131 (Melacure), and those disclosed in PCT publication Nos. WO99/64002, WO00/74679, WO 01/991752, WO 01/25192, WO 01/52880, WO 01/74844, WO 01/70708, WO01/70337, WO01/91752, WO02/059095, WO02/059107, WO02/059108, WO02/059117, WO02/06276, WO02/12166, WO02/11715, WO02/12178, WO02/15909, WO02/38544, WO02/068387, WO02/068388, WO02/067869, WO02/081430, WO03/06604, WO03/007949, WO03/009847, WO03/009850, WO03/013509, and WO03/031410; Mc5r (melanocortin 5 receptor) modulators, such as those disclosed in WO97/19952, WO00/15826, WO00/15790, US20030092041; melanin-concentrating hormone 1 receptor (MCHR) antagonists, such as T-226296 (Takeda), SB 568849, SNP-7941 (Synaptic), and those disclosed in patent publications WO 01/21169, WO01/82925, WO01/87834, WO02/051809, WO02/06245, WO02/076929, WO02/076947, WO02/04433, WO02/51809, WO02/083134, WO02/094799, WO03/004027, WO03/13574, WO03/15769, WO03/028641, WO03/035624, WO03/033476, WO03/033480, JP13226269, and JP1437059; mGluR5 modulators such as those disclosed in WO03/029210, WO03/047581, WO03/048137, WO03/051315, WO03/051833, WO03/053922, WO03/059904, and the like; serotoninergic agents, such as fenfluramine (such as Pondimin® (Benzeneethanamine, N-ethyl-alpha-methyl-3-(trifluoromethyl)-, hydrochloride), Robbins), dexfenfluramine (such as Redux® (Benzeneethanamine, N-ethyl-alpha-methyl-3-(trifluoromethyl)-, hydrochloride), Interneuron) and sibutramine ((Meridia®, Knoll/Reductil™) including racemic mixtures, as optically pure isomers (+) and (−), and pharmaceutically acceptable salts, solvents, hydrates, clathrates and prodrugs thereof including sibutramine hydrochloride monohydrate salts thereof, and those compounds disclosed in U.S. Pat. No. 4,746,680, U.S. Pat. No. 4,806,570, and U.S. Pat. No. 5,436,272, US20020006964, WO 01/27068, and WO 01/62341; NE (norepinephrine) transport inhibitors, such as GW 320659, despiramine, talsupram, and nomifensine; NPY 1 antagonists, such as BIBP3226, J-115814, BIBO 3304, LY-357897, CP-671906, GI-264879A, and those disclosed in U.S. Pat. No. 6,001,836, WO96/14307, WO01/23387, WO99/51600, WO01/85690, WO01/85098, WO01/85173, and WO01/89528; NPYS (neuropeptide Y Y5) antagonists, such as 152,804, GW-569180A, GW-594884A, GW-587081x, GW-548118x, FR235208, FR226928, FR240662, FR252384, 1229U91, GI-264879A, CGP71683A, LY-377897, LY-366377, PD-160170, SR-120562A, SR-120819A, JCF-104, and H409/22 and those compounds disclosed in patent publications U.S. Pat. No. 6,140,354, U.S. Pat. No. 6,191,160, U.S. Pat. No. 6,218,408, U.S. Pat. No. 6,258,837, U.S. Pat. No. 6,313,298, U.S. Pat. No. 6,326,375, U.S. Pat. No. 6,329,395, U.S. Pat. No. 6,335,345, U.S. Pat. No. 6,337,332, U.S. Pat. No. 6,329,395, U.S. Pat. No. 6,340,683, EP01010691, EP-01044970, WO97/19682, WO97/20820, WO97/20821, WO97/20822, WO97/20823, WO98/27063, WO00/107409, WO00/185714, WO00/185730, WO00/64880, WO00/68197, WO00/69849, WO/0113917, WO01/09120, WO01/14376, WO01/85714, WO01/85730, WO01/07409, WO01/02379, WO01/23388, WO01/23389, WO 01/44201, WO01/62737, WO01/62738, WO01/09120, WO02/20488, WO02/22592, WO02/48152, WO02/49648, WO02/051806, WO02/094789, WO03/009845, WO03/014083, WO03/022849, WO03/028726 and Norman et al, J. Med. Chem. 43:4288-4312 (2000); opioid antagonists, such as nalmefene (REVEX®), 3-methoxynaltrexone, methylnaltrexone, naloxone, and naltrexone (e.g. PT901; Pain Therapeutics, Inc.) and those disclosed in US20050004155 and WO00/21509; orexin antagonists, such as SB-334867-A and those disclosed in patent publications WO01/96302, WO01/68609, WO02/44172, WO02/51232, WO02/51838, WO02/089800, WO02/090355, WO03/023561, WO03/032991, and WO03/037847; PDE inhibitors (e.g. compounds which slow the degradation of cyclic AMP (cAMP) and/or cyclic GMP (cGMP) by inhibition of the phosphodiesterases, which can lead to a relative increase in the intracellular concentration of cAMP and cGMP; possible PDE inhibitors are primarily those substances which are to be numbered among the class consisting of the PDE3 inhibitors, the class consisting of the PDE4 inhibitors and/or the class consisting of the PDE5 inhibitors, in particular those substances which can be designated as mixed types of PDE3/4 inhibitors or as mixed types of PDE3/4/5 inhibitors) such as those disclosed in patent publications DE1470341, DE2108438, DE2123328, DE2305339, DE2305575, DE2315801, DE2402908, DE2413935, DE2451417, DE2459090, DE2646469, DE2727481, DE2825048, DE2837161, DE2845220, DE2847621, DE2934747, DE3021792, DE3038166, DE3044568, EP000718, EP0008408, EP0010759, EP0059948, EP0075436, EP0096517, EP0112987, EP0116948, EP0150937, EP0158380, EP0161632, EP0161918, EP0167121, EP0199127, EP0220044, EP0247725, EP0258191, EP0272910, EP0272914, EP0294647, EP0300726, EP0335386, EP0357788, EP0389282, EP0406958, EP0426180, EP0428302, EP0435811, EP0470805, EP0482208, EP0490823, EP0506194, EP0511865, EP0527117, EP0626939, EP0664289, EP0671389, EP0685474, EP0685475, EP0685479, JP92234389, JP94329652, JP95010875, U.S. Pat. No. 4,963,561, U.S. Pat. No. 5,141,931, WO9117991, WO9200968, WO9212961, WO9307146, WO9315044, WO9315045, WO9318024, WO9319068, WO9319720, WO9319747, WO9319749, WO9319751, WO9325517, WO9402465, WO9406423, WO9412461, WO9420455, WO9422852, WO9425437, WO9427947, WO9500516, WO9501980, WO9503794, WO9504045, WO9504046, WO9505386, WO9508534, WO9509623, WO9509624, WO9509627, WO9509836, WO9514667, WO9514680, WO9514681, WO9517392, WO9517399, WO9519362, WO9522520, WO9524381, WO9527692, WO9528926, WO9535281, WO9535282, WO9600218, WO9601825, WO9602541, WO9611917, DE3142982, DE1 116676, DE2162096, EP0293063, EP0463756, EP0482208, EP0579496, EP0667345 U.S. Pat. No. 6,331,543, US20050004222 (including those disclosed in formulas I-XIII and paragraphs 37-39, 85-0545 and 557-577), WO9307124, EP0163965, EP0393500, EP0510562, EP0553174, WO9501338 and WO9603399, as well as PDE5 inhibitors (such as RX-RA-69, SCH-51866, KT-734, vesnarinone, zaprinast, SKF-96231, ER-21355, BF/GP-385, NM-702 and sildenafil (Viagra™)), PDE4 inhibitors (such as etazolate, ICI63197, RP73401, imazolidinone (RO-20-1724), MEM 1414 (R1533/R1500; Pharmacia Roche), denbufylline, rolipram, oxagrelate, nitraquazone, Y-590, DH-6471, SKF-94120, motapizone, lixazinone, indolidan, olprinone, atizoram, KS-506-G, dipamfylline, BMY-43351, atizoram, arofylline, filaminast, PDB-093, UCB-29646, CDP-840, SKF-107806, piclamilast, RS-17597, RS-25344-000, SB-207499, TIBENELAST, SB-210667, SB-211572, SB-211600, SB-212066, SB-212179, GW-3600, CDP-840, mopidamol, anagrelide, ibudilast, aminone, pimobendan, cilostazol, quazinone and N-(3,5-dichloropyrid-4-yl)-3-cyclopropylmethoxy-4-difluoromethoxybenzamide, PDE3 inhibitors (such as ICI153, 100, bemorandane (RWJ 22867), MCI-154, UD-CG 212, sulmazole, ampizone, cilostamide, carbazeran, piroximone, imazodan, CI-930, siguazodan, adibendan, saterinone, SKF-95654, SDZ-MKS-492, 349-U-85, emoradan, EMD-53998, EMD-57033, NSP-306, NSP-307, revizinone, NM-702, WIN-62582 and WIN-63291, enoximone and milrinone, PDE3/4 inhibitors (such as benafentrine, trequinsin, ORG-30029, zardaverine, L-686398, SDZ-ISQ-844, ORG-20241, EMD-54622, and tolafentrine) and other PDE inhibitors (such as vinpocetin, papaverine, enprofylline, cilomilast, fenoximone, pentoxifylline, roflumilast, tadalafil(Clalis®), theophylline, and vardenafil(Levitra®); Neuropeptide Y2 (NPY2) agonists include but are not limited to: polypeptide YY and fragments and variants thereof (e.g. YY3-36 (PYY3-36)(N. Engl. J. Med. 349:941, 2003; IKPEAPGE DASPEELNRY YASLRHYLNL VTRQRY (SEQ ID NO:107)) and PYY agonists such as those disclosed in WO02/47712, WO03/026591, WO03/057235, and WO03/027637; serotonin reuptake inhibitors, such as, paroxetine, fluoxetine (Prozac™), fluvoxamine, sertraline, citalopram, and imipramine, and those disclosed in U.S. Pat. No. 6,162,805, U.S. Pat. No. 6,365,633, WO03/00663, WO 01/27060, and WO 01/162341; thyroid hormone β agonists, such as KB-2611 (KaroBioBMS), and those disclosed in WO02/15845, WO97/21993, WO99/00353, GB98/284425, U.S. Provisional Application No. 60/183,223, and Japanese Patent Application No. JP 2000256190; UCP-I (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), retinoic acid, and those disclosed in WO99/00123; P3 (beta adrenergic receptor 3) agonists, such as AJ9677/TAK677 (Dainippon/Takeda), L750355 (Merck), CP331648 (Pfizer), CL-316,243, SB 418790, BRL-37344, L-796568, BMS-196085, BRL-35135A, CGP12177A, BTA-243, GW 427353, Trecadrine, Zeneca D7114, N-5984 (Nisshin Kyorin), LY-377604 (Lilly), SR 59119A, and those disclosed in U.S. Pat. No. 5,541,204, U.S. Pat. No. 5,770,615, U.S. Pat. No. 5,491,134, U.S. Pat. No. 5,776,983, U.S. Pat. No. 4,880,64, U.S. Pat. No. 5,705,515, U.S. Pat. No. 5,451,677, WO94/18161, WO95/29159, WO97/46556, WO98/04526 and WO98/32753, WO01/74782, WO02/32897, WO03/014113, WO03/016276, WO03/016307, WO03/024948, WO03/024953 and WO03/037881; noradrenergic agents including, but not limited to, diethylpropion (such as Tenuate® (1-propanone, 2-(diethylamino)-1-phenyl-, hydrochloride), Merrell), dextroamphetamine (also known as dextroamphetamine sulfate, dexamphetamine, dexedrine, Dexampex, Ferndex, Oxydess II, Robese, Spancap #1), mazindol ((or 5-(p-chlorophenyl)-2,5-dihydro-3H-imidazo[2,1-a]isoindol-5-ol) such as Sanorex®, Novartis or Mazanor®, Wyeth Ayerst), phenylpropanolamine (or Benzenemethanol, alpha-(1-aminoethyl)-, hydrochloride), phentermine ((or Phenol, 3-[[4,5-duhydro-1H-imidazol-2-yl)ethyl](4-methypheny-1)amino], monohydrochloride) such as Adipex-P®, Lemmon, FASTIN®, Smith-Kline Beecham and Ionamin®, Medeva), phendimetrazine ((or (2S,3S)-3,4-Dimethyl-2-phenylmorpholine L-(+)-tartrate (1:1)) such as Metra® (Forest), Plegine® (Wyeth-Ay erst), Prelu-2® (Boehringer Ingelheim), and Statobex® (Lemmon), phendamine tartrate (such as Thephorin® (2,3,4,9-Tetrahydro-2-methyl-9-phenyl-1H-indenol[2,1-c]pyridine L-(+)-tartrate (1:1)), Hoffmann-LaRoche), methamphetamine (such as Desoxyn®, Abbot ((S)—N, (alpha)-dimethylbenzeneethanamine hydrochloride)), and phendimetrazine tartrate (such as Bontril® Slow-Release Capsules, Amarin (-3,4-Dimethyl-2-phenylmorpholine Tartrate); fatty acid oxidation upregulator/inducers such as Famoxin® (Genset); monamine oxidase inhibitors including but not limited to befloxatone, moclobemide, brofaromine, phenoxathine, esuprone, befol, toloxatone, pirlindol, amiflamine, sercloremine, bazinaprine, lazabemide, milacemide, caroxazone and other certain compounds as disclosed by WO01/12176; and other anti-obesity agents such as 5HT-2 agonists, ACC (acetyl-CoA carboxylase) inhibitors such as those described in WO03/072197, alpha-lipoic acid (alpha-LA), AOD9604, appetite suppressants such as those in WO03/40107, ATL-962 (Alizyme PLC), benzocaine, benzphetamine hydrochloride (Didrex), bladderwrack (focus vesiculosus), BRS3 (bombesin receptor subtype 3) agonists, bupropion, caffeine, CCK agonists, chitosan, chromium, conjugated linoleic acid, corticotropin-releasing hormone agonists, dehydroepiandrosterone, DGAT1 (diacylglycerol acyltransferase 1) inhibitors, DGAT2 (diacylglycerol acyltransferase 2) inhibitors, dicarboxylate transporter inhibitors, ephedra, exendin-4 (an inhibitor of glp-1) FAS (fatty acid synthase) inhibitors (such as Cerulenin and C75), fat resorption inhibitors (such as those in WO03/053451, and the like), fatty acid transporter inhibitors, natural water soluble fibers (such as psyllium, *plantago*, guar, oat, pectin), galanin antagonists, galega (Goat's Rue, French Lilac), *garcinia cambogia*, germander (teucrium chamaedrys), ghrelin antibodies and ghrelin antagonists (such as those disclosed in WO01/87335, and WO02/08250), polypeptide hormones and variants thereof which affect the islet cell secretion, such as the hormones of the secretin/gastric inhibitory polypeptide (GIP)/vasoactive intestinal polypeptide (VIP)/pituitary adenylate cyclase activating polypeptide (PACAP)/glucagon-like polypeptide II (GLP-II)/glicentin/glucagon gene family and/or those of the adrenomedullin/amylin/calcitonin gene related polypeptide (CGRP) gene family includingGLP-1 (glucagon-like polypeptide 1) agonists (e.g. (1) exendin-4, (2) those GLP-1 molecules described in US20050130891 including GLP-1(7-34), GLP-1(7-35), GLP-1(7-36) or GLP-1(7-37) in its C-terminally carboxylated or amidated form or as modified GLP-I polypeptides and modifications thereof including those described in paragraphs 17-44 of US20050130891, and derivatives derived from GLP-1-(7-34) COOH and the corresponding acid amide are employed which have the following general formula: R—NH-HAEGT-FTSDVSYLEGQAAKEFIAWLVK-CONH$_2$ (SEQ ID NO: 108) wherein R=H or an organic compound having from 1 to 10 carbon atoms. Preferably, R is the residue of a carboxylic acid. Particularly preferred are the following carboxylic acid residues: formyl, acetyl, propionyl, isopropionyl, methyl, ethyl, propyl, isopropyl, n-butyl, sec-butyl, tert-butyl.) and glp-1 (glucagon-like polypeptide-1), glucocorticoid antagonists, glucose transporter inhibitors, growth hormone secretagogues (such as those disclosed and specifically described in U.S. Pat. No. 5,536,716), interleukin-6 (IL-6) and modulators thereof (as in WO03/057237, and the like), L-carnitine, Mc3r (melanocortin 3 receptor) agonists, MCH2R (melanin concentrating hormone 2R) agonist/antagonists, melanin concentrating hormone antagonists, melanocortin agonists (such as Melanotan II or those described in WO 99/64002 and WO 00/74679), noname herba, phosphate transporter inhibitors, phytopharm compound 57 (CP 644,673), pyruvate, SCD-I (stearoyl-CoA desaturase-1) inhibitors, T71 (Tularik, Inc., Boulder Colo.), Topiramate (Topimax®), indicated as an anti-convulsant which has been shown to increase weight loss), transcription factor modulators (such as those disclosed in WO03/026576), β-hydroxy steroid dehydrogenase-1 inhibitors ((3-HSD-I), β-hydroxy-β-methylbutyrate, p57 (Pfizer), Zonisamide (Zonegran™, indicated as an anti-epileptic which has been shown to lead to weight loss), and the agents disclosed in US20030119428 paragraphs 20-26.

Anti-Diabetic Agents

The GCRA peptides described herein can be used in therapeutic combination with one or more anti-diabetic agents, including but not limited to: PPARγ agonists such as glitazones (e.g., WAY-120,744, AD 5075, balaglitazone, ciglitazone, darglitazone (CP-86325, Pfizer), englitazone (CP-68722, Pfizer), isaglitazone (MIT/J&J), MCC-555 (Mitsibishi disclosed in U.S. Pat. No. 5,594,016), pioglitazone (such as such as Actos™ pioglitazone; Takeda), rosiglitazone (Avandia™; Smith Kline Beecham), rosiglitazone maleate, troglitazone (Rezulin®, disclosed in U.S. Pat. No. 4,572,912), rivoglitazone (CS-Ol 1, Sankyo), GL-262570 (Glaxo Welcome), BRL49653 (disclosed in WO98/05331), CLX-0921, 5-BTZD, GW-0207, LG-100641, JJT-501 (JPNT/P&U), L-895645 (Merck), R-119702 (Sankyo/Pfizer), NN-2344 (Dr. Reddy/NN), YM-440 (Yamanouchi), LY-300512, LY-519818, R483 (Roche), T131 (Tularik), and the like and compounds disclosed in U.S. Pat. No. 4,687,777, U.S. Pat. No. 5,002,953, U.S. Pat. No. 5,741,803, U.S. Pat. No. 5,965,584, U.S. Pat. No. 6,150,383, U.S. Pat. No. 6,150,384, U.S. Pat. No. 6,166,042, U.S. Pat. No. 6,166,043, U.S. Pat. No. 6,172,090, U.S. Pat. No. 6,211,205, U.S. Pat. No. 6,271,243, U.S. Pat. No. 6,288,095, U.S. Pat. No. 6,303,640, U.S. Pat. No. 6,329,404, U.S. Pat. No. 5,994,554, WO97/10813, WO97/27857, WO97/28115, WO97/28137, WO97/27847, WO00/76488, WO03/000685, WO03/027112, WO03/035602, WO03/048130, WO03/055867, and pharmaceutically acceptable salts thereof; biguanides such as metformin hydrochloride (N,N-dimethylimidodicarbonimidic diamide hydrochloride, such as Glucophage™, Bristol-Myers Squibb); metformin hydrochloride with glyburide, such as Glucovance™, Bristol-Myers Squibb); buformin (Imidodicarbonimidic diamide, N-butyl-); etoformine (1-Butyl-2-ethylbiguanide, Schering A. G.); other metformin salt forms (including where the salt is chosen from the group of, acetate, benzoate, citrate, ftimarate, embonate, chlorophenoxyacetate, glycolate, palmoate, aspartate, methanesulphonate, maleate, parachlorophenoxyisobutyrate, formate, lactate, succinate, sulphate, tartrate, cyclohexanecarboxylate, hexanoate, octanoate, decanoate, hexadecanoate, octodecanoate, benzenesulphonate, trimethoxybenzoate, paratoluenesulphonate, adamantanecarboxylate, glycoxylate, glutamate, pyrrolidonecarboxylate, naphthalenesulphonate, 1-glucosephosphate, nitrate, sulphite, dithionate and phosphate), and phenformin; protein tyrosine phosphatase-IB (PTP-IB) inhibitors, such as A-401,674, KR 61639, OC-060062, OC-83839, OC-297962, MC52445, MC52453, ISIS 113715, and those disclosed in WO99/585521, WO99/58518, WO99/58522, WO99/61435, WO03/032916, WO03/032982, WO03/041729, WO03/055883, WO02/26707, WO02/26743, JP2002114768, and pharmaceutically acceptable salts and esters thereof; sulfonylureas such as acetohexamide (e.g. Dymelor, Eli Lilly), carbutamide, chlorpropamide (e.g. Diabinese®, Pfizer), gliamilide (Pfizer), gliclazide (e.g. Diamcron, Servier Canada Inc), glimepiride (e.g. disclosed in U.S. Pat. No. 4,379,785, such as Amaryl, Aventis), glipentide, glipizide (e.g. Glucotrol or Glucotrol XL Extended Release, Pfizer), gliquidone, glisolamide, glyburide/glibenclamide (e.g. Micronase or Glynase Prestab, Pharmacia & Upjohn and Diabeta, Aventis), tolazamide (e.g. Tolinase), and tolbutamide (e.g. Orinase), and pharmaceutically acceptable salts and esters thereof; meglitinides such as repaglinide (e.g. Pranidin®, Novo Nordisk), KAD1229 (PF/Kissei), and nateglinide (e.g. Starlix®, Novartis), and pharmaceutically acceptable salts and esters thereof; a glucoside hydrolase inhibitors (or glucoside inhibitors) such as acarbose (e.g. Precose™, Bayer disclosed in U.S. Pat. No. 4,904,769), miglitol (such as GLYSETT™, Pharmacia & Upjohn disclosed in U.S. Pat. No. 4,639,436), camiglibose (Methyl 6-deoxy-6-[(2R,3R,4R,5S)-3,4,5-trihydroxy-2-(hydroxymethyl)piperidino]-alpha-D-glucopyranoside, Marion Merrell Dow), voglibose (Takeda), adiposine, emiglitate, pradimicin-Q, salbostatin, CKD-711, MDL-25,637, MDL-73,945, and MOR 14, and the compounds disclosed in U.S. Pat. No. 4,062,950, U.S. Pat. No. 4,174,439, U.S. Pat. No. 4,254,256, U.S. Pat. No. 4,701,559, U.S. Pat. No. 4,639,436, U.S. Pat. No. 5,192,772, U.S. Pat. No. 4,634,765, U.S. Pat. No. 5,157,116, U.S. Pat. No. 5,504,078, U.S. Pat. No. 5,091,418, U.S. Pat. No. 5,217,877, U.S. Pat. No. 5,109,1 and WO 01/47528 (polyamines); α-amylase inhibitors such as tendamistat, trestatin, and Al-3688, and the compounds disclosed in U.S. Pat. No. 4,451,455, U.S. Pat. No. 4,623,714, and U.S. Pat. No. 4,273,765; SGLT2 inhibitors including those disclosed in U.S. Pat. No. 6,414,126 and U.S. Pat. No. 6,515,117; an aP2 inhibitor such as disclosed in U.S. Pat. No. 6,548,529; insulin secreatagogues such as linogliride, A-4166, forskilin, dibutyrl cAMP, isobutylmethylxanthine (IBMX), and pharmaceutically acceptable salts and esters thereof; fatty acid oxidation inhibitors, such as clomoxir, and etomoxir, and pharmaceutically acceptable salts and esters thereof; A2 antagonists, such as midaglizole, isaglidole, deriglidole, idazoxan, earoxan, and fluparoxan, and pharmaceutically acceptable salts and esters thereof; insulin and related compounds (e.g. insulin mimetics) such as biota, LP-100, novarapid, insulin detemir, insulin lispro, insulin glargine, insulin zinc suspension (lente and ultralente), Lys-Pro insulin, GLP-I (1-36) amide, GLP-I (73-7) (insulintropin, disclosed in U.S. Pat. No. 5,614,492), LY-315902 (Lilly), GLP-I (7-36)-NH2), AL-401 (Autoimmune), certain compositions as disclosed in U.S. Pat. No. 4,579,730, U.S. Pat. No. 4,849,405, U.S. Pat. No. 4,963,526, U.S. Pat. No. 5,642,868, U.S. Pat. No. 5,763,396, U.S. Pat. No. 5,824,638, U.S. Pat. No. 5,843,866, U.S. Pat. No. 6,153,632, U.S. Pat. No. 6,191,105, and WO 85/05029, and primate, rodent, or rabbit insulin including biologically active variants thereof including allelic variants, more preferably human insulin available in recombinant form (sources of human insulin include pharmaceutically acceptable and sterile formulations such as those available from Eli Lilly (Indianapolis, Ind. 46285) as Humulin™ (human insulin rDNA origin), also see the THE PHYSICIAN'S DESK REFERENCE, 55.sup.th Ed. (2001) Medical Economics, Thomson Healthcare (disclosing other suitable human insulins); non-thiazolidinediones such as JT-501 and farglitazar (GW-2570/GI-262579), and pharmaceutically acceptable salts and esters thereof; PPARα/γ dual agonists such as AR-H039242 (Aztrazeneca), GW-409544 (Glaxo-Wellcome), BVT-142, CLX-0940, GW-1536, GW-1929, GW-2433, KRP-297 (Kyorin Merck; 5-[(2,4-Dioxo thiazolidinyl)methyl]methoxy-N-[[4-(trifluoromethyl)phenyl]methyl]benzamide), L-796449, LR-90, MK-0767 (Merck/Kyorin/Banyu), SB 219994, muraglitazar (BMS), tesaglitzar (Astrazeneca), reglitazar (JTT-501) and those disclosed in WO99/16758, WO99/19313, WO99/20614, WO99/38850, WO00/23415, WO00/23417, WO00/23445, WO00/50414, WO01/00579, WO01/79150, WO02/062799, WO03/004458, WO03/016265, WO03/018010, WO03/033481, WO03/033450, WO03/033453, WO03/043985, WO 031053976, U.S. application Ser. No. 09/664,598, filed Sep. 18, 2000, Murakami et al. Diabetes 47, 1841-1847 (1998), and pharmaceutically acceptable salts and esters thereof; other insulin sensitizing drugs; VPAC2 receptor agonists; GLK modulators, such as those disclosed in WO03/015774; retinoid modulators such as those disclosed in WO03/000249; GSK 3β/GSK 3 inhibitors such as 4-[2-(2-bromophenyl)-4-(4-fluorophenyl-1H-imidazol-5-yl]pyridine and those compounds disclosed in WO03/024447, WO03/037869, WO03/037877, WO03/037891, WO03/068773, EP1295884, EP1295885, and the like; glycogen phosphorylase (HGLPa) inhibitors such as CP-368,296, CP-316,819, BAYR3401, and compounds disclosed in WO 01/94300, WO02/20530, WO03/037864, and pharmaceutically acceptable salts or esters thereof; ATP consumption promotors such as those disclosed in WO03/007990; TRB3 inhibitors; vanilloid receptor ligands such as those disclosed in WO03/049702; hypoglycemic agents such as those disclosed in WO03/015781 and WO03/040114; glycogen synthase kinase 3 inhibitors such as those disclosed in WO03/035663 agents such as those disclosed in WO99/51225, US20030134890, WO01/24786, and WO03/059870; insulin-responsive DNA binding protein-1 (IRDBP-I) as disclosed in WO03/057827, and the like; adenosine A2 antagonists such as those disclosed in WO03/035639, WO03/035640, and the like; PPARδ agonists such as GW 501516, GW 590735, and compounds disclosed in JP10237049 and WO02/14291; dipeptidyl peptidase IV (DP-IV) inhibitors, such as isoleucine thiazolidide, NVP-DPP728A (1-[[[2-[(5-cyanopyridin-2-yl)amino]ethyl]amino]acetyl]-2-cyano-(S)-pyrrolidine, disclosed by Hughes et al, Biochemistry, 38(36), 11597-11603, 1999), P32/98, NVP-LAF-237, P3298, TSL225 (tryptophyl-1,2,3,4-tetrahydro-isoquinoline-3-carboxylic acid, disclosed by Yamada et al, Bioorg. & Med. Chem. Lett. 8 (1998) 1537-1540), valine pyrrolidide, TMC-2A/2B/2C, CD-26 inhibitors, FE999011, P9310/K364, VIP 0177, DPP4, SDZ 274-444, 2-cyanopyrrolidides and 4-cyanopyrrolidides as disclosed by Ashworth et al, Bioorg. & Med. Chem. Lett., Vol. 6, No. 22, pp 1163-1166 and 2745-2748 (1996), and the compounds disclosed in U.S. Pat. No. 6,395,767, U.S. Pat. No. 6,573,287, U.S. Pat. No. 6,395,767 (compounds disclosed include BMS-477118, BMS-471211 and BMS 538, 305), WO99/38501, WO99/46272, WO99/67279, WO99/67278, WO99/61431WO03/004498, WO03/004496, EP1258476, WO02/083128, WO02/062764, WO03/000250, WO03/002530, WO03/002531, WO03/002553, WO03/002593, WO03/000180, and WO03/000181; GLP-I agonists such as exendin-3 and exendin-4 (including the 39 aa polypeptide synthetic exendin-4 called Exenatide®), and compounds disclosed in US2003087821 and NZ 504256, and pharmaceutically acceptable salts and esters thereof; peptides including amlintide and Symlin® (pramlintide acetate); and glycokinase activators such as those disclosed in US2002103199 (fused heteroaromatic compounds) and WO02/48106 (isoindolin-1-one-substituted propionamide compounds).

Phosphodiesterase Inhibitors

The GCRA peptides described herein can be used in combination therapy with a phosphodiesterase inhibitor. PDE inhibitors are those compounds which slow the degradation of cyclic AMP (cAMP) and/or cyclic GMP (cGMP) by inhibition of the phosphodiesterases, which can lead to a relative increase in the intracellular concentration of c AMP and/or cGMP. Possible PDE inhibitors are primarily those substances which are to be numbered among the class consisting of the PDE3 inhibitors, the class consisting of the PDE4 inhibitors and/or the class consisting of the PDE5 inhibitors, in particular those substances which can be designated as mixed types of PDE3/4 inhibitors or as mixed types of PDE3/4/5 inhibitors. By way of example, those PDE inhibitors may be mentioned such as are described and/or claimed in the following patent applications and patents: DE1470341, DE2108438, DE2123328, DE2305339, DE2305575, DE2315801, DE2402908, DE2413935, DE2451417, DE2459090, DE2646469, DE2727481, DE2825048, DE2837161, DE2845220, DE2847621, DE2934747, DE3021792, DE3038166, DE3044568, EP000718, EP0008408, EP0010759, EP0059948, EP0075436, EP0096517, EPO1 12987, EPO1 16948, EP0150937, EP0158380, EP0161632, EP0161918, EP0167121, EP0199127, EP0220044, EP0247725, EP0258191, EP0272910, EP0272914, EP0294647, EP0300726, EP0335386, EP0357788, EP0389282, EP0406958, EP0426180, EP0428302, EP0435811, EP0470805, EP0482208, EP0490823, EP0506194, EP0511865, EP0527117, EP0626939, EP0664289, EP0671389, EP0685474, EP0685475, EP0685479, JP92234389, JP94329652, JP95010875, U.S. Pat. Nos. 4,963,561, 5,141, 931, WO91/17991, WO9200968, WO9212961, WO9307146, WO9315044, WO9315045, WO9318024, WO9319068, WO9319720, WO9319747, WO9319749, WO9319751, WO9325517, WO9402465, WO9406423, WO9412461, WO9420455, WO9422852, WO9425437, WO9427947, WO9500516, WO9501980, WO9503794, WO9504045, WO9504046, WO9505386, WO9508534, WO9509623, WO9509624, WO9509627, WO9509836, WO9514667, WO9514680, WO9514681, WO9517392, WO9517399, WO9519362, WO9522520, WO9524381, WO9527692, WO9528926, WO9535281, WO9535282, WO9600218, WO9601825, WO9602541, WO9611917, DE3142982, DE1 116676, DE2162096, EP0293063, EP0463756, EP0482208, EP0579496, EP0667345 U.S. Pat. No. 6,331,543, US20050004222 (including those disclosed in formulas I-XIII and paragraphs 37-39, 85-0545 and 557-577) and WO9307124, EP0163965, EP0393500, EP0510562, EP0553174, WO9501338 and WO9603399. PDE5 inhibitors which may be mentioned by way of example are RX-RA-69, SCH-51866, KT-734, vesnarinone, zaprinast, SKF-96231, ER-21355, BF/GP-385, NM-702 and sildenafil (Viagra®). PDE4 inhibitors which may be mentioned by way of example are RO-20-1724, MEM 1414 (R1533/R1500; Pharmacia Roche), DENBUFYLLINE, ROLIPRAM, OXAGRELATE, NITRAQUAZONE, Y-590, DH-6471, SKF-94120, MOT-APIZONE, LIXAZINONE, INDOLIDAN, OLPRINONE, ATIZORAM, KS-506-G, DIPAMFYLLINE, BMY-43351, ATIZORAM, AROFYLLINE, FILAMINAST, PDB-093, UCB-29646, CDP-840, SKF-107806, PICLAMILAST, RS-17597, RS-25344-000, SB-207499, TIBENELAST, SB-210667, SB-211572, SB-211600, SB-212066, SB-212179, GW-3600, CDP-840, MOPIDAMOL, ANAGRELIDE, IBUDILAST, AMRINONE, PIMOBENDAN, CILOSTAZOL, QUAZINONE and N-(3,5-dichloro-pyrid-4-yl)-3-cyclopropylmethoxy-4-difluoromethoxybenzamide. PDE3 inhibitors which may be mentioned by way of example are SULMAZOLE, AMPIZONE, CILOSTAMIDE, CARBAZERAN, PIROXIMONE, IMAZODAN, CI-930, SIGUAZODAN, ADIBENDAN, SATERINONE, SKF-95654, SDZ-MKS-492, 349-U-85, EMORADAN, EMD-53998, EMD-57033, NSP-306, NSP-307, REVIZINONE, NM-702, WIN-62582 and WIN-63291, ENOXIMONE and MILRINONE. PDE3/4 inhibitors which may be mentioned by way of example are BENAFENTRINE, TREQUINSIN, ORG-30029, ZARDAVERINE, L-686398, SDZ-ISQ-844, ORG-20241, EMD-54622, and TOLAFENTRINE. Other PDE inhibitors include: cilomilast, pentoxifylline, roflumilast, tadalafil(Clalis®), theophylline, and vardenafil(Levitra®), zaprinast (PDE5 specific).

Anti-Uterine Contractions Agents

The GCRA peptides described herein can be used in combination therapy (for example, in order to decrease or inhibit uterine contractions) with a tocolytic agent including but not limited to beta-adrenergic agents, magnesium sulfate, prostaglandin inhibitors, and calcium channel blockers.

Anti-Neoplastic Agents

The GCRA peptides described herein can be used in combination therapy with an antineoplastic agents including but not limited to alkylating agents, epipodophyllotoxins, nitrosoureas, antimetabolites, vinca alkaloids, anthracycline antibiotics, nitrogen mustard agents, and the like. Particular anti-neoplastic agents may include tamoxifen, taxol, etoposide and 5-fluorouracil.

The GCRA peptides described herein can be used in combination therapy (for example as in a chemotherapeutic composition) with an antiviral and monoclonal antibody therapies.

Agents to Treat Congestive Heart Failure

The GCRA peptides described herein can be used in combination therapy (for example, in prevention/treatment of congestive heart failure or another method described herein) with the partial agonist of the nociceptin receptor ORL1 described by Dooley et al. (The Journal of Pharmacology and Experimental Therapeutics, 283 (2): 735-741, 1997). The agonist is a hexapeptide having the amino acid sequence Ac-RYY (RK) (WI) (RK)-NH2 ("the Dooley polypeptide"), where the brackets show allowable variation of amino acid residue. Thus Dooley polypeptide can include but are not limited to KYYRWR (SEQ ID NO: 109), RYYRWR (SEQ ID NO: 110), KWRYYR (SEQ ID NO: 111), RYYRWK (SEQ ID NO: 112), RYYRWK (all-D amin acids) (SEQ ID NO: 113), RYYRIK (SEQ ID NO: 114), RYYRIR (SEQ ID NO: 115), RYYKIK (SEQ ID NO: 116), RYYKIR (SEQ ID NO: 117), RYYKWR (SEQ ID NO: 118), RYYKWK (SEQ ID NO: 119), RYYRWR (SEQ ID NO: 120), and KYYRWK (SEQ ID NO: 121), wherein the amino acid residues are in the L-form unless otherwise specified. The GCRA peptides described herein can also be used in combination therapy with polypeptide conjugate modifications of the Dooley polypeptide described in WO0198324.

Dosage

Dosage levels of active ingredients in a pharmaceutical composition can also be varied so as to achieve a transient or sustained concentration of the compound in a subject, especially in and around the site of inflammation or disease area, and to result in the desired response. It is well within the skill of the art to start doses of the compound at levels lower than required to achieve the desired effect and to gradually increase the dosage until the desired effect is achieved. It will be understood that the specific dose level for any particular subject will depend on a variety of factors, including body weight, general health, diet, natural history of disease, route and scheduling of administration, combination with one or more other drugs, and severity of disease.

An effective dosage of the composition will typically be between about 1 μg and about 10 mg per kilogram body weight, preferably between about 10 μg to 5 mg of the compound per kilogram body weight. Adjustments in dosage will be made using methods that are routine in the art and will be based upon the particular composition being used and clinical considerations.

The guanylate cyclase receptor agonists used in the methods described above may be administered orally, systemically or locally. Dosage forms include preparations for inhalation or injection, solutions, suspensions, emulsions, tablets, capsules, topical salves and lotions, transdermal compositions, other known peptide formulations and pegylated peptide analogs. Agonists may be administered as either the sole active agent or in combination with other drugs, e.g., an inhibitor of cGMP-dependent phosphodiesterase and anti-inflammatory agent. In all cases, additional drugs should be administered at a dosage that is therapeutically effective using the existing art as a guide. Drugs may be administered in a single composition or sequentially.

Dosage levels of the GCR agonist for use in methods of this invention typically are from about 0.001 mg to about 10,000 mg daily, preferably from about 0.005 mg to about 1,000 mg daily. On the basis of mg/kg daily dose, either given in single or divided doses, dosages typically range from about 0.001/75 mg/kg to about 10,000/75 mg/kg, preferably from about 0.005/75 mg/kg to about 1,000/75 mg/kg.

The total daily dose of each inhibitor can be administered to the patient in a single dose, or in multiple subdoses. Typically, subdoses can be administered two to six times per day, preferably two to four times per day, and even more preferably two to three times per day. Doses can be in immediate release form or sustained release form sufficiently effective to obtain the desired control over the medical condition.

The dosage regimen to prevent, treat, give relief from, or ameliorate a medical condition or disorder, or to otherwise protect against or treat a medical condition with the combinations and compositions of the present invention is selected in accordance with a variety of factors. These factors include, but are not limited to, the type, age, weight, sex, diet, and medical condition of the subject, the severity of the disease, the route of administration, pharmacological considerations such as the activity, efficacy, pharmacokinetics and toxicology profiles of the particular inhibitors employed, whether a drug delivery system is utilized, and whether the inhibitors are administered with other active ingredients. Thus, the dosage regimen actually employed may vary widely and therefore deviate from the preferred dosage regimen set forth above.

EXAMPLES

Example 1

Synthesis and Purification of Gcra Peptides

The GCRA peptides were synthesized using standard methods for solid-phase peptide synthesis. Either a Boc/Bzl or Fmoc/tBu protecting group strategy was selected depending upon the scale of the peptide to be produced. In the case of smaller quantities, it is possible to get the desired product using an Fmoc/tBu protocol, but for larger quantities (1 g or more), Boc/Bzl is superior.

In each case the GCRA peptide was started by either using a pre-loaded Wang (Fmoc) or Merrifield (Boc) or Pam (Boc) resin. For products with C-terminal Leu, Fmoc-Leu-Wang (D-1115) or Boc-Leu-Pam resin (D-1230) or Boc-Leu-Merrifield (D-1030) Thus, for peptides containing the C-terminal d-Leu, the resin was Fmoc-dLeu-Wang Resin (D-2535) and Boc-dLeu-Merrifield, Boc-dLeu-Pam-Resin (Bachem Product D-1230 and D-1590, respectively) (SP-332 and related analogs). For peptides produced as C-terminal amides, a resin with Ramage linker (Bachem Product D-2200) (Fmoc) or mBHA (Boc) (Bachem Product D-1210 was used and loaded with the C-terminal residue as the first synthetic step.

Fmoc-tBu Overview

Each synthetic cycle consisted deprotection with 20% piperidine in DMF. Resin washes were accomplished with alternating DMF and IpOH to swell and shrink the resin, respectively. Peptide synthesis elongated the chain from the C-terminus to the N-terminus. Activation chemistry for each amino acid was with HBTU/DIEA in a 4 fold excess for 45 minutes. In automated chemistries, each amino acid was double coupled to maximize the coupling efficiency. To insure the correct position of disulfide bonds, the Cys residues were introduced as Cys(Acm) at positions 15 and 7. Cys(Trt) was positioned at Cys4 and Cys12. This protecting group strategy yields the correct topoisomer as the dominant product (75:25). (For enterotoxin analogs, a third disulfide bond protecting group (Mob) was utilized).

For peptides containing C-terminal Aeea (aminoethyloxyethyloxyacetyl) groups, these were coupled to a Ramage amide linker using the same activation chemistry above by using an Fmoc-protected Aeea derivative. The Cys numbering in these cases remains the same and the positioning of the protecting groups as well. For the peptides containing the N-terminal extension of Aeea, the Cys residue numbering will be increased by three Cys4 becomes Cys7, Cys12 becomes Cys15; Cys7 becomes Cys10 and Cys 15 becomes Cys18. The latter pair is protected with Acm and the former pair keeps the Trt groups.

For analogs containing D-amino acid substitutions, these were introduced directly by incorporating the correctly protected derivative at the desired position using the same activation chemistry described in this document. For Fmoc strategies, Fmoc-dAsn(Trt)-OH, Fmoc-dAsn(Xan)-OH, Fmoc-dAsp(tBu)-OH, Fmoc-dGlu(tBu)-OH and for Boc strategies, Boc-dAsn(Xan)-OH, Boc-dAsn(Trt)-OH, Boc-dAsp(Chx), Boc-dAsp(Bzl)-OH, Boc-dGlu(Chx)-OH and Boc-dGlu (Bzl)-OH would be utilized.

Each peptide is cleaved from the solid-phase support using a cleavage cocktail of TFA:H2O:Trisisopropylsilane (8.5:0.75:0.75) ml/g of resin for 2 hr at RT. The crude deprotected peptide is filtered to remove the spent resin beads and precipitated into ice-cold diethylether.

Each disulfide bonds was introduced orthogonally. Briefly, the crude synthetic product was dissolved in water containing $NH_4OH$ to increase the pH to 9. Following complete solubilization of the product, the disulfide bond was made between the Trt deprotected Cys residues by titration with $H_2O_2$. The monocyclic product was purified by RP-HPLC. The purified mono-cyclic product was subsequently treated with a solution of iodine to simultaneously remove the Acm protecting groups and introduce the second disulfide bond.

For enterotoxin analogs, the Mob group was removed via treatment of the dicyclic product with TFA 85% containing 10% DMSO and 5% thioanisole for 2 hr at RT.

Each product was then purified by RP-HPLC using a combination buffer system of TEAP in H2O versus MeCN, followed by TFA in H2O versus MeCN. Highly pure fractions were combined and lyophilized. The final product was converted to an Acetate salt using either ion exchange with Acetate loaded Dow-Ex resin or using RP-HPLC using a base-wash step with $NH_4OAc$ followed by 1% AcOH in water versus MeCN.

It is also possible to prepare enterotoxin analogs using a random oxidation methodology using Cys(Trt) in Fmoc or Cys(MeB) in Boc. Following cleavage, the disulfide bonds can be formed using disulfide interchange redox pairs such as glutathione (red/ox) and/or cysteine/cystine. This process will yield a folded product that the disulfide pairs must be determined as there would be no way of knowing their position directly.

Boc-Bzl Process

Peptide synthesis is initiated on a Merrifield or Pam preloaded resin or with mBHA for peptides produced as C-terminal amides. Each synthetic cycle consists of a deprotection step with 50% TFA in MeCL2. The resin is washed repetitively with MeCl2 and MeOH. The TFA salt formed is neutralized with a base wash of 10% TEA in MeCl2. The resin is washed with MeCl2 and MeOH and lastly with DMF prior to coupling steps. A colorimetric test is conducted to ensure deprotection. Each coupling is mediated with diisopropyl carbodiimide with HOBT to form the active ester. Each coupling is allowed to continue for 2 hr at RT or overnight on difficult couplings. Recouplings are conducted with either Uronium or Phosphonium reagents until a negative colorimetric test is obtained for free primary amines. The resin is then washed with DMF, MeCl2 and MeOH and prepared for the next solid-phase step. Cys protection utilizes Cys(Acm) at positions 7 and 15, and Cys(MeB) at Cys 4 and Cys12.

Cleavage and simultaneous deprotection is accomplished by treatment with HF using anisole as a scavenger (9:1:1) ml:ml:g (resin) at 0° C. for 60 min. The peptide is subsequently extracted from the resin and precipitated in ice cold ether. The introduction of disulfide bonds and purification follows the exact same protocol described above for the Fmoc produced product.

Example 2

In Vitro Proteolytic Stability Using Simulated Gastric Fluid (SGF) Digestion

The stability of SP-304 in the presence of simulated gastric fluid (SGF) was determined. SP-304 (final concentration of 8.5 mg/ml) was incubated in SGF (Proteose peptone (8.3 g/liter; Difco), D-Glucose (3.5 g/liter; Sigma), NaCl (2.05 g/liter; Sigma), $KH_2PO_4$ (0.6 g/liter; Sigma), $CaCl_2$ (0.11 g/liter), KCl (0.37 g/liter; Sigma), Porcine bile (final 1× concentration 0.05 g/liter; Sigma) in PBS, Lysozyme (final 1× concentration 0.10 g/liter; Sigma) in PBS, Pepsin (final 1× concentration 0.0133 g/liter; Sigma) in PBS). SGF was made on the day of the experiment and the pH was adjusted to 2.0±0.1 using HCl or NaOH as necessary. After the pH adjustment, SGF is filter sterilized with 0.22 μm membrane filters. SP-304 (final concentration of 8.5 mg/ml) was incubated in SGF at 37° C. for 0, 15, 30, 45, 60 and 120 min, respectively, in triplicate aliquots. Following incubations, samples were snap frozen in dry ice then stored in a −80° C. freezer until assayed in duplicate.

FIG. 1A is a bar chart showing the biological activity of SP-304 after incubation with SGF for times as indicated. The activity at 0 min was taken as 100%. The data are an average of triplicates±SD for each data point. The data demonstrate that SP-304 is not sensitive to digestion with SGF. In addition, the data also suggest that the activity of SP-304 is not affected by exposure to the acidic pH of the SGF.

Figure 1B:
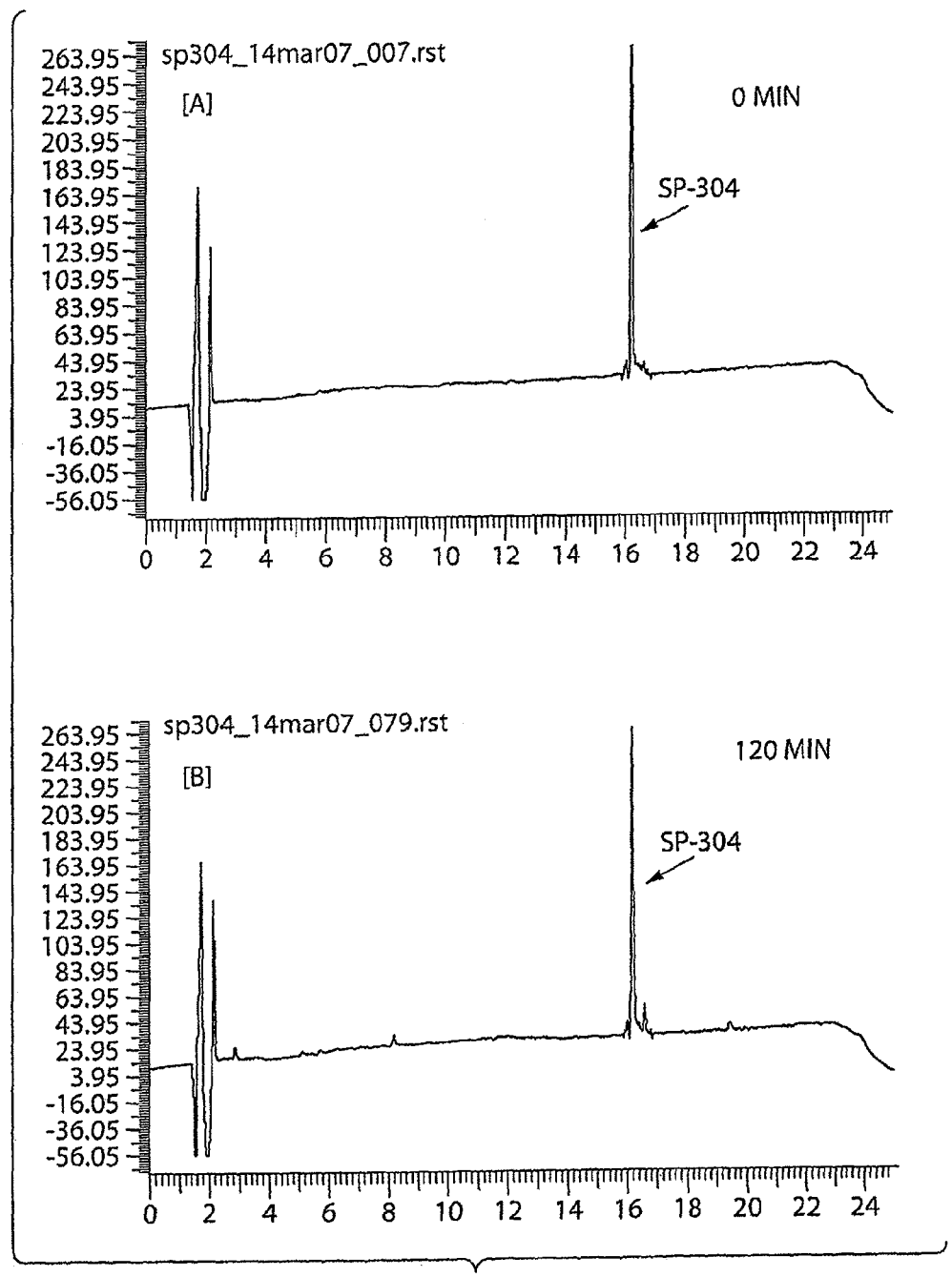
FIG. 1B is a schematic representation of the results of HPLC chromatographic analyses of SP-304 samples after incubation with SGF at indicated times. The major peak of SP-304 did not change following incubation with SGF, indicating that the peptide was resistant to SGF digestion. The arrows indicate the elution position of SP-304.

These results were further confirmed by the HPLC analyses of the samples after digestion with SGF. Here, aliquots of samples from all digestions were analyzed using a previously developed method for analyzing SP-304 peptide using HPLC. Samples from the SGF digestions were diluted to give a final concentration 0.17 mg/mL of SP-304. FIG. 1B shows HPLC chromatographs of SP-304 samples after incubation with SGF at indicated times. The major peak of SP-304 did not change following digestion with SGF, indicating that the peptide was resistant to SGF digestion.

Example 3

Figure 2A:
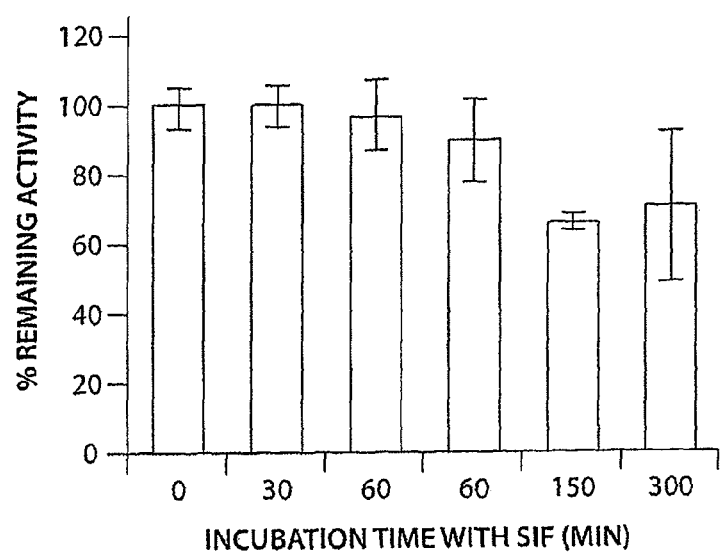
FIG. 2A is a bar chart showing Cyclic GMP synthesis in T84 cells by SP304 samples after incubation with simulated intestinal fluid (SIF) for the indicated times. Following the incubations, samples were used for their abilities to stimulate cGMP synthesis in T84 cells. The cGMP stimulation activity in sample at 0 min of incubation with SIF was taken as 100%. The activities in samples from other times of incubations with SIF were calculated as percentage of the activity in the sample at 0 min. The data is average of triplicates±SD

In Vitro Proteolytic Stability Using Simulated Intestinal Fluid (SIF) Digestion The stability of SP-304 was also evaluated after incubation with simulated intestinal fluid (SIF). SIF solution was prepared by the method as described in the United States Pharmacopoeia, 24th edition, p2236. The recipe to prepare SIF solution was as described below. The SIF solution contained NaCl (2.05 g/liter; Sigma), $KH_2PO_4$ (0.6 g/liter; Sigma), $CaCl_2$ (0.11 g/liter), KCl (0.37 g/liter; Sigma), and Pacreatin 10 mg/ml. The pH was adjusted to 6 and the solution was filter sterilized. A solution of SP-304 (8.5 mg/ml) was incubated in SGF at 37° C. for 0, 30, 60, 90, 120, 150 and 300 min respectively, in triplicate aliquots. Following incubations, samples were removed and snap frozen with dry ice and stored in a −80° C. freezer until assayed in duplicate. FIG. 2A is a bar chart showing the ability of SP-304, after incubation in SIF for times as indicated, to stimulate cGMP synthesis in T84 cells. The cGMP stimulation activity at 0 min was taken as 100%. The data are an average of 3 triplicates±SD. The data indicated that the biological activity of SP-304 is reduced by 30% following digestion with ST. This could be due to degradation of the peptide. Hence, samples after digestion with SIF were further analyzed by HPLC.

Figure 2B:
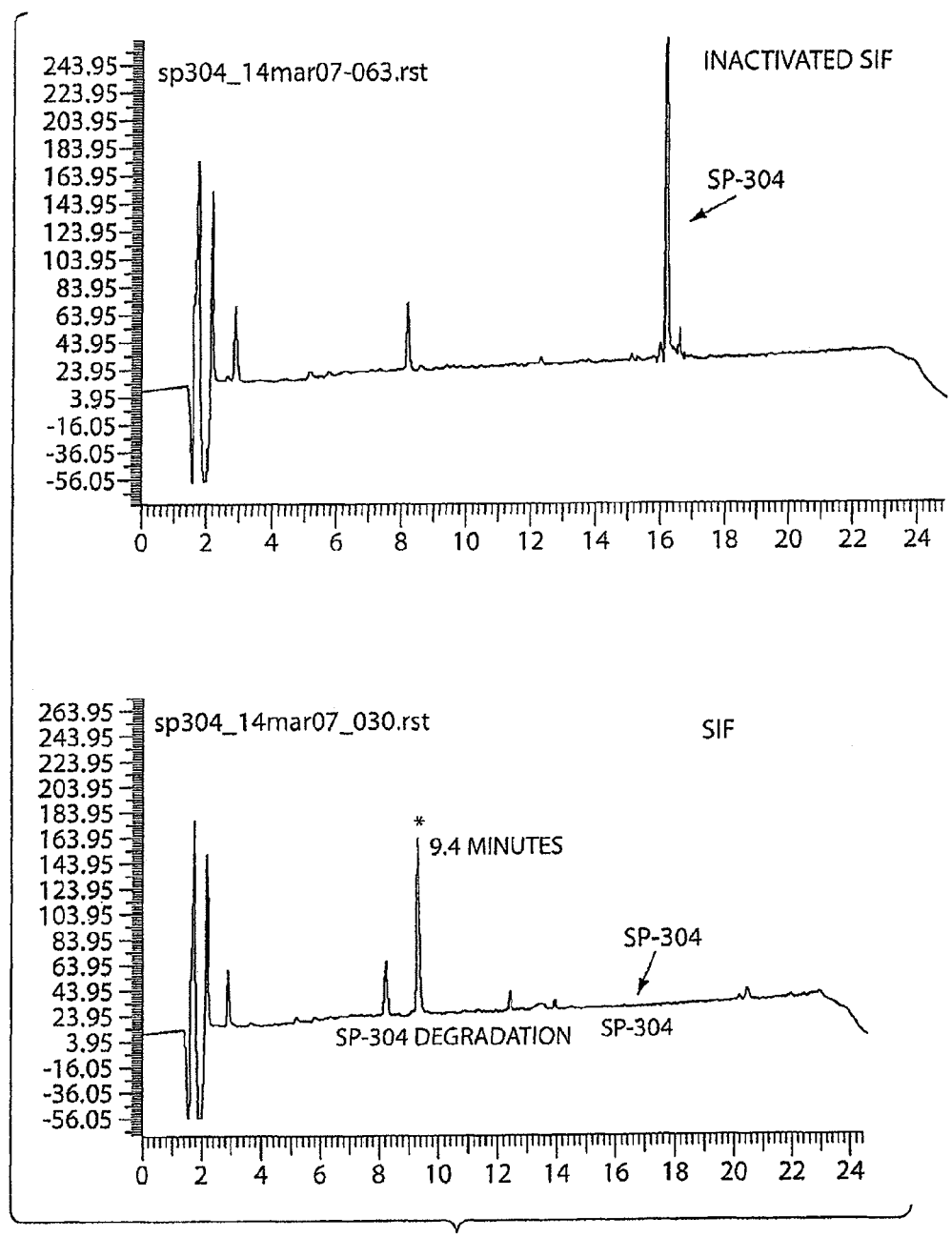
FIG. 2B is a schematic representation of the results of HPLC chromatographic analyses of SP304 samples after incubation with (A) heat inactivated SIF for 300 min or with (B) SIF for 120 min. The incubation with SIF completely converted SP-304 into another peptide eluting at 9.4 min, as indicated by *. Arrows indicate the position of SP-304.

The integrity of SP-340 peptide exposed to ST was evaluated by HPLC by essentially using the method described for SGF digestion. FIG. 2B is a schematic representation of the results of HPLC chromatographic analyses of SP-304 samples after incubation with heat-inactivated SIF for 300 min, and SIF for 120 min, respectively. The major peak of SP-304, which elutes at 16.2 min was converted into another peak at 9.4 min and a few minor peptide peaks. Thus, it was important to find out structures of the metabolites of SP-304 produced after digestion with SIF. SP-304 peptide was incubated with ST for various times and the peptide digestion products were isolated and subjected to structure elucidation by MS analysis.

Figure 3:
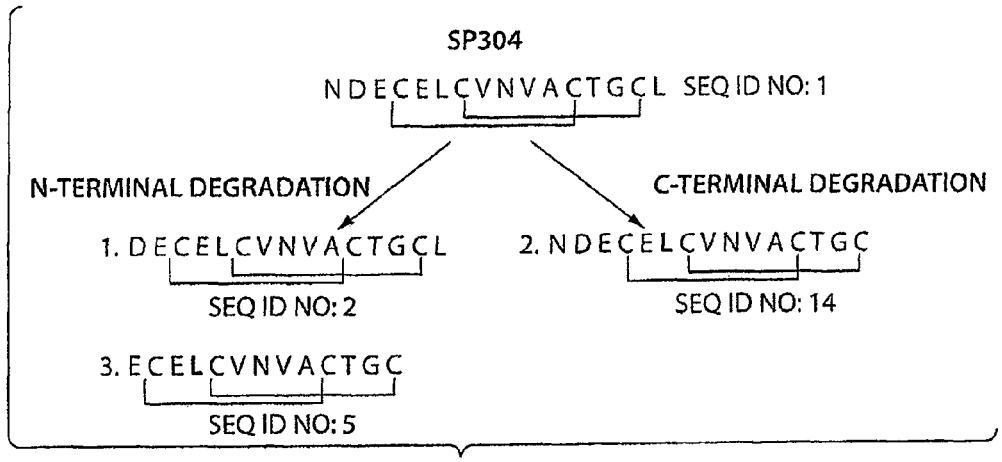
FIG. 3 is a schematic representation of the possible degradation products of SP-304.

FIG. 3 is a schematic representation of the possible metabolites of SP-304. The major degradation products involve N and D clipped from the N-terminus and L from the C-terminus of SP304. However, there was only 30% reduction in biological activity, implying that one or more of the degradation products were also biologically active. To address this possibility, several truncated peptides were synthesized and evaluated for their abilities to stimulate cGMP synthesis in T84 cells (FIG. 4).

Figure 4:
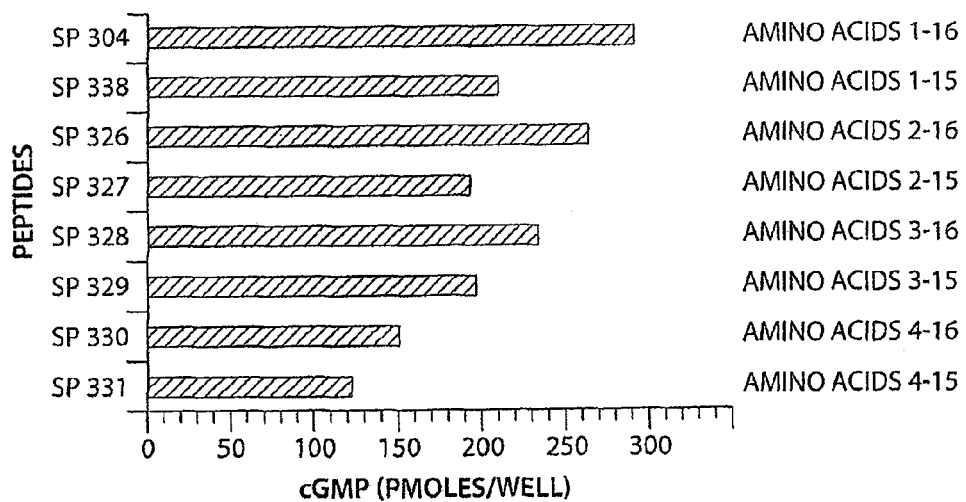
FIG. 4 shows stimulation of cGMP synthesis in T84 cells by the truncated peptides of SP-304. Thus, SP-338 has the same peptide sequence as SP-304 except that it lacks Leu at the C-terminus. Similarly, SP-327, SP-329 and SP-331 have Leu at their C-termini deleted relative to their corresponding parents, SP-326, SP-328 and SP-330. Peptides were evaluated for their abilities to stimulate cGMP synthesis in T84 cells. The results are expressed as an average of duplicates.

FIG. 4 shows data from the analyses of various peptides in the T84 cell cGMP stimulation assay (essentially as described in Shailubhai, et al., Cancer Research 60, 5151-5157 (2000). Briefly, confluent monolayers of T-84 cells in 24-well plates were washed twice with 250 μl of DMEM containing 50 mM HEPES (pH 7.4) and pre-incubated at 37° C. for 10 minutes with 250 μl of DMEM containing 50 mM HEPES (pH 7.4) and 1 mM isobutyl methylxanthine (IBMX). Monolayers of T84 cells were then incubated with 250 μl of DMEM containing 50 mM HEPES (pH 7.4) containing one of the peptides shown in the FIG. 4 at a concentration of 1.0 μM for 30 min. After the 30 min incubation, the medium was aspirated and the reaction was terminated by the addition of 3% perchloric acid. Following centrifugation and the addition of NaOH (0.1 N) to neutralize the pH, intracellular cGMP levels were determined in lysates using a cGMP ELISA kit (Cat. No. 581021; Cayman Chemical, Ann Arbor, Mich.). Samples were run in duplicates incubations and each sample was run as duplicates in ELISA test.

The data suggest that the leucine (L) residue at the C-terminus of SP-304 contributes to the biological potency of the peptide. For example, there was considerable reduction in potency when L was deleted from SP-304, as in SP-338. Similarly, the peptides SP-327, SP-329 and SP-331, without L at the C-terminal, also showed 20-25% reduction in biological potency as compared to their counterpart peptides with L at the C-terminus, as in SP-326, SP-328 and SP-330 peptides. In addition, results also suggest that amino acid residues at the N-terminus might also be important for stability and/or potency of the peptides. Based on these results, several new peptides were synthesized with D-forms of amino acids replacing the corresponding L-forms at the C- and N-termini of the peptides. These peptides were evaluated for their abilities to stimulate cGMP synthesis in T84 cells as shown in FIG. 5.

Figure 5:
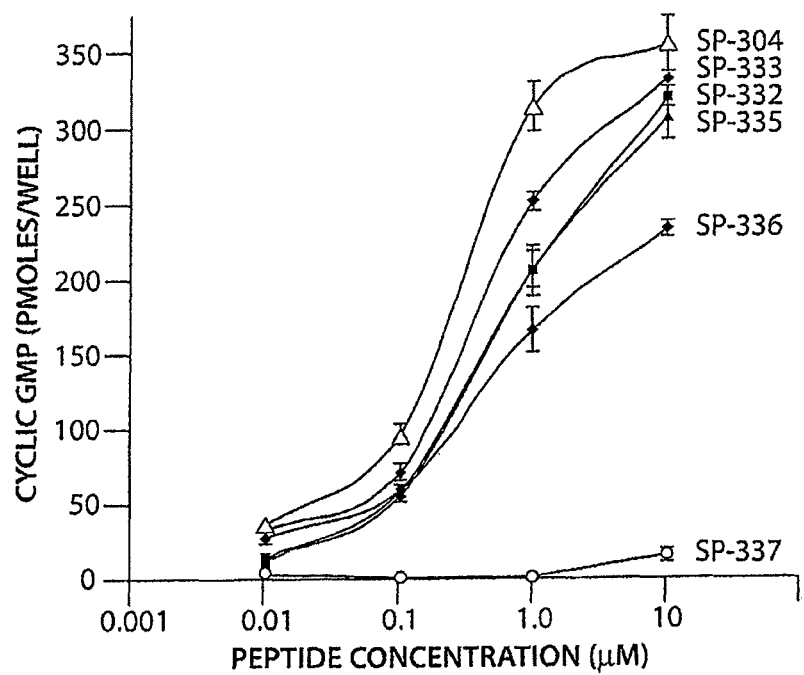
FIG. 5 shows stimulation of cGMP synthesis in T84 cells by SP-304 and similar peptides. Cells were exposed to peptide analogs for 30 min and cell lysates were used to determine intracellular cGMP levels. Results are expressed as an average of triplicates±SD.

The results presented in FIG. 5 suggest that substitution of L-amino acids with D-amino acids at the C- and N-termini did not significantly alter their potency. Peptides SP-332, SP-333 and SP-335 showed comparable ability to stimulate cGMP synthesis in T84 cells. On the other hand, the substitution of L-leucine with D-leucine at the $6^{th}$ position in SP-337 resulted in a complete loss in its ability to stimulate cGMP synthesis in T84 cells. These results suggest that the amino acid residues Asn, Asp and Glu at the N-terminus and Leu at the C-terminus can be replaced with their respective D-amino acid forms. However, the leucine at the $6^{th}$ position can not be replaced with its D-form.

FIG. 7 (A-F) shows the stabilities of peptides SP-332, SP-333 and SP-304 when incubated with SIF for two hours. The results demonstrated that the peptide SP-333, which has D-Asn at the N-terminus and D-Leu at the C-terminus, was virtually completely resistant to digestion with SIF (FIG. 7F), and remained virtually 100% biologically active after a two hour incubation in SIF (FIG. 7A). The peptide SP-332 with D-Leu at the C-terminus showed some reduction in potency following the 120 min incubation with SIF (FIG. 7B). However, the HPLC analyses of SP-332 did not reveal any degradation of the peptide (FIG. 7E), suggesting that these peptides are completely resistant to proteoysis by SIF. On the other hand, the peptide SP-304 lost about 30% of its potency following digestion with SIF for just one hour (FIG. 7C). The HPLC analysis of SP-304 following SIF incubation confirmed its degradation (FIG. 7D). These results suggest that the peptide SP-304 undergoes proteolysis following incubation with SIF, whereas substitution of L-Asn with D-Asn at the N-terminus plus the substitution of L-Leu with D-Leu at the C-terminus protects SP-333 against digestion with SIF. Thus, the peptide SP-333 appears more stable and potent as a drug candidate.

Example 4

Cyclic GMP Stimulation Assays

The ability of the GCRA peptide to bind to and activate the intestinal GC-C receptor was tested by using T 84 human colon carcinoma cell line. Human T84 colon carcinoma cells were obtained from the American Type Culture Collection. Cells were grown in a 1:1 mixture of Ham's F-12 medium and Dulbecco's modified Eagle's medium (DMEM) supplemented with 10% fetal bovine serum, 100 U penicillin/ml, and 100 µg/ml streptomycin. The cells were fed fresh medium every third day and split at a confluence of approximately 80%.

Biological activity of the GCRA peptides was assayed as previously reported (Shailubhai, et al., Cancer Research 60, 5151-5157 (2000)). Briefly, the confluent monolayers of T-84 cells in 24-well plates were washed twice with 250 µl of DMEM containing 50 mM HEPES (pH 7.4), pre-incubated at 37° C. for 10 min with 250 µl of DMEM containing 50 mM HEPES (pH 7.4) and 1 mM isobutylmethylxanthine (IBMX), followed by incubation with GCRA peptides (0.1 nM to 10 .mu.M) for 30 min. The medium was aspirated, and the reaction was terminated by the addition of 3% perchloric acid. Following centrifugation, and neutralization with 0.1 N NaOH, the supernatant was used directly for measurements of cGMP using an ELISA kit (Caymen Chemical, Ann Arbor, Mich.).

Figure 6:
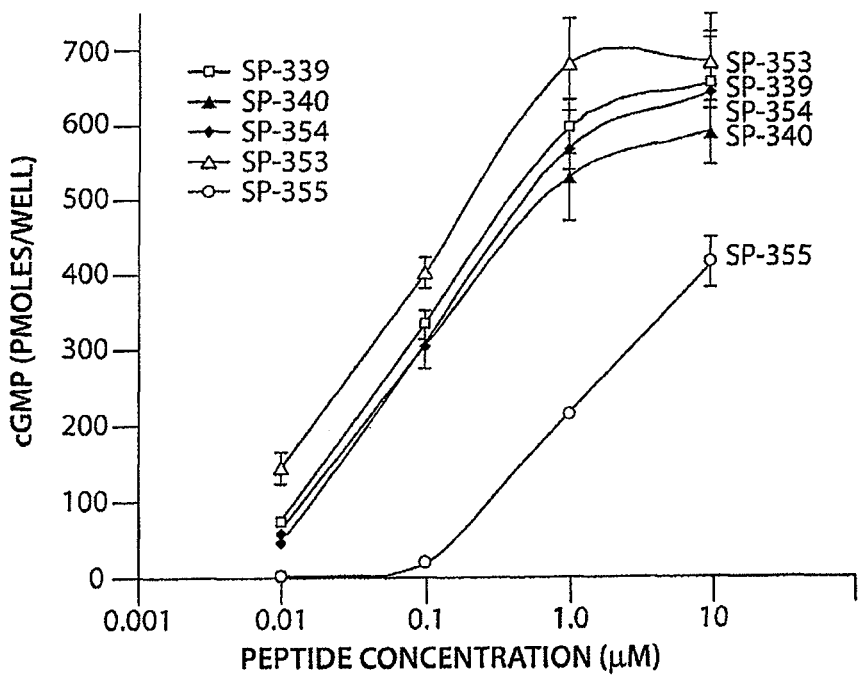
FIG. 6 shows stimulation of cGMP synthesis in T84 cells by SP-339 and other peptides. T84 Cells were exposed to the indicated peptide for 30 min and cell lysates were used to determine intracellular cGMP levels. Results are expressed as an average of triplicates±SD.
Figure 7A:
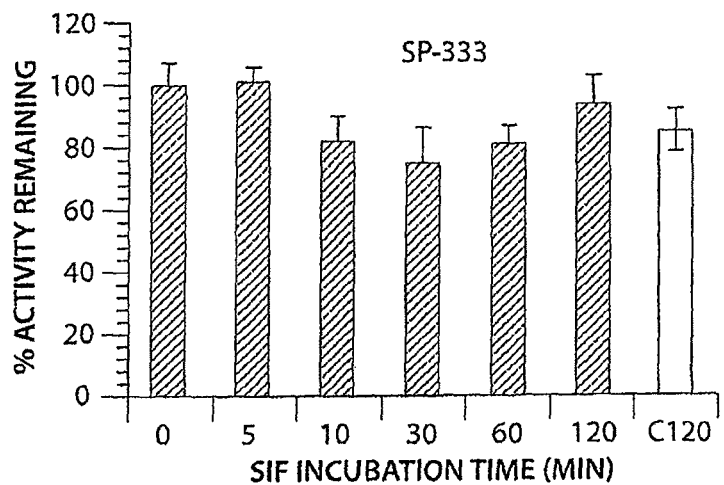
FIG. 7A shows stability of SP-333 against digestion with simulated intestinal fluid (SIF) for indicated times. The control sample marked as C120 was produced by incubating peptides with heat inactivated SIF. Samples from the incubations were removed and heated at 95° C. for 5 min to inactivate digestive enzymes and then used to stimulate cyclic GMP synthesis in T84 cells. The cGMP stimulation activity at 0 min was taken as 100% in each set. The data is average of triplicates±SD.
Figure 7B:
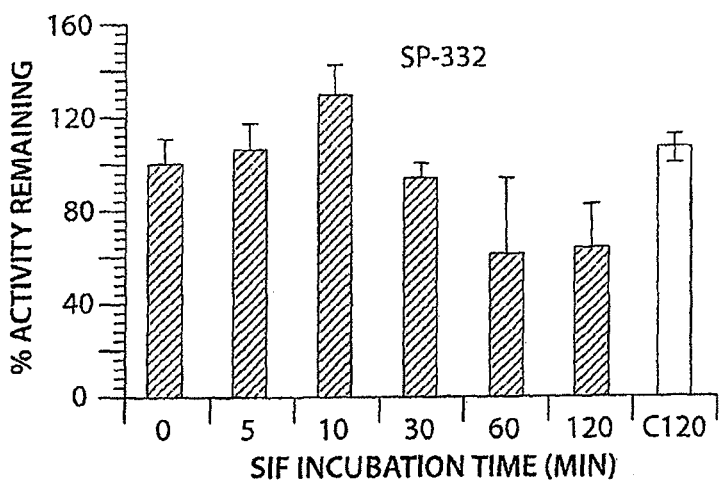
FIG. 7B shows stability of SP-332 against digestion with simulated intestinal fluid (SIF) for indicated times. The control sample marked as C120 was produced by incubating peptides with heat inactivated SIF. Samples from the digestions were removed and heated at 95° C. for 5 min to inactivate digestive enzymes and then used to stimulate cyclic GMP synthesis in T84 cells. The cGMP stimulation activity at 0 min was taken as 100% in each set. The data is average of triplicates±SD.
Figure 7C:
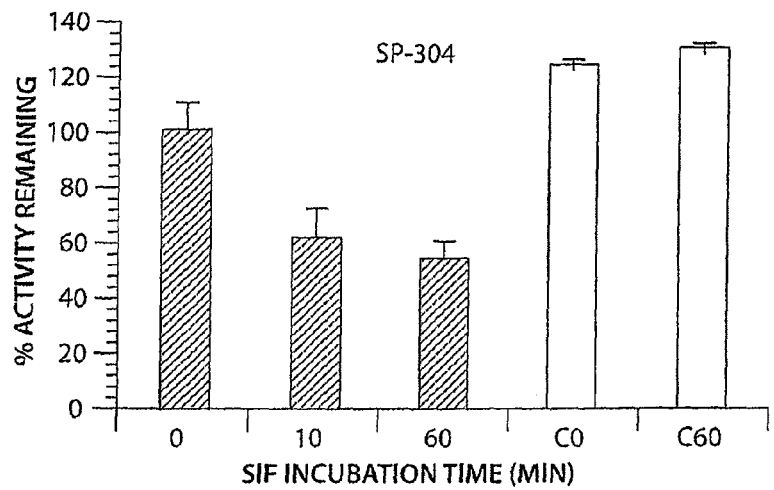
FIG. 7C shows stability of SP-304 against digestion with simulated intestinal fluid (SIF) for indicated times. The control samples marked as C0 and C60 were produced by incubating peptides with heat inactivated SIF. Samples from the digestions were removed and heated at 95° C. for 5 min to inactivate digestive enzymes and then used to stimulate cyclic GMP synthesis in T84 cells. The cGMP stimulation activity at 0 min was taken as 100% in each set. The data is average of 3 determinations±SD.
Figures 1, 7D:
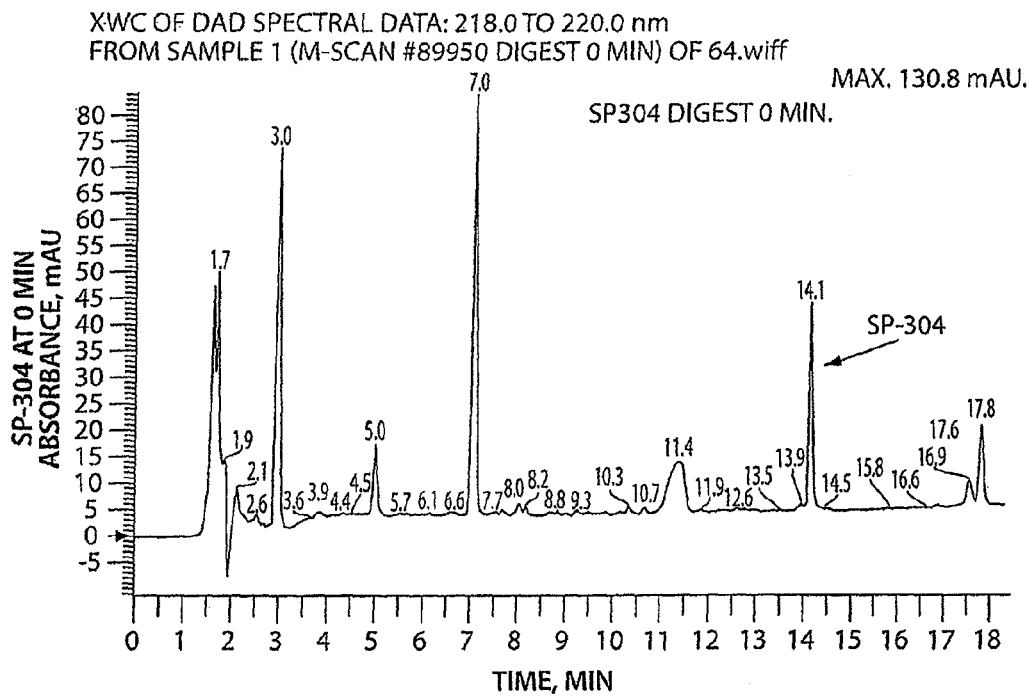
FIG. 7D shows HPLC analysis of samples of SP-304 at 0 (FIG. 7D-1) and 60 minutes (FIG. 7D-2) following incubation with SIF. Arrow indicates the elution position of SP-304 peptide. The data clearly shows that the SP-304 peak eluting at 14.3 min completely vanished and two new peaks emerged at 7.4 and 10.3 minutes. These new peptide peaks represent the possible degradation products of SP-304.
Figures 2, 7D:
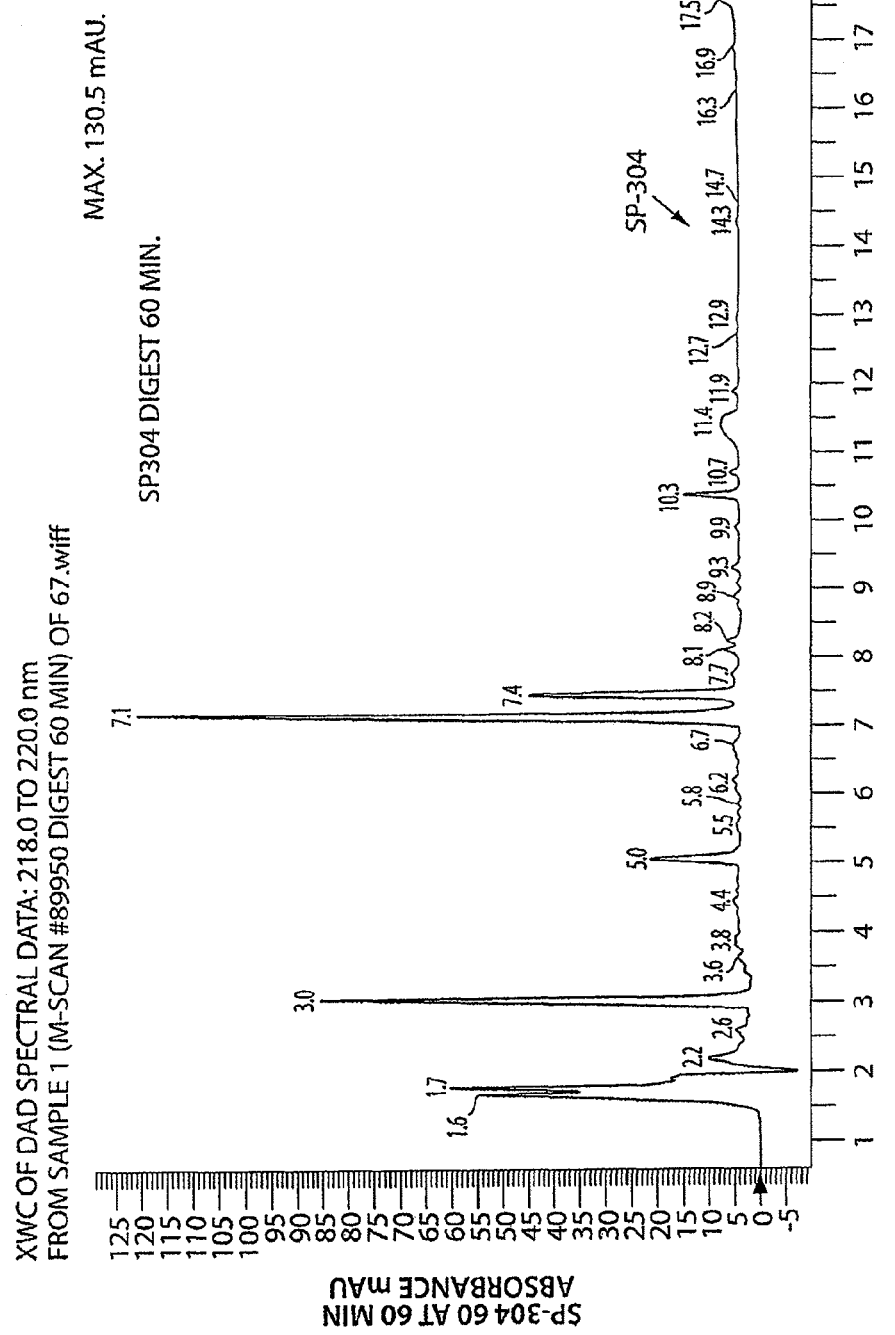
Figures 1, 7E:
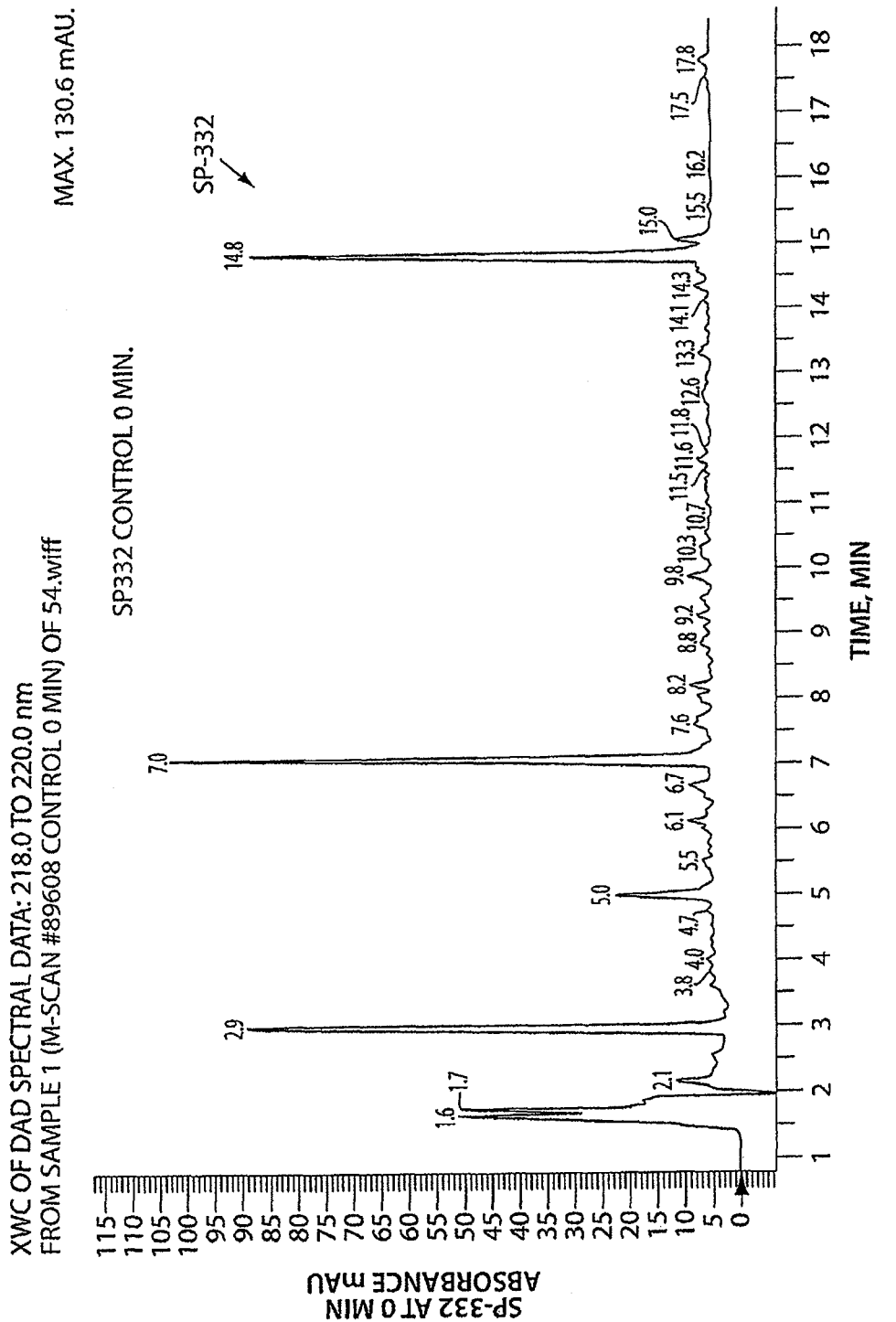
FIG. 7E shows HPLC analysis of samples of SP-332 at 0 (FIG. 7E-1) and 120 minutes (FIG. 7E-2) following incubation with SIF. Arrow indicates the elution position of SP-332 peptide. The data shows that the peptide SP-332 eluting at 14.8 minutes was not changed following incubation with SIF, suggesting that SP-332 is not sensitive to proteolysis by proteases present in SIF.
Figures 2, 7E:
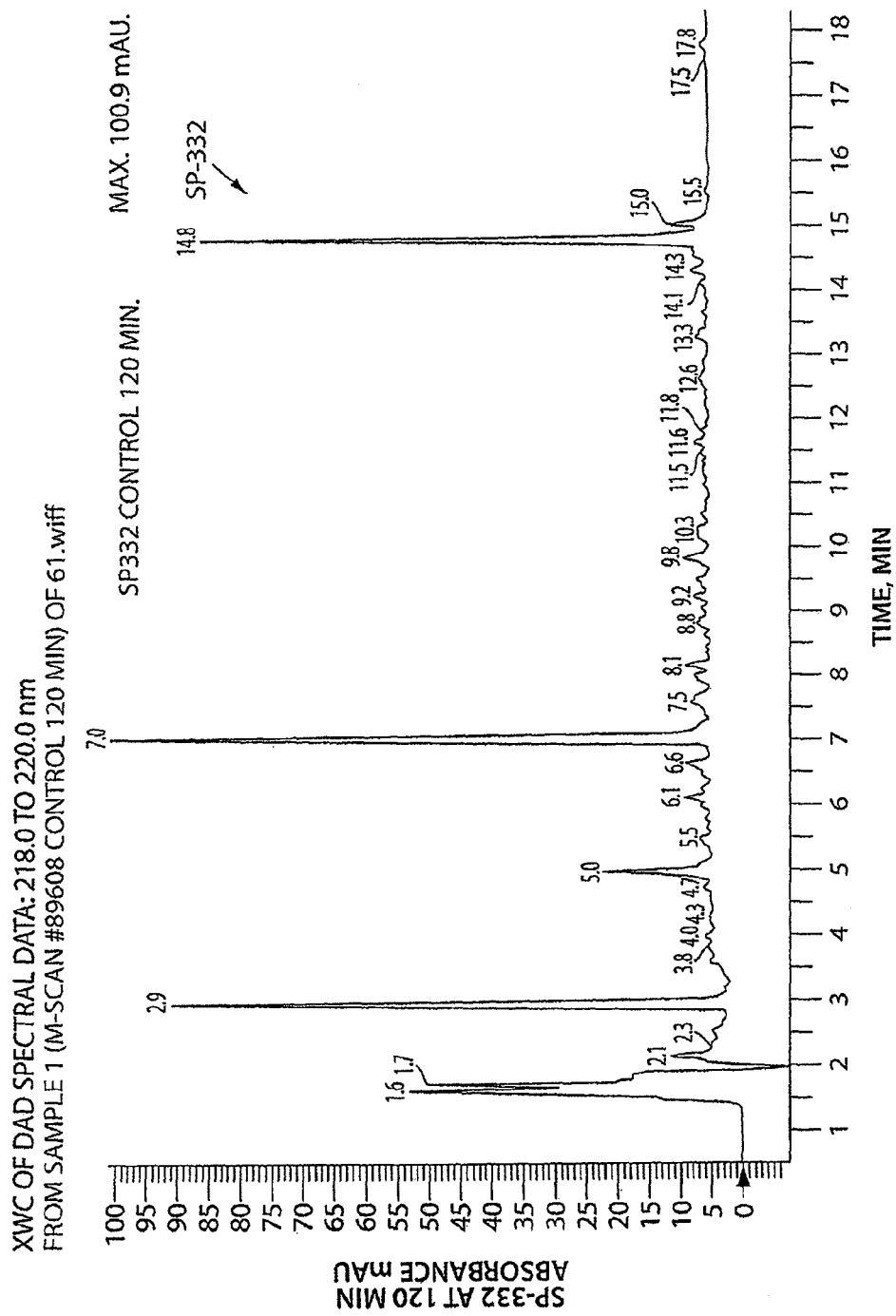
Figures 1, 7F:
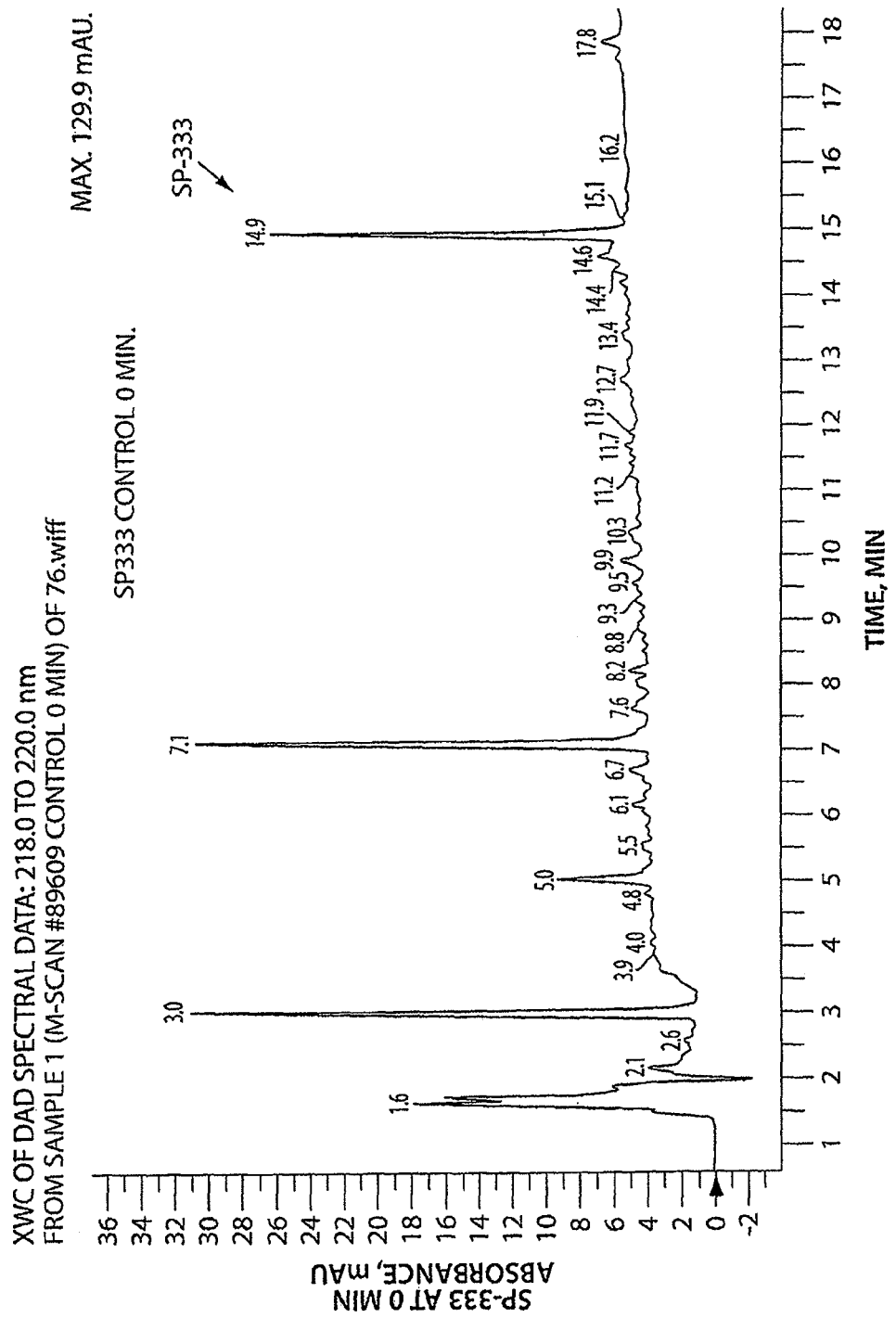
FIG. 7F shows HPLC analysis of samples of SP-333 at 0 (FIG. 7F-1) and 120 minutes (FIG. 7F-2) following incubation with SIF. Arrows indicate the elution position of SP-333. The data show that peptide SP-333, eluting at 14.8 minutes, was not changed following incubation with SIF, suggesting that SP-333 is not sensitive to proteolysis by proteases present in SIF during the 120 minute incubation period.
Figures 2, 7F:
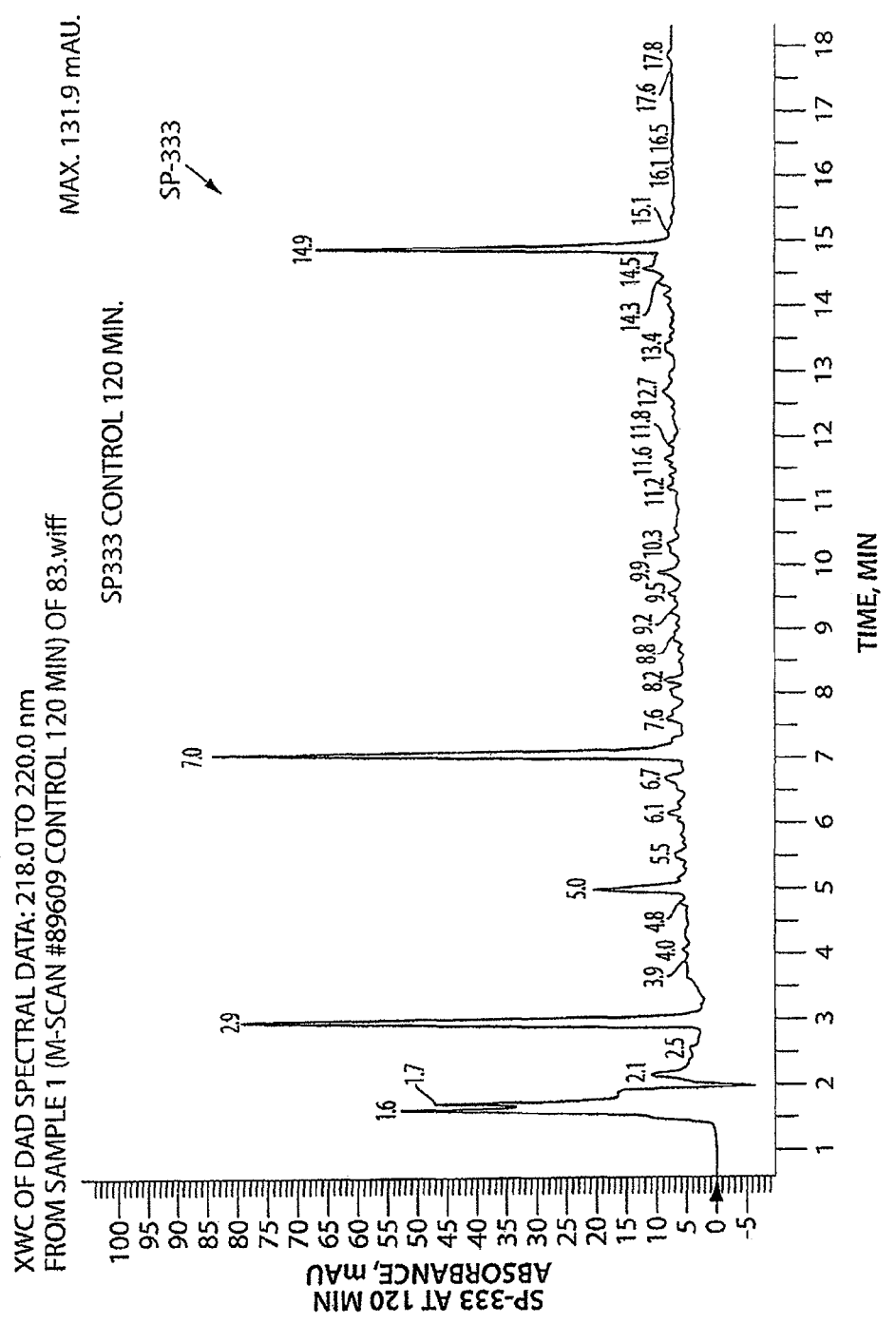
Figure 8:
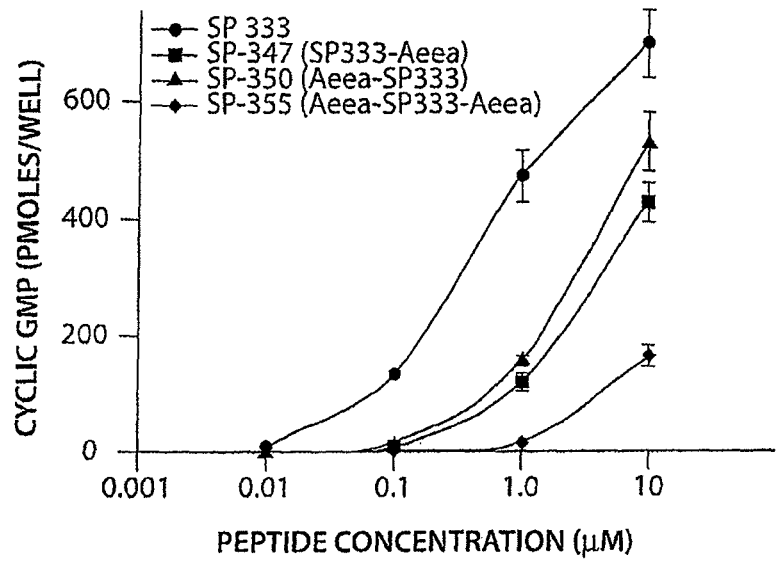
FIG. 8 shows stimulation of cGMP synthesis in T84 cells by the peggylated analogs of SP-333. T84 cells were exposed to the indicated peptides for 30 min and cell lysates were used to determine intracellular cGMP levels. Results are expressed as an average of triplicates±SD.

FIG. 6 shows results from the experiments evaluating potency of peptides that are similar to the *E. coli* enterotoxin ST peptide in the cGMP stimulation assay (as above). Among these the peptides SP-353 and SP-354 were found to be quite potent to stimulate cGMP synthesis in T84 cells. Particularly, the peptide SP-353 that has Ser residue at the 6$^{th}$ position was found to be the most potent among the peptides tested. The peptide SP-355 that has D-Tyr at the C-terminus showed potency markedly less than the other peptides.

Example 5

Peggylated Peptides

An additional strategy to render peptides more resistant towards digestion by digestive proteases is to peggylate them at the N- and C-terminus. The peptide SP-333 was peggylated with the aminoethyloxy-ethyloxy-acetic acid (Aeea) group at the C-terminus (SP-347) or at the N-terminus (SP-350) or at both termini (SP-343). Cyclic GMP synthesis in T84 cells was measured by the method as described above.

The peptides SP-347 and SP-350 showed potencies comparable to SP-333 in their abilities to stimulate cGMP synthesis in T84 cells. However, peptide SP-343 was considerably less potent as compared to the other peptides tested. The poor activity of SP-343 might be due to the considerable steric hindrance afforded by the large Aeea groups at both termini.

Example 6

Combination of Guanylate Cyclase Receptor Agonists with Phosphodiesterase Inhibitors Regulation of intracellular concentrations of cyclic nucleotides (i.e., cAMP and cGMP) and thus, signaling via these second messengers, has been generally considered to be governed by their rates of production versus their rates of destruction within cells. Thus, levels of cGMP in tissues and organs can also be regulated by the levels of expression of cGMP-specific phosphodiesterases (cGMP-PDE), which are generally overexpressed in cancer and inflammatory diseases. Therefore, a combination consisting of an agonist of GC-C with an inhibitor of cGMP-PDE might produce synergistic effect on levels of cGMP in the target tissues and organs.

Figure 10:
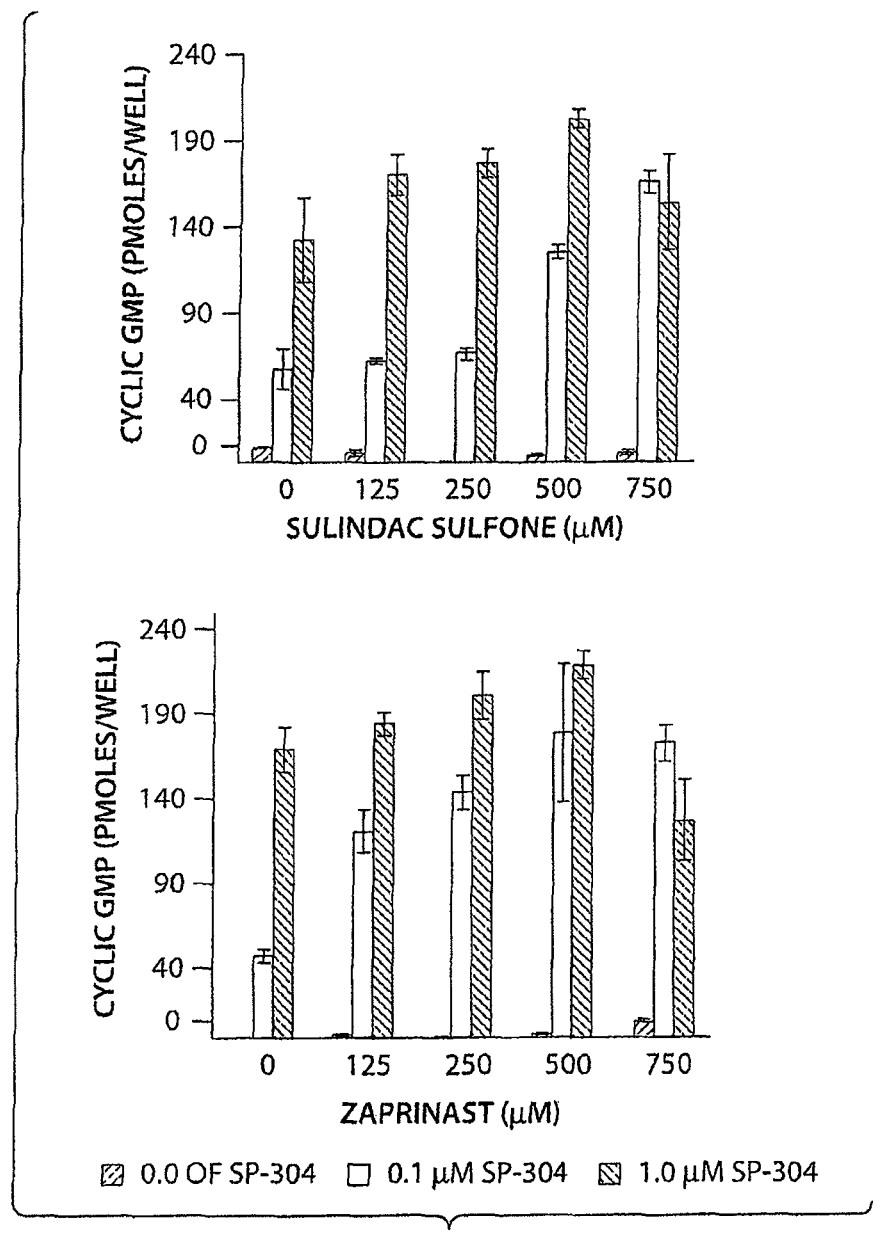
FIG. 10 shows stimulation of cGMP synthesis in T84 cells by SP-304 (0.1 or 1.0 µM) either alone or in combination with incremental concentrations of phosphodiesterase (PDE) inhibitors, as indicated (upper panel: sulindac sulfone; lower panel: zaprinast). T84 cells were exposed to various treatments, as indicated, for 30 min and the cell lysates were used to determine the intracellular cGMP levels. Results are expressed as an average of duplicates.
Figure 11:
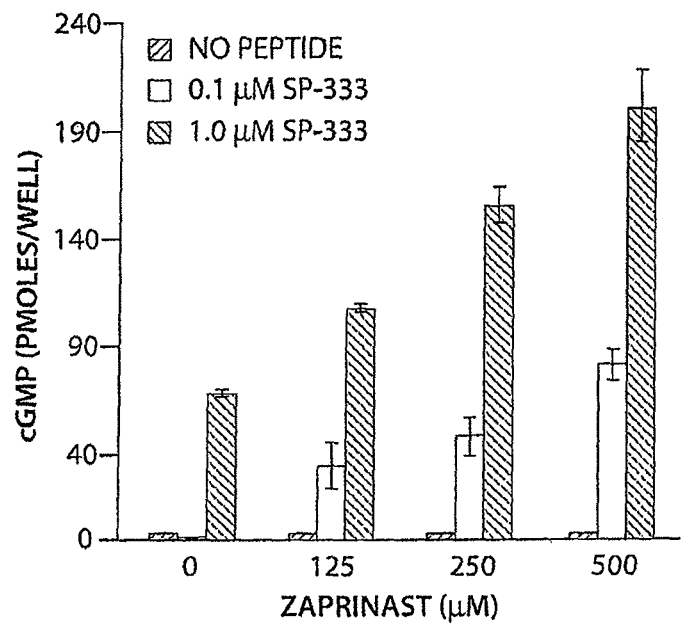
FIG. 11 shows stimulation of cGMP synthesis in T84 by SP-333 (0.1 or 1.0 µM) either alone or in combination with incremental concentrations Zaprinast, as indicated. T84 cells were exposed to various treatments, as indicated, for 30 min and the cell lysates were used to determine the intracellular cGMP levels. Results are expressed as an average of duplicates.
Figure 12:
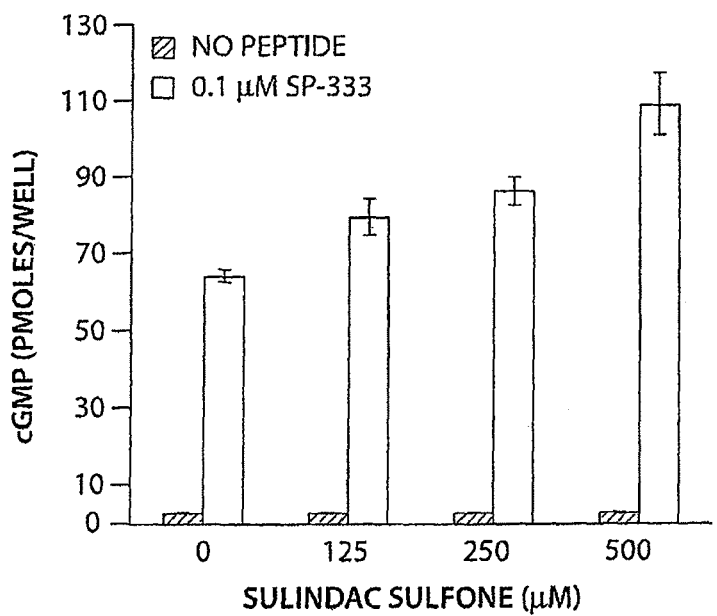
FIG. 12 shows stimulation of cGMP synthesis in T84 by SP-333 (0.1 µM) either alone or in combination with incremental concentrations Sulindac Sulfone, as indicated. T84 cells were exposed to various treatments, as indicated, for 30 min and the cell lysates were used to determine the intracellular cGMP levels. Results are expressed as an average of duplicates.
Figure 13:
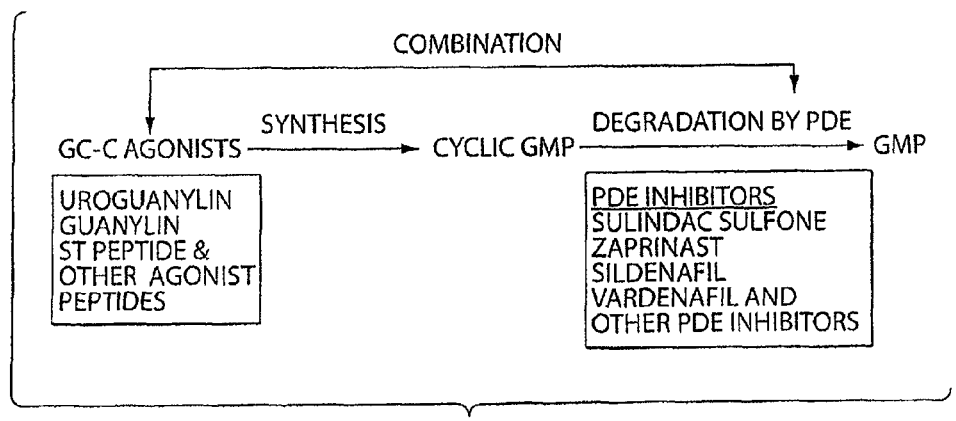
FIG. 13 shows a schematic of the maintenance of intracellular concentrations of cGMP levels. The intracellular levels of cGMP can be maintained by stimulating its synthesis via the activation of GC-C and by inhibiting its degradation by cGMP-PDE. Thus, a combination of a GC-C agonist with an inhibitor of PDE may produce a synergistic effect to enhance levels of cGMP in tissues and organs.

Sulindac Sulfone (SS) and Zaprinast (ZAP) are two of the known inhibitors of cGMP-PDE and have been shown to induce apoptosis in cancer cells via a cGMP-dependent mechanism. SS and ZAP in combination with SP304 or SP-333 was evaluated to see if these PDE inhibitors had any synergistic effect on intracellular accumulation of cGMP (FIG. 9-12). As the data shows, SS at concentration of 100 µM did not enhance intracellular accumulation of cGMP. However, the combination SS with SP304 stimulated cGMP production several fold more then the stimulation by SP304 used alone. This synergistic effect on cGMP levels was more pronounced when SP304 were used at 0.1 µM concentration (FIG. 10). Similar observations were made when SP304 or SP333 were used in combination with ZAP (FIG. 10, FIG. 11 and FIG. 12). These results suggest that the intracellular levels of cGMP are stabilized because SS inhibits cGMP-PDE that might be responsible for depletion of intracellular cGMP. Thus, the approach to use a combination of GC-C agonist with a cGMP-PDE inhibitor is attractive.

Figure 9:
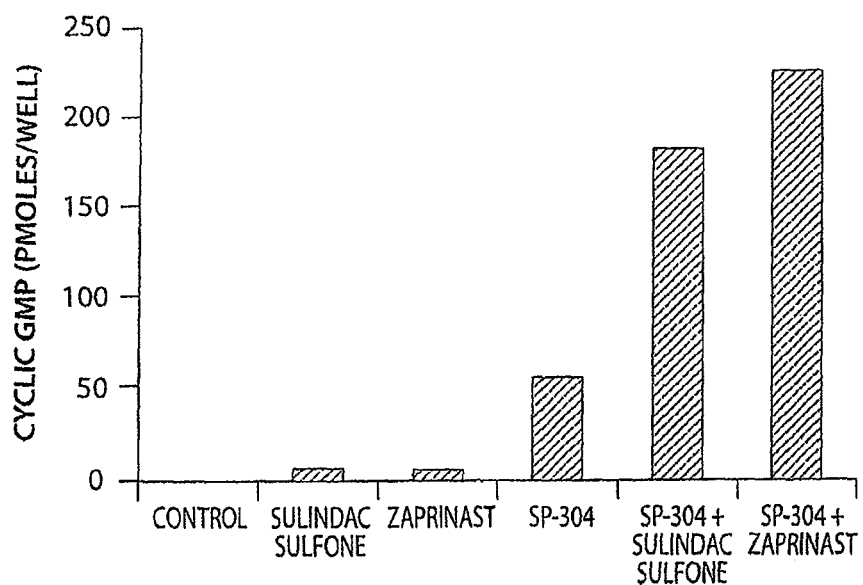
FIG. 9 shows stimulation of cGMP synthesis in T84 cells by SP-304 (0.1 µM) either alone or in combination with the phosphodiesterase (PDE) inhibitors Sulindac Sulfone (100 µM) or Zaprinast (100 µM). T84 cells were exposed to various treatments, as indicated, for 30 min and the cell lysates were used to determine the intracellular cGMP levels. Results are expressed as an average of duplicates.

For the results shown in FIG. 9, cyclic GMP synthesis in T84 cells was assessed essentially as described in Shailubhai et al., Cancer Research 60, 5151-5157 (2000). Briefly, confluent monolayers of T-84 cells in 24-well plates were washed twice with 250 µl of DMEM containing 50 mM HEPES (pH 7.4) and pre-incubated at 37° C. for 10 minutes with 250 µl of DMEM containing 50 mM HEPES (pH 7.4) and 1 mM isobutyl methylxanthine (IBMX). Monolayers of T84 cells were then incubated with 250 µl of DMEM containing 50 mM HEPES (pH 7.4) containing SP-304 or PDE inhibitors either alone or in combinations, as indicated below in the following experimental sets: 1) Control; 2) SP-304 (0.1 µM); 3) Sulindac Sulfone (100 µM); 4) Zaprinast (100 µM); 5) SP-304 (0.1 µM)+Sulindac Sulfone (100 µM); and 6) SP-304 (0.1 µM)+Zaprinast (100 µM). After the 30 min incubation, the medium was aspirated and the reaction was terminated by the addition of 3% perchloric acid. Following centrifugation and the addition of NaOH (0.1 N) to neutralize the pH, intracellular cGMP levels were determined in lysates using a cGMP ELISA kit (Cat. No. 581021; Cayman Chemical, Ann Arbor, Mich.). Samples were run in duplicates incubations and each sample was run as duplicates in ELISA test.

For the results shown in FIG. 10, the method used was same as the one used for FIG. 9 except that the monolayers of T84 cells were incubated with 500 µl of DMEM containing 50 mM HEPES (pH 7.4) containing SP-304 (0.1 or 1.0 µM) or increasing concentrations of PDE inhibitors (0 to 750 µM) either alone or in combination with SP-304. After the 30 min incubation, the medium was aspirated and the reaction was terminated by the addition of 3% perchloric acid. Following centrifugation and the addition of NaOH (0.1 N) to neutralize the pH, intracellular cGMP levels were determined in lysates using a cGMP ELISA kit (Cat. No. 581021; Cayman Chemical, Ann Arbor, Mich.). Samples were run as triplicates in ELISA test.

For the results shown in FIG. 11, the method used was same as the one used for FIG. 10 except that the monolayers of T84 cells were incubated with 500 µl of DMEM containing 50 mM HEPES (pH 7.4) containing SP-3333 (0.1 or 1.0 µM) or increasing concentrations of ZAP (0 to 500 µM) either alone or in combination with SP-333. After the 30 min incubation, the medium was aspirated and the reaction was terminated by the addition of 3% perchloric acid. Following centrifugation and the addition of NaOH (0.1 N) to neutralize the pH, intracellular cGMP levels were determined in lysates using a cGMP ELISA kit (Cat. No. 581021; Cayman Chemical, Ann Arbor, Mich.). Samples were run as triplicates in ELISA test.

For the results shown in FIG. 12, the method used was same as the one used for FIG. 10 except that the monolayers of T84 cells were incubated with 500 µl of DMEM containing 50 mM HEPES (pH 7.4) containing SP-333 (0.1 µM) or increasing concentrations of Sulindac Sulfone (0 to 500 µM) either alone or in combination with SP-333. After the 30 min incubation, the medium was aspirated and the reaction was terminated by the addition of 3% perchloric acid. Following centrifugation and the addition of NaOH (0.1 N) to neutralize the pH, intracellular cGMP levels were determined in lysates using a cGMP ELISA kit (Cat. No. 581021; Cayman Chemical, Ann Arbor, Mich.). Samples were run as triplicates using the ELISA test.

Example 7

An Oral Range-Finding Toxicity Study in Cynomolgus Monkeys

The objective of the study is to determine the toxicity of the GRCA peptides according to the invention following a single oral gavage administration to the cynomolgus monkey and to allow assessment of reversibility of any changes following a minimum 7-day observation/washout period. Each GRCA peptide according to the invention will be given at two different dose levels.

Experimental Design

The test (e.g., the GRCA peptides according to the invention) and control/vehicle article will be administered in three phases separated by a minimum 7-day observation period. Each phase will consist of a single oral gavage administration to female cynomolgus monkeys as indicated in the tables below:

Phase 1:

Eight non-naive female cynomolgus monkeys will be transferred from the ITR Spare Monkey colony and assigned to four dose groups as follows:

| Group Number | Group Designation | Study Days | Dose Level (mg/kg) | Dose Concentration (mg/mL) | Dose Volume (mL/kg) | Number of Animals (Females) |
|---|---|---|---|---|---|---|
| 1 | Control/Vehicle | 1 4 | 0 | 0 | 10 | 2 |
| 2 | Test Peptides | 1 4 4 | 1 | 0.1 | 10 | 2 |

Following completion of the Phase 1 dosing, all monkeys will be observed for 33 days. Upon completion of the observation period, all monkeys will be transferred back to the ITR Spare Monkey Colony.

Phase 2:

The same eight non-naive female cynomolgus monkeys as previously used in Phase 1 will be transferred from the ITR Spare Monkey colony and assigned to four dose groups as follows:

| Group Number | Group Designation | Study Day | Dose Level (mg/kg) | Dose Concentration (mg/mL) | Dose Volume (mL/kg) | Number of Animals (Females) |
|---|---|---|---|---|---|---|
| 1 | Control/Vehicle | 1 | 10 | 1 | 10 | 2 |
| 2 | Test Peptides | 1 | 10 | 1 | 10 | 2 |

Following completion of the Phase 2 dosing, all monkeys will be observed for a minimum of 7 days.

Route of Administration

The oral route of administration has been chosen because it is a preferred human therapeutic route.

Preparation of Test and Control/Vehicle Articles

The test and control/vehicle articles will be prepared fresh on the day of dosing in cold distilled water (maintained in an ice water bath). A sufficient amount of test article powder will be added to the appropriate amount of distilled water in order to achieve the desired concentration. The dose formulations will be mixed by simple inversion.

Analysis of Test Article Concentration and Stability in the Dose Formulations

For possible confirmation of the concentration and stability of the test article in the formulations, representative samples will be taken from the middle of each concentration, including the control/vehicle article on the first day of dosing of each group, as indicated below. Samples will be collected immediately after preparation on Day 1 and again after dosing is completed on that day and will be stored frozen (approximately 80° C. nominal) in 20 mL screw cap vials. Therefore, the remaining dose formulation vials will be returned to the Pharmacy Department as soon as possible after completion of dosing.

Group 1: 1.5 mL in duplicate from the middle on Day 1 (pre-dose and post-dose).

Group 2: 1.5 mL in duplicate from the middle on Day 1 (pre-dose and post-dose).

Group 3: 1.5 mL in duplicate from the middle on Day 1 (pre-dose and post-dose).

Group 4: 1.5 mL in duplicate from the middle on Day 1 (pre-dose and post-dose).

The formulations will be maintained cold in an ice water bath during all sampling procedures.

The formulations will be stirred continuously with a stir bar for a minimum of 15 minutes prior to sampling.

The samples will be retained frozen (approximately −80° C. nominal) at ITR until requested by the Sponsor to be shipped to a laboratory designated by the Sponsor for analysis. The samples can be discarded once it is determined by the analyst and Study Director that they are no longer needed. These samples' disposition will be recorded in the raw data.

If analyzed, a Dose Formulation report will be prepared by the Principal Investigator (Formulation analysis) and will be provided to ITR for inclusion in the final report.

Test System

Species/Strain: Cynomolgus Monkey (Macaca Fasicularis)
Source: orldwide Primates Inc.,
P.O. Box 971279
Miami, Fla., 33187, USA
and
Covance Research Products Inc.
P.O. Box 549
Alice, Tex., 78333, USA
Total No. of monkeys on study: 8 non-naive females
Body Weight Range: 2-4 kg at onset of treatment
Age Range at Start: Young adult at onset of treatment
Acclimation Period The animals will be transferred from ITR's spare monkey colony. They are therefore, considered to be fully acclimated to the laboratory environment.

The actual age and body weight ranges will be noted in the final report.

Administration of the Test and Control/Vehicle Articles

The test and control/vehicle articles will be administered by oral gavage administration using a gavage tube attached to a syringe in three Phases separated by a minimum 7-day observation/washout period. Each dosing session will consist of a single oral gavage administration. The gavage tube will be flushed with 3 mL of reverse osmosis water immediately following administration of the dose formulation in order to ensure that the entire dose volume has been delivered to the animal. The dose volume will be 10 mL/kg for all animals, including controls. The actual volume administered to each monkey on Day 1 of each Phase will be calculated using the Day −1 body weights of each Phase.

Dosing formulations will be maintained cold during dose administration by placing them in an ice water bath.

The dosing formulations must be placed on a stir plate for a minimum of 15 minutes prior to the start of dosing and maintained on the stir plate throughout the dosing procedure.

The dosing formulations must be used within 2 hours of preparation.

Clinical Observations

Cage-side clinical signs (ill health, behavioral changes etc.) will be recorded as indicated below except on detailed clinical examination days, where the morning cage-side clinical signs will be replaced by a detailed clinical examination (DCE). During regular cage side clinical signs and detailed examinations, particular attention will be paid to stools with respect to amount of stools produced, description of stools, etc.

Cage side clinical signs will be performed as follows:

During the pretreatment period and during the 7-day (minimum) observation periods: Three times per day with a minimum of 3 hours between each occasion.

On the dosing day of Phase 1: pre-dose, 2, 4, 6, 8 and 24 hours post-dosing

On the dosing day of Phase 2: pre-dose, continuously for the first 4 hours post-dose and at 6, 8 and 24 hours post-dosing On the dosing day of Phase 3: pre-dose, continuously for the first 4 hours post-dose and at 6, 8 and 24 hours post-dosing A detailed clinical examination of each monkey will be performed once at the time of animal transfer and once weekly thereafter.

Animals whose health status is judged to warrant additional evaluation will be examined by a Clinical Veterinarian, or a technician working under the supervision of the Clinical Veterinarian. Any veterinarian-recommended treatments will only be performed once agreement has been obtained from the Study Director. Where possible, the Sponsor will be consulted prior to administration of therapeutic drugs.

Body weights will be recorded for all animals once daily from the day of transfer through to the end of the study.

Food consumption will be recorded for all animals once daily from the day of transfer through to the end of the study.

Cages will be cleaned prior to the start of the daily food consumption to ensure no food cookies remain in the cage. Monkeys will be fed 7 cookies before 12 pm and 7 cookies after 12 pm. The sum of the total number of cookies given for the day will be recorded.

The next morning, a visual check will be performed to see how many cookies are left in the cage. The number of whole cookies remaining in the food hopper or on the tray will be recorded. The number of whole cookies left will be subtracted from the total number of cookies given in order to calculate the number of cookies eaten.

Example 8

Suckling Mouse Model of Intestinal Secretion (SuMi Assay)

The GCRA peptides described herein can be tested for their ability to increase intestinal secretion using a suckling mouse model of intestinal secretion. In this model a GCRA peptide is administered to suckling mice that are between seven and nine days old. After the mice are sacrificed, the gastrointestinal tract from the stomach to the cecum is dissected ("guts"). The remains ("carcass") as well as the guts are weighed and the ratio of guts to carcass weight is calculated. If the ratio is above 0.09, one can conclude that the test compound increases intestinal secretion. Controls for this assay may include wild-type SP-304, ST polypeptide and Zelnorm®. Phenylbenzoquinone-induced writhing model The PBQ-induced writhing model can be used to assess pain control activity of the GCRA peptide described herein. This model is described by Siegmund et al. (1957 Proc. Soc. Exp. Bio. Med. 95:729-731). Briefly, one hour after oral dosing with a test compound, e.g., a GCRA peptide, morphine or vehicle, 0.02% phenylbenzoquinone (PBQ) solution (12.5 mL/kg) is injected by intraperitoneal route into the mouse. The number of stretches and writhings are recorded from the $5^{th}$ to the $10^{th}$ minute after PBQ injection, and can also be counted between the $35^{th}$ and $40^{th}$ minute and between the $60^{th}$ and $65^{th}$ minute to provide a kinetic assessment. The results are expressed as the number of stretches and writhings (mean±SEM) and the percentage of variation of the nociceptive threshold calculated from the mean value of the vehicle-treated group. The statistical significance of any differences between the treated groups and the control group is determined by a Dunnett's test using the residual variance after a one-way analysis of variance ($P<0.05$) using SigmaStat Software.

Example 9

Pharmacokinetic Property Determination of Gcra Peptides

Serum samples are extracted from the whole blood of exposed (mice dosed orally or intravenously with GCRA peptides (s) described herein) and control mice, then injected directly (10 mL) onto an in-line solid phase extraction (SPE) column (Waters Oasis HLB 25 μm column, 2.0×15 mm direct connect) without further processing. The sample on the SPE column is washed with a 5% methanol, 95% $dH_2O$ solution (2.1 mL/min, 1.0 minute), then loaded onto an 0 analytical column using a valve switch that places the SPE column in an inverted flow path onto the analytical column (Waters Xterra MS C8 5 μm IS column, 2.1×20 mm). The sample is eluted from the analytical column with a reverse phase gradient (Mobile Phase A: 10 mM ammonium hydroxide in $dH_2O$, Mobile Phase B: 10 mM ammonium hydroxide in 80% acetonitrile and 20% methanol; 20% B for the first 3 minutes then ramping to 95% B over 4 min. and holding for 2 5 min., all at a flow rate of 0.4 mL/min.). At 9.1 minutes, the gradient returns to the initial conditions of 20% B for 1 min. polypeptide is eluted from the analytical column and is detected by triple-quadrapole mass spectrometry (MRM, 764 (+2 charge state)>182 (+1 charge state) Da; cone voltage=30V; collision=20 eV; parent resolution=2 Da at base peak; daughter resolution=2 Da at base peak). Instrument response is converted into concentration units by comparison with a standard curve using known amounts of chemically synthesized polypeptide(s) prepared and injected in mouse plasma using the same procedure.

Similarly, pharmacokinetic properties are determined in rats using LCMS methodology. Rat plasma samples containing the GCRA peptide are extracted using a Waters Oasis MAX 96 well solid phase extraction (SPE) plate. A 200 μL volume of rat plasma is mixed with 200 μL of $^{13}$Cg, $^{15}$N-labeled polypeptide in the well of a prepared SPE plate. The samples are drawn through the stationary phase with 15 mm Hg vacuum. All samples are rinsed with 200 μL of 2% ammonium hydroxide in water followed by 200 μL of 20% methanol in water. The samples are eluted with consecutive 100 µL volumes of May 20, 1975 formic acid/water/methanol and 100 µL May 15, 1980 formic acid/water/methanol. The samples are dried under nitrogen and resuspended in 100 µL of 20% methanol in water. Samples are analyzed by a Waters Quattro Micro mass spectrometer coupled to a Waters 1525 binary pump with a Waters 2777 autosampler. A 40 µL volume of each sample is injected onto a Thermo Hypersil GOLD C18 column (2.1×50 mm, 5 um). polypeptide is eluted by a gradient over 3 minutes with acetonitrile and water containing 0.05% trifluoroacetic acid. The Quattro Micro mass spectrometer is run in multiple reaction monitoring (MRM) mode using the mass transitions of, for example 764>182 or 682>136. Using this methodology, polypeptide is dosed orally and by IV to rats at 10 mg/kg. Pharmacokinetic properties including area under the curve and bioavailability are determined.

Example 10

Diuresis Related Experiments Effect on Diuresis and Natriuresis

The effect of GCRA peptides described herein on diuresis and natriuresis can be determined using methodology similar to that described in WO06/001931 (examples 6 (p. 42) and 8 (p. 45)). Briefly, the polypeptide/agonist described herein (180-pmol) is infused for 60 min into a group of 5 anesthetized mice or primates. Given an estimated rat plasma volume of 10 mL, the infusion rate is approximately 3 pmol/mL/min. Blood pressure, urine production, and sodium excretion are monitored for approximately 40 minutes prior to the infusion, during the infusion, and for approximately 50 minutes after the infusion to measure the effect of the GCRA peptides on diuresis and natriuresis. For comparison, a control group of five rats is infused with regular saline. Urine and sodium excretion can be assessed. Dose response can also be determined. polypeptide/GC-C agonist described herein is infused intravenously into mice or primates over 60 minutes. Urine is collected at 30 minute intervals up to 180 minutes after termination of polypeptide/GC-C agonist infusion, and urine volume, sodium excretion, and potassium excretion are determined for each collection interval. Blood pressure is monitored continuously. For each dose a dose-response relationship for urine volume, sodium and potassium excretion can be determined. Plasma concentration of the polypeptide/GC-agonist is also determined before and after iv infusion.

Mouse or Primate Diuresis Experiment: Once an appropriate level of anesthesia has been achieved, a sterile polyurethane catheter is inserted into the urethra and secured using 1-2 drops of veterinary bond adhesive applied to urethra/catheter junction. Animals are then dosed with either vehicle or test article via the intravenous or intraperitoneal route. Animals are allowed to regain consciousness, and the volume of urine excreted over a 1-5 hour duration is recorded periodically for each rat.

REFERENCES

1. Currie, et al., *Proc. Nat'l Acad. Sci. USA* 89:947-951 (1992).
2. Hamra, et al., *Proc. Nat'l Acad. Sci. USA* 90:10464-10468 (1993).
3. Forte, L., *Reg. Pept.* 81:25-39 (1999).
4. Schulz, et al., *Cell* 63:941-948 (1990).
5. Guba, et al., *Gastroenterology* 111:1558-1568 (1996).
6. Joo, et al., *Am. J. Physiol.* 274:G633-G644 (1998).
7. Evan, et al., *Nature (London)* 411:342-348 (2001).
8. Eastwood, G., *J. Clin. Gastroenterol.* 14:S29-33 (1992).
9. Lipkin, M. *Arch. Fr. Mal. Appl Dig.* 61:691-693 (1972).
10. Wong, et al., *Gut* 50:212-217 (2002).
11. Potten, et al., *Stem Cells* 15:82-93.
12. Basoglu, et al., in: Proceedings of the Second FEPS Congress, Jun. 29-Jul. 4, 1999, Prague, Czech Republic., lf2.cuni.cz/physiolres/feps/basoglu
13. Sindic, et al., *J. Biol. Chem.* Mar. 11, 2002, manuscript M110627200 (in press).
14. Askling, J., Dickman, P. W., Karlen, P., Brostrom, O., Lapidus, A., Lofberg, R., and Ekbom, A. Colorectal cancer rates among first-degree relatives of patients with inflammatory bowel disease: a population-based cohort study. *Lancet,* 357: 262-266,
15. Provenzale, D. and Onken, J. Surveillance issues in inflammatory bowel disease: Ulcerative colitis. *J Clin Gastroenterol,* 32:99-105, 2001.
16. Ettorre, G. M, Pescatori, M., Panis, Y., Nemeth, J Crescenzi, A., and Valleur, P. Mucosal changes in ileal pouches after restorative proctocolectomy for ulcerative and Crohn's colitis. Dis Colon Rectum, 43:1743-1748, 2000.
17. Shinozaki M, Watanabe T, Kubota Y, Sawada T, Nagawa H, Muto T. High proliferative activity is associated with dysplasia in ulcerative colitis. Dis Colon Rectum, 43:S34-S39, 2000.
18. Deschner, E. E., Winawer, S. J., Katz, S., Katzka, I., and Kahn, E. Proliferative defects in ulcerative colitis patients. Cancer Invest, 1:41-47, 1983.
19. Wong, W. M., and Wright, N. A. Cell proliferation and gastrointestinal mucosa. J Clin Pathol, 52:321-333.
20. Potten, C. S., Wilson, J. W., and Booth, C. Regulation and significance of apoptosis in the stem cells. Stem Cells, 15:82-93.
21. Bhakdi, et al., *Infect. Immun.* 57:3512-3519 (1989).
22. Hughes, et al., *J. Biol. Chem.* 272:30567-30576 (1997).
23. Cermak, et al., *Pflugers Arch.* 43:571-577 (1996).
24. Wu, et al., *J. Biol. Chem.* 272:14860-14866 (1997).
25. Shailubhai et al., Cancer Research 60, 5151-5157 (2000)
26. Shailubhai et al., Curr. Opin. Drug Disc. Dev. 5(2): 261-268, 2002.
27. Collins, S M. *J Clin Gastroenterol.* 41 Suppl 1:S30-32 (2007)
28. Ramamoorthy S et al., *J Biol Chem.* 282(16):11639-11647 (2007)

We claim:

1. A peptide consisting essentially of the amino acid sequence of SEQ ID NO:9, wherein said peptide is a [4:12, 7:15] bicyclic peptide.

2. A pharmaceutical composition in unit dose comprising a guanylate cyclase receptor agonist peptide having the sequence of SEQ ID NO:9, wherein said peptide is a [4:12, 7:15] bicyclic peptide, present in a therapeutically effective amount and a pharmaceutical carrier, excipient or diluent.

3. The pharmaceutical composition of claim 2, wherein the unit dose form is selected from the group consisting of a tablet, a capsule, a solution and inhalation formulation.

4. A method of increasing cGMP production in a cell comprising contacting said cell with a peptide consisting of the amino acid sequence of SEQ ID NO:9, wherein said peptide is a [4:12,7:15] bicyclic peptide.

5. The method of claim 4, further comprising contacting said cell with a cGMP-dependent phosphodiesterase inhibitor.

6. The method of claim 5, wherein said cGMP-dependent phosphodiesterase inhibitor is selected from the group consisting of sulindac sulfone, zaprinast, and motapizone, vardenafil, and sildenafil.

* * * * *